(12) United States Patent
Panja

(10) Patent No.: US 9,267,935 B2
(45) Date of Patent: Feb. 23, 2016

(54) USE AND IDENTIFICATION OF BIOMARKERS FOR GASTROINTESTINAL DISEASES

(71) Applicant: AlfaGene Bioscience, Inc., Fords, NJ (US)

(72) Inventor: Asit Panja, Somerset, NJ (US)

(73) Assignee: AlfaGene Bioscience, Inc., Fords, NJ (US)

( * ) Notice: Subject to any disclaimer, the term of this patent is extended or adjusted under 35 U.S.C. 154(b) by 0 days.

(21) Appl. No.: 13/947,841

(22) Filed: Jul. 22, 2013

(65) Prior Publication Data

US 2013/0303398 A1 Nov. 14, 2013

Related U.S. Application Data

(63) Continuation of application No. 12/577,141, filed on Oct. 9, 2009, now abandoned.

(60) Provisional application No. 61/195,646, filed on Oct. 9, 2008.

(51) Int. Cl.

| | | |
|---|---|---|
| *C12N 5/00* | (2006.01) | |
| *C12Q 1/68* | (2006.01) | |
| *G01N 33/53* | (2006.01) | |
| *G01N 33/50* | (2006.01) | |
| *G01N 33/574* | (2006.01) | |
| *C12N 5/071* | (2010.01) | |

(52) U.S. Cl.
CPC .......... *G01N 33/5044* (2013.01); *C12Q 1/6886* (2013.01); *G01N 33/57419* (2013.01); *G01N 33/57446* (2013.01); *C12N 5/068* (2013.01); *C12N 5/0679* (2013.01); *C12Q 1/68* (2013.01); *C12Q 2600/136* (2013.01); *C12Q 2600/158* (2013.01); *G01N 33/53* (2013.01); *G01N 2500/10* (2013.01); *G01N 2800/065* (2013.01)

(58) Field of Classification Search
CPC ........ C12N 5/0679; C12N 5/068; C12Q 1/68; C12Q 1/6886; G01N 33/53; G01N 33/57419
USPC ....................................... 435/6, 7.1, 377, 378
See application file for complete search history.

(56) References Cited

U.S. PATENT DOCUMENTS

| | | |
|---|---|---|
| 6,391,554 B1 | 5/2002 | West et al. |
| 7,115,360 B2 | 10/2006 | Clarke et al. |
| 2007/0099209 A1 | 5/2007 | Clarke et al. |
| 2007/0203083 A1 | 8/2007 | Mootha et al. |

FOREIGN PATENT DOCUMENTS

WO 2002/057430 A2 7/2002

OTHER PUBLICATIONS

International Search Report and Written Opinion issued in PCT/US2009/060285, mailed Dec. 10, 2009.
Asit Panja, "A Novel Method for the Establishment of a Pure Population of Nontransformed Human Intestinal Primary Epithelial Cell (HIPEC) Lines in Long Term Culture," *Laboratory Investigation*, 80(9):1473-1475 (2000).
Sim et al., "A Preliminary Study of Differentially Expressed Genes in Malaysian Colorectal Carcinoma Cases," *Jurnal Biosains*, 17(1):19-37 (2006).
Allegrucci et al., "Differences between human embryonic stem cell lines," *Human Reproduction Update*, published Aug. 26, 2006, p. 1-18.
Mahendra Rao, "Conserved and divergent paths that regulate self-renewal in mouse and human embryonic stem cells," *Developmental Biology*, 275:269-286 (2004).
Abeyta et al., "Unique gene expression signatures of independently-derived human embryonic stem cell lines," *Human Molecular Genetics*, 13(6):601-608 (2004).
Sato et al., "Molecular signature of human embryonic stem cells and its comparison with the mouse," *Developmental Biology*, 260:404-413 (2003).
Supplementary European Search Report issued in European Patent Application No. EP 09820013, mailed Dec. 20, 2011.
Ansamma et al., "Genes expressed in non-transformed human intestinal primary epithelial cell (HIPEC) lines derived from patients with IBD and controls," *Gastroenterology*, 120(5):P695-696 (Supplement 1) (2001).
Ansamma et al., "Construction of an intestinal mucosa-like structure by growing non-transformed human intestinal primary epithelial cells (HIPEC) on a porcine small intestinal submucosa (SIS) derived fiber matrix," *Gastroenterology*, 120(5):320 (Supplement 1) (2001).
Ansari et al., "Comparison of RANTES expression in Crohn's disease and ulcerative colitis: an aid in the differential diagnosis?," *Journal of Clinical Pathology*, 59(10):1066-1072 (2006).
Zhao et al., "Mucosal tissue derived factors (MTDF) from patients with active Crohn's disease (CD) downregulates IL10 receptor expression on normal human intestinal primary epithelial cells (HIPEC)," *Gastroenterology*, 118(4):AGAA1112 (Supplement 2, Part 2) (2000).
Martin et al., "Cytokine regulation of human intestinal primary epithelial cell susceptibility to Fas-mediated apoptosis," *American Journal of Physiology*, 282(1):G92-G104, (2002).

*Primary Examiner* — Shin Lin Chen
(74) *Attorney, Agent, or Firm* — Heslin Rothenberg Farley & Mesiti P.C.; Andrew K. Gonsalves, Esq.

(57) ABSTRACT

The described invention relates to the identification of biomarkers for gastrointestinal diseases and provides methods utilizing the biomarkers for in drug discovery, monitoring of treatment efficacy, and diagnostics. The invention further provides methods for identifying a therapeutic target to treat ulcerative colitis, colorectal cancer, and Crohn's disease.

14 Claims, 15 Drawing Sheets

```
                           SEQUENCE LISTING

<160> NUMBER OF SEQ ID NOS: 57

<210> SEQ ID NO 1
<211> LENGTH: 20
<212> TYPE: DNA
<213> ORGANISM: Unknown
<220> FEATURE:
<223> OTHER INFORMATION: MAMMALIAN

<400> SEQUENCE: 1
atgcctgtga tttgtgggcc                                                     20

<210> SEQ ID NO 2
<211> LENGTH: 24
<212> TYPE: DNA
<213> ORGANISM: Unknown
<220> FEATURE:
<223> OTHER INFORMATION: MAMMALIAN

<400> SEQUENCE: 2
caaccagcag tttgcaggtg gctg                                                24

<210> SEQ ID NO 3
<211> LENGTH: 25
<212> TYPE: DNA
<213> ORGANISM: Unknown
<220> FEATURE:
<223> OTHER INFORMATION: MAMMALIAN

<400> SEQUENCE: 3
catcaaagct ctgcagaaag aactc                                               25

<210> SEQ ID NO 4
<211> LENGTH: 24
<212> TYPE: DNA
<213> ORGANISM: Unknown
<220> FEATURE:
<223> OTHER INFORMATION: MAMMALIAN

<400> SEQUENCE: 4
cgggacacct ggcttcggat ttcg                                                24

<210> SEQ ID NO 5
<211> LENGTH: 23
<212> TYPE: DNA
<213> ORGANISM: Unknown
<220> FEATURE:
<223> OTHER INFORMATION: MAMMALIAN

<400> SEQUENCE: 5
catgagtcag tgaacaggga atg                                                 23

<210> SEQ ID NO 6
<211> LENGTH: 28
<212> TYPE: DNA
<213> ORGANISM: Unknown
<220> FEATURE:
<223> OTHER INFORMATION: MAMMALIAN

<400> SEQUENCE: 6
```

-continued caaaagtctt taccaataat atttagag                                    28

<210> SEQ ID NO 7
<211> LENGTH: 26
<212> TYPE: DNA
<213> ORGANISM: Unknown
<220> FEATURE:
<223> OTHER INFORMATION: MAMMALIAN

<400> SEQUENCE: 7
taaaagttct agtggtacgg taggag                                      26

<210> SEQ ID NO 8
<211> LENGTH: 27
<212> TYPE: DNA
<213> ORGANISM: Unknown
<220> FEATURE:
<223> OTHER INFORMATION: MAMMALIAN

<400> SEQUENCE: 8
cataatagaa tgtctacatt ccttctg                                     27

<210> SEQ ID NO 9
<211> LENGTH: 25
<212> TYPE: DNA
<213> ORGANISM: Unknown
<220> FEATURE:
<223> OTHER INFORMATION: MAMMALIAN

<400> SEQUENCE: 9
gatctgtctt acaacctatt agaag                                       25

<210> SEQ ID NO 10
<211> LENGTH: 24
<212> TYPE: DNA
<213> ORGANISM: Unknown
<220> FEATURE:
<223> OTHER INFORMATION: MAMMALIAN

<400> SEQUENCE: 10
ctgaaaacac atgtagataa tggc                                        24

<210> SEQ ID NO 11
<211> LENGTH: 25
<212> TYPE: DNA
<213> ORGANISM: Unknown
<220> FEATURE:
<223> OTHER INFORMATION: MAMMALIAN

<400> SEQUENCE: 11
gttcttggac taaaagttta ttaag                                       25

<210> SEQ ID NO 12
<211> LENGTH: 24
<212> TYPE: DNA
<213> ORGANISM: Unknown
<220> FEATURE:
<223> OTHER INFORMATION: MAMMALIAN

<400> SEQUENCE: 12
cttatccagc acacgaatac acag                                        24

<210> SEQ ID NO 13
<211> LENGTH: 20
<212> TYPE: DNA
<213> ORGANISM: Unknown

```
<220> FEATURE:
<223> OTHER INFORMATION: MAMMALIAN

<400> SEQUENCE: 13
tggatacgtt tccttataag                                              20

<210> SEQ ID NO 14
<211> LENGTH: 24
<212> TYPE: DNA
<213> ORGANISM: Unknown
<220> FEATURE:
<223> OTHER INFORMATION: MAMMALIAN

<400> SEQUENCE: 14
ttggactcat atcaagatgc tctg                                         24

<210> SEQ ID NO 15
<211> LENGTH: 24
<212> TYPE: DNA
<213> ORGANISM: Unknown
<220> FEATURE:
<223> OTHER INFORMATION: MAMMALIAN

<400> SEQUENCE: 15
atgcttttcc cgaattatcc tacg                                         24

<210> SEQ ID NO 16
<211> LENGTH: 24
<212> TYPE: DNA
<213> ORGANISM: Unknown
<220> FEATURE:
<223> OTHER INFORMATION: MAMMALIAN

<400> SEQUENCE: 16
ctccaggacc gcccgccatg gctg                                         24

<210> SEQ ID NO 17
<211> LENGTH: 24
<212> TYPE: DNA
<213> ORGANISM: Unknown
<220> FEATURE:
<223> OTHER INFORMATION: MAMMALIAN

<400> SEQUENCE: 17
ctgtgtgtaa acatgacttc caag                                         24

<210> SEQ ID NO 18
<211> LENGTH: 24
<212> TYPE: DNA
<213> ORGANISM: Unknown
<220> FEATURE:
<223> OTHER INFORMATION: MAMMALIAN

<400> SEQUENCE: 18
cagcaaccat gagtacaaat ggtg                                         24

<210> SEQ ID NO 19
<211> LENGTH: 24
<212> TYPE: DNA
<213> ORGANISM: Unknown
<220> FEATURE:
<223> OTHER INFORMATION: MAMMALIAN

<400> SEQUENCE: 19
gaaattgtca atacaaatgc tcag                                         24
```

```
<210> SEQ ID NO 20
<211> LENGTH: 23
<212> TYPE: DNA
<213> ORGANISM: Unknown
<220> FEATURE:
<223> OTHER INFORMATION: MAMMALIAN

<400> SEQUENCE: 20
cctgcaacca cactgtgatg gcc                                              23

<210> SEQ ID NO 21
<211> LENGTH: 23
<212> TYPE: DNA
<213> ORGANISM: Unknown
<220> FEATURE:
<223> OTHER INFORMATION: MAMMALIAN

<400> SEQUENCE: 21
ccaagtggtt tccaaggtgt gag                                              23

<210> SEQ ID NO 22
<211> LENGTH: 23
<212> TYPE: DNA
<213> ORGANISM: Unknown
<220> FEATURE:
<223> OTHER INFORMATION: MAMMALIAN

<400> SEQUENCE: 22
cagaggatta tgcaggtccc tgc                                              23

<210> SEQ ID NO 23
<211> LENGTH: 23
<212> TYPE: DNA
<213> ORGANISM: Unknown
<220> FEATURE:
<223> OTHER INFORMATION: MAMMALIAN

<400> SEQUENCE: 23
gcaagctttc atcaagcctt ctc                                              23

<210> SEQ ID NO 24
<211> LENGTH: 24
<212> TYPE: DNA
<213> ORGANISM: Unknown
<220> FEATURE:
<223> OTHER INFORMATION: MAMMALIAN

<400> SEQUENCE: 24
cttgttgtac acatcaaggc atgc                                             24

<210> SEQ ID NO 25
<211> LENGTH: 24
<212> TYPE: DNA
<213> ORGANISM: Unknown
<220> FEATURE:
<223> OTHER INFORMATION: MAMMALIAN

<400> SEQUENCE: 25
ccatatggct tgaacgagca gccg                                             24

<210> SEQ ID NO 26
<211> LENGTH: 23
<212> TYPE: DNA
<213> ORGANISM: Unknown
<220> FEATURE:
<223> OTHER INFORMATION: MAMMALIAN
```

```
<400> SEQUENCE: 26
caagcagatg aagatgtacc gag                                              23

<210> SEQ ID NO 27
<211> LENGTH: 24
<212> TYPE: DNA
<213> ORGANISM: Unknown
<220> FEATURE:
<223> OTHER INFORMATION: MAMMALIAN

<400> SEQUENCE: 27
gaggagtatg tgaattcttt ggag                                             24

<210> SEQ ID NO 28
<211> LENGTH: 23
<212> TYPE: DNA
<213> ORGANISM: Unknown
<220> FEATURE:
<223> OTHER INFORMATION: MAMMALIAN

<400> SEQUENCE: 28
caccctcatg gccaagcgca ttg                                              23

<210> SEQ ID NO 29
<211> LENGTH: 25
<212> TYPE: DNA
<213> ORGANISM: Unknown
<220> FEATURE:
<223> OTHER INFORMATION: MAMMALIAN

<400> SEQUENCE: 29
ctcatcttca cacgtcttca ggttg                                            25

<210> SEQ ID NO 30
<211> LENGTH: 26
<212> TYPE: DNA
<213> ORGANISM: Unknown
<220> FEATURE:
<223> OTHER INFORMATION: MAMMALIAN

<400> SEQUENCE: 30
gaaccctcac ttgcatttgg acagag                                           26

<210> SEQ ID NO 31
<211> LENGTH: 25
<212> TYPE: DNA
<213> ORGANISM: Unknown
<220> FEATURE:
<223> OTHER INFORMATION: MAMMALIAN

<400> SEQUENCE: 31
ctgcttgatc gcttgcccct ctggc                                            25

<210> SEQ ID NO 32
<211> LENGTH: 24
<212> TYPE: DNA
<213> ORGANISM: Unknown
<220> FEATURE:
<223> OTHER INFORMATION: MAMMALIAN

<400> SEQUENCE: 32
cttgtaagaa cataaacaca ccag                                             24

<210> SEQ ID NO 33
```

```
<211> LENGTH: 24
<212> TYPE: DNA
<213> ORGANISM: Unknown
<220> FEATURE:
<223> OTHER INFORMATION: MAMMALIAN

<400> SEQUENCE: 33
ggtttctgct ttgcatatct cctg                                              24

<210> SEQ ID NO 34
<211> LENGTH: 26
<212> TYPE: DNA
<213> ORGANISM: Unknown
<220> FEATURE:
<223> OTHER INFORMATION: MAMMALIAN

<400> SEQUENCE: 34
gccgaatctt ttaaaataca actacg                                            26

<210> SEQ ID NO 35
<211> LENGTH: 26
<212> TYPE: DNA
<213> ORGANISM: Unknown
<220> FEATURE:
<223> OTHER INFORMATION: MAMMALIAN

<400> SEQUENCE: 35
gccgaatctt ttaaaataca actacg                                            26

<210> SEQ ID NO 36
<211> LENGTH: 24
<212> TYPE: DNA
<213> ORGANISM: Unknown
<220> FEATURE:
<223> OTHER INFORMATION: MAMMALIAN

<400> SEQUENCE: 36
ggaagtggac cattccttct ccag                                              24

<210> SEQ ID NO 37
<211> LENGTH: 25
<212> TYPE: DNA
<213> ORGANISM: Unknown
<220> FEATURE:
<223> OTHER INFORMATION: MAMMALIAN

<400> SEQUENCE: 37
cttcaaggtc acgttcatct tgagc                                             25

<210> SEQ ID NO 38
<211> LENGTH: 24
<212> TYPE: DNA
<213> ORGANISM: Unknown
<220> FEATURE:
<223> OTHER INFORMATION: MAMMALIAN

<400> SEQUENCE: 38
ctggaggctt agggaccaag gctg                                              24

<210> SEQ ID NO 39
<211> LENGTH: 25
<212> TYPE: DNA
<213> ORGANISM: Unknown
<220> FEATURE:
<223> OTHER INFORMATION: MAMMALIAN

<400> SEQUENCE: 39
```

```
gtgataactg ctaggaatgg agtac                                              25

<210> SEQ ID NO 40
<211> LENGTH: 20
<212> TYPE: DNA
<213> ORGANISM: Unknown
<220> FEATURE:
<223> OTHER INFORMATION: MAMMALIAN

<400> SEQUENCE: 40
ttgaagttct ccagctcctg                                                    20

<210> SEQ ID NO 41
<211> LENGTH: 19
<212> TYPE: DNA
<213> ORGANISM: Unknown
<220> FEATURE:
<223> OTHER INFORMATION: MAMMALIAN

<400> SEQUENCE: 41
gaaatggagg caccccttc                                                     19

<210> SEQ ID NO 42
<211> LENGTH: 25
<212> TYPE: DNA
<213> ORGANISM: Unknown
<220> FEATURE:
<223> OTHER INFORMATION: MAMMALIAN

<400> SEQUENCE: 42
tcagaatttg tagactttct gtctc                                              25

<210> SEQ ID NO 43
<211> LENGTH: 24
<212> TYPE: DNA
<213> ORGANISM: Unknown
<220> FEATURE:
<223> OTHER INFORMATION: MAMMALIAN

<400> SEQUENCE: 43
caaccatcat gacctctgaa tatg                                               24

<210> SEQ ID NO 44
<211> LENGTH: 25
<212> TYPE: DNA
<213> ORGANISM: Unknown
<220> FEATURE:
<223> OTHER INFORMATION: MAMMALIAN

<400> SEQUENCE: 44
gttccagttg ccggatcatc tcctg                                              25

<210> SEQ ID NO 45
<211> LENGTH: 27
<212> TYPE: DNA
<213> ORGANISM: Unknown
<220> FEATURE:
<223> OTHER INFORMATION: MAMMALIAN

<400> SEQUENCE: 45
gaattttttt atgaattctc agccctc                                            27

<210> SEQ ID NO 46
<211> LENGTH: 24
<212> TYPE: DNA
```

```
<213> ORGANISM: Unknown
<220> FEATURE:
<223> OTHER INFORMATION: MAMMALIAN

<400> SEQUENCE: 46 cacctttttca aagcaggcct tggc                                              24

<210> SEQ ID NO 47
<211> LENGTH: 24
<212> TYPE: DNA
<213> ORGANISM: Unknown
<220> FEATURE:
<223> OTHER INFORMATION: MAMMALIAN

<400> SEQUENCE: 47
cagaggctca gaacaacccg acag                                               24

<210> SEQ ID NO 48
<211> LENGTH: 24
<212> TYPE: DNA
<213> ORGANISM: Unknown
<220> FEATURE:
<223> OTHER INFORMATION: MAMMALIAN

<400> SEQUENCE: 48
cttccaagat gtgccagctt cctg                                               24

<210> SEQ ID NO 49
<211> LENGTH: 25
<212> TYPE: DNA
<213> ORGANISM: Unknown
<220> FEATURE:
<223> OTHER INFORMATION: MAMMALIAN

<400> SEQUENCE: 49
cttccactgg tagatctgaa acatc                                              25

<210> SEQ ID NO 50
<211> LENGTH: 23
<212> TYPE: DNA
<213> ORGANISM: Unknown
<220> FEATURE:
<223> OTHER INFORMATION: MAMMALIAN

<400> SEQUENCE: 50
cagctcctgc cccagcacaa gtg                                                23

<210> SEQ ID NO 51
<211> LENGTH: 23
<212> TYPE: DNA
<213> ORGANISM: Unknown
<220> FEATURE:
<223> OTHER INFORMATION: MAMMALIAN

<400> SEQUENCE: 51
gataagagtt gttctccatc aag                                                23

<210> SEQ ID NO 52
<211> LENGTH: 23
<212> TYPE: DNA
<213> ORGANISM: Unknown
<220> FEATURE:
<223> OTHER INFORMATION: MAMMALIAN

<400> SEQUENCE: 52
ggcagatatt ggttgaacat ctg                                                23
```

```
<210> SEQ ID NO 53
<211> LENGTH: 24
<212> TYPE: DNA
<213> ORGANISM: Unknown
<220> FEATURE:
<223> OTHER INFORMATION: MAMMALIAN

<400> SEQUENCE: 53
ctcatctcca cagtatcttc ccac                                          24

<210> SEQ ID NO 54
<211> LENGTH: 25
<212> TYPE: DNA
<213> ORGANISM: Unknown
<220> FEATURE:
<223> OTHER INFORMATION: MAMMALIAN

<400> SEQUENCE: 54
gttcccaata aaccccatat gacag                                         25

<210> SEQ ID NO 55
<211> LENGTH: 25
<212> TYPE: DNA
<213> ORGANISM: Unknown
<220> FEATURE:
<223> OTHER INFORMATION: MAMMALIAN

<400> SEQUENCE: 55
catgtgccag gcactgttct aggtg                                         25

<210> SEQ ID NO 56
<211> LENGTH: 25
<212> TYPE: DNA
<213> ORGANISM: Unknown
<220> FEATURE:
<223> OTHER INFORMATION: MAMMALIAN

<400> SEQUENCE: 56
gactctggat gtaggaatcc tgctc                                         25

<210> SEQ ID NO 57
<211> LENGTH: 20
<212> TYPE: DNA
<213> ORGANISM: Unknown
<220> FEATURE:
<223> OTHER INFORMATION: MAMMALIAN

<400> SEQUENCE: 57
tttttttttt tttttttttt                                               20
```

USE AND IDENTIFICATION OF BIOMARKERS FOR GASTROINTESTINAL DISEASES

CROSS REFERENCES

This application is a continuation of U.S. patent application Ser. No. 12/577,141, filed Oct. 9, 2009, which claims the benefit of priority to U.S. provisional application 61/195,646, filed Oct. 9, 2008, the disclosures of which are incorporated in their entirety herein by reference.

FIELD OF THE INVENTION

The present invention relates to the identification of biomarkers for gastrointestinal diseases and further provides methods utilizing such biomarkers in drug discovery, the monitoring of treatment efficacy, and diagnostics.

BACKGROUND OF THE INVENTION

Components of the Human Gastrointestinal Tract

The gastrointestinal tract is a continuous tube that extends from the mouth to the anus. On a gross level, the gastrointestinal tract is composed of the following organs: the mouth, most of the pharynx, the esophagus, the stomach, the small intestine (duodenum, jejunum and ileum), and the large intestine (cecum including the appendix, colon and rectum) (Tortora, G. J., et al., *Principles of Anatomy and Physiology*, Wiley & Sons, Inc. Hoboken, N.J. 2006). Each segment of the gastrointestinal tract participates in the absorptive processes essential to digestion by producing chemical substances that facilitate digestion of foods, liquids, and other substances, such as therapeutic agents, taken orally.

Within the gastrointestinal tract, the small intestine is the site of most digestion and absorption and is structured specifically for these important functions. The small intestine is divided into three segments: the duodenum, the jejunum, and the ileum. The absorptive cells of the small intestine produce several digestive enzymes known as 'brush-border' enzymes. The brush-border enzymes, together with pancreatic and intestinal juices, facilitate the absorption of substances from the chime in the small intestine. The large intestine is the terminal portion of the gastrointestinal tract and contributes to the completion of absorption, the production of certain vitamins, and the formation and expulsion of feces.

The epithelium is a purely cellular avascular tissue layer that covers all free surfaces (cutaneous, mucous, and serous) of the body, including the glands and other structures derived from it. The epithelium lines both the exterior of the body, as skin, the interior cavities, and lumen of the body. The outermost layer of human skin is composed of dead stratified squamous, keratinized epithelial cells. The mucous membranes lining the inside of the mouth, the esophagus, and parts of the rectum are lined by nonkeratinized stratified squamous epithelium. Epithelial cell lines also are present inside of the lungs, the gastrointestinal tract, and the reproductive and urinary tracts, and form the exocrine and endrocrine glands.

Epithelial cells are involved in secretion, absorption, protection, transcellular transport, sensation detection and selective permeability. There are variations in the cellular structures and functions in the epithelium throughout the gastrointestinal tract. The epithelium in the mouth, pharynx, esophagus and anal canal is mainly a protective, nonkeratinized, squamous epithelium that has a protective role against abrasion and wear-and-tear from mechanical movements of food particles that are chewed and swallowed (mouth, pharynx, and esophagus) or undigested/unabsorbed substances eliminated by defecation (anal canal). The epithelium of the stomach is composed of several kinds of cells. Columnar cells, present in a single layer, participate minimally in absorption and secretion. Goblet cells produce mucus and participate in protective and mechanical functions. Enteroendocrine cells participate in the secretion of gastrointestinal hormones. Additionally, the columnar epithelial lining of the stomach has millions of gastric pits, which lead to gastric glands. Various types of specialized epithelial cells located in these gastric glands produce gastric juice that contains pepsin (an enzyme produced by Chief cells and needed for protein digestion), intrinsic factor (needed for absorption of vitamin B12) and hydrochloric acid to decontaminate food and activate pepsin) produced by Parietal cells, plus mucus (produced by surface mucous cells and mucous neck cells) in the stomach. Simple columnar epithelia, with microvilli, line the lumen to facilitate the role of the small intestine as the primary absorptive organ in the body; as the absorptive function of the large intestine is not as great as that of the small intestine, microvilli are not present in epithelia of the large intestine. Within the large intestine, protective mucus is produced in copious amounts and goblet cells are abundant. The epithelial lining provides an important defense barrier against microbial pathogens throughout the GI tract.

The development of intestinal epithelium involves three major phases: 1) an early phase of epithelial proliferation and morphogenesis; 2) an intermediate period of cellular differentiation in which the distinctive cell types characteristic of intestinal epithelium appear; and 3) a final phase of biochemical and functional maturation (Mathan, M. P., et al. *Am. J. Anat.* 146(1):73-92. 1976; Hirano, S, and Kataoka, K. *Arch. Histol. Jpn.* 49(3):333-48. 1986; Bjerknes, M. and Cheng, H. *Am. J. Physiol. Gastrointest. Liver Physiol.* 283(3):G767-77. 2002; Brittan, M. and Wright, N. A. *J. Pathol.* 197(4):492-5. 2002; Potten, C. et al. *Cell Prolif.* 36(3):115-29. 2003; Sancho, E., et al. *Curr. Opin. Cell. Biol.* 15(6):763-70. 2003; Stappenbeck, T., et al. *Proc. Natl. Acad. Sci. USA.* 100(3): 1004-9. 2003).

Intestinal crypts, located at the base of villi, contain stem cells (Burgess, D., et al. *J. Cell Biol.* 109(5):2139-44. 1989; Weiser, M., et al., *Immunol. Invest.* 18(1-4):417-30. 1989; Bjerknes, M. and Cheng, H. *Gastroenterol.* 116(1):7-14. 1999; Brittan, M. and Wright, N. A. *J. Pathol.* 197(4):492-5. 2002), which supply the entire epithelial cell surface with a variety of epithelial cell subtypes (Brink, G. R., et al., *Science*, 294:2115. 2001; Burgess, D., et al. *J. Cell Biol.* 109(5):2139-44. 1989; Weiser, M., et al., *Immunol. Invest.* 18(1-4):417-30. 1989; Quaroni, A. and Beaulieu, *J. Gastroenterol.*, 113(4): 1198-213. 1997). These specialized cells provide for an external environment-internal environment interface, ion and fluid secretion and reabsorption (Sanderson, I., et al., *Gut.* 38(6): 853-8. 1996), antigen recognition (Hoyne, G., et al. *Immunol.* 80(2):204-8. 1993; Neutra, M., and Kraehenbuhl, J. *Am. J. Trop. Med. Hyg.* 50(5 Suppl.):10-3. 1994; Balimane, P., et al. *J. Pharmacol. Toxicol. Methods.* 44(1):301-12. 2000), hormone secretion (Schuerer-Maly, C., et al. *Immunol.* 81(1):85-91. 1994; Panja, A., et al. *Clin Exp Immunol* 100(2):298-305. 1995), and surface protection (Flemstrom, G. and Garner, A. *Ciba Found Symp.* 109:94-108. 1984; Schuerer-Maly, C., et al. *Immunol.* 81(1):85-91. 1994; Kindon, H., et al. *Gastroenterol.* 109(2):516-23. 1995; Panja, A., et al. *Clin Exp Immunol* 100(2):298-305. 1995; Podolsky, D. K. *Gastroenterol.* 32(1): 122-6. 1997).

The epithelium forms upon stem cell differentiation (Brittan, M., and Wright, N. A. *Gut*. 53:899-910. 2004) within the intestinal tract. Stem cells are undifferentiated cells having high proliferative potential with the ability to self-renew. Stem cells may generate daughter cells that may undergo terminal differentiation into more than one distinct cell type (Morrison, S., et al. *Cell* 88(3):287-981997. 1997). Pluripotent (a cell that is able to differentiate into many cell types) stem cells undergo further specialization into multipotent progenitor cells that then give rise to functional cells. For example, hematopoietic stem cells give rise to red blood cells, white blood cells, and platelets. Mesenchymal stem cells are multipotent cells that are capable of differentiating along several lineage pathways, including, but not limited to, chondrocytes, osteoblasts, adipocytes, fibroblasts, marrow stroma, and other tissues of mesenchymal origin. Epithelial stem cells give rise to the various types of skin cells; and muscle satellite cells contribute to differentiated muscle tissue. The technologies for retrieval, and maintenance of such cells in an undifferentiated state, of stem cells and growing them in vitro have been the subject of study.

Molecular Markers of Gastrointestinal Epithelial Stem Cells

The surfaces of all cells in the body are coated with specialized protein receptors that have the capability to selectively bind or adhere to other signaling molecules (Weiss and Littman Cell 76.263-74.1994). These receptors and the molecules that bind to them are used for communicating with other cells and for carrying out proper cell functions in the body. Each cell type has a certain combination of receptors, or markers, on their surface that makes them distinguishable from other kinds of cells.

Stem cell markers are given short-hand names based on the molecules that bind to the corresponding stem cell surface receptors. A combination of multiple markers frequently is used to identify a particular stem cell type. Researchers often identify stem cells in shorthand by a combination of marker names reflecting the marker's presence (+) or absence (−). For example, a special type of hematopoietic stem cell from blood and bone marrow called "side population" (or "SP") is described as (CD34−/low, c-Kit+, Sca−1+).

The following markers commonly are used by skilled artisans to identify stem cells and to characterize differentiated cell types (see http://stemcells.nih.gov/info/scireport/appendixE.asp; visited Dec. 28, 2007):

| Marker | Cell Type | Notes |
|---|---|---|
| CD34 | Hematopoietic stem cell (HSC), muscle satellite, endothelial progenitor | a highly glycosylated type I transmembrane protein expressed on 1-4% of bone marrow cells |
| CD38 | immature T and B cells | a type II transmembrane protein found on immature T and B cells but not most mature peripheral lymphocytes |
| CD41 | platelets and megakaryocytes | the integrin αIIb subunit |
| CD45 | WBC progenitor | the leukocyte common antigen found on all cells of hematopoietic origin |
| CD105 | Endothelial cells | a disulfide-linked homodimer found on endothelial cells but absent from most T and B cells |
| CD133 | primitive hematopoietic progenitors | a pentaspan transmembrane glycoprotein |
| CD3 | T cells | a member of the T cell receptor complex |
| CD4, CD8 | Mature T cells | Cell-surface protein markers specific for mature T lymphocyte (WBC subtype) |
| CD7 | Early T cells | An early T cell lineage marker |
| CD10 | early T and B cell precursors | a type II membrane metalloprotease |
| CD13 | granulocytes, monocytes and their precursors | a type II membrane metalloprotease |
| CD14 | myelomonocytic lineage | a GPI-linked protein expressed mainly on myelomonocytic lineage cells |
| CD19 | B cells | a component of the B cell antigen signaling complex |
| CD33 | Myelomonocytic precursors | a sialic acid binding protein absent from pluripotent stem cells that appears on myelomonocytic precursors after CD34 |
| CD38 | WBC lineages | A Cell-surface molecule that identifies WBC lineages. Selection of CD34+/CD38− cells allows for purification of HSC populations |
| CD44 | Mesenchymal | A type of cell-adhesion molecule used to identify specific types of mesenchymal cells |
| CD56 | NK cells | an isoform of the neural adhesion molecule found exclusively on natural killer (NK) cells; |
| CD127 | lymphocytes | the high affinity interleukin 7 receptor expressed on lymphocytes |
| CD138 | Immature B cells and plasma cells | an extracellular matrix receptor found on immature B cells and plasma cells |
| Glycophorin A | RBCs, embryoid precursors | a sialoprotein present on human RBCs and embryoid precursors |
| CD90 | prothymocytes | a GPI-cell anchored molecule found on prothymocyte cells in humans- |

-continued

| Marker | Cell Type | Notes |
| --- | --- | --- |
| c-kit | HSC, MSC | Cell-surface receptor on BM cell types that identifies HSC and MSC; binding by fetal calf serum (FCS) enhances proliferation of ES cells, HSCs, MSCs, and hematopoietic progenitor cells |
| Fetal liver kinase-1 (Flk-1) | endothelial | Cell-surface receptor protein that identifies endothelial cell progenitor; marker of cell-cell contacts |

There are no universally accepted molecular markers that identify gastrointestinal stem cells. However, several markers have been used to identify stem cells in small and large intestinal tissues. These include: β-1-integrin (Jones, R., et al. *J Cell Biol* 175(3):505-14. 2006), mushashi-1 (Booth, C. and Potten, C. *J Clin Invest* 105(11):1493-9. 2000; Potten, C., et al. *Differentiation* 71(1):28-41. 2003; Yen, T. and Wright, N. *Stem Cell Rev* 2(3):203-12. 2006), CD45 (Dekaney, C., et al. *Gastroenterology* 129(5):1567-80. 2005; Lynch, L., et al. *J Immunol* 176(9):5199-204. 2006), and cytokeratin (Raju, G. *Ann Acad Med Singapore* 18(3):298-301. 1989).

CD45 (also called the common leukocyte antigen, T220 and B220 in mice), is a transmembrane protein with cytoplasmic protein tyrosine phosphatase (PTP) activity. CD45 is found in hematopoietic cells except erythrocytes and platelets. It has several isoforms that can be seen in the various stages of differentiation of normal hematopoietic cells (Greaves, M., et al. *Blood* 61(4):628-39. 1983; Alt, F., et al. *Immunol Rev* 89:5-30. 1986; Thomas, M. L. *Ann. Rev Immunol* 7:339-69. 1989; Weiss, A. and Littman, D. *Cell* 76(2): 263-74. 1994).

Mushashi-1 is an early developmental antigenic marker of stem cells and glial/neuronal cell precursor cells (Jones, P., et al. *Cell* 80(1):83-93. 1995; Kayahara, T., et al. *FEBS Lett* 535(1-3):131-5. 2003; Potten, C., et al. *Differentiation* 71(1): 28-41. 2003; Asai, R., et al. *Dev Growth Differ* 47(8):501-10. 2005).

β-1-integrin (CD29, fibronectin receptor), is a β-subunit of a heterodimer protein member of the integrin family of proteins that are membrane receptors involved in cell adhesion and recognition (Pytela, R., et al. (1985). Cell 40(1):191-8. 1985; Fujimoto, K., et al. *Gastroenterol.* 123(6):1941-8. 2002; Shackleton, M., et al. *Nature* 439(7072):84-8. 2006).

Cytokeratins are intermediate filament proteins found in the intracytoplasmic cytoskeleton of the cells that comprise epithelial tissue. Over twenty different cytokeratin polypeptides have been identified (Franke, W., et al. *Differentiation* 15(1):7-25. 1979; Steinert, P., et al. *Cell* 42(2):411-20. 1985).

There are four main epithelial cell lineages in the gastrointestinal tract: columnar epithelial cells, goblet cells, enteroendocrine chromaffin cells, and Paneth cells. Several molecular markers have been used to identify these cells (Simon, T. and Gordon, J. *Curr Opin Genet Dev* 5(5):577-86. 1995).

The markers used to identify columnar epithelial cells include: intestinal alkaline phosphatase (ALP1), sucrase isomaltase (SI), sodium/glucose cotransporter (SLGT1), dipeptidyl-peptidase 4 (DPP4), and CD26. Intestinal alkaline phosphatase (E.C. 3.1.3.1) is a membrane-bound enzyme localized in the brush border of enterocytes in the human intestinal epithelium. Sucrase-isomaltase (SI, EC 3.2.1.48) is an enterocyte-specific small intestine brush-border membrane disaccharidase. Dipeptidyl-peptidase 4 (E.C. 3.4.14.5) is a membrane bound serine-type peptidase. Sodium/glucose transporter (SGLT) mediates transport of glucose into epithelial cells. SGLT belongs to the sodium/glucose cotransporter family SLCA5. Two different SGLT isoforms, SGLT1 and SGLT2, have been identified to mediate renal tubular glucose reabsorption in humans. Both of them are characterized by their different substrate affinity (Panayotova-Heiermann et al. J Biol Chem 271.10029-34.1996). SGLT1 transports glucose as well as galactose, and is expressed both in the kidney and in the intestine. CD26 is a multifunctional protein of 110 KDa strongly expressed on epithelial cells (kidney proximal tubules, intestine, and bile duct) and on several types of endothelial cells and fibroblasts and on leukocyte subsets (Kikkawa et al. Biochim Biophys Acta 1751.45-51.2005; Tokunaga et al. J Histochem Cytochem 55.735-44.2007).

The markers used to identify goblet cells include mucin 2 (MUC2) and trefoil factor 3 (TFF3) (Bergstrom et al. Infect Immun 76.796-811.2008). Mucin-2, a secreted gel-forming mucin, is the major gel-forming mucin secreted by goblet cells of the small and large intestines and the main structural component of the mucus gel. Intestinal trefoil factor 3 is a nonmucin protein and a product of fully differentiated goblet cells (Chinery, R., et al. *Genomics* 32(2):281-4. 1996; Ogata, Inoue et al. 1998; Itoh, H., et al. *Biochem J* 341 (Pt 2):461-72. 1999; Yamachika, T., et al. *Clin Cancer Res* 8(5):1092-9. 2002; Bergstrom, K, et al. (2008). *Infect Immun* 76(2):796-811. 2008).

The markers used to identify enteroendocrine chromaffin cells include chromogranin A (CHGA) (Ho, S., et al. *Gastroenterol.* 97(2):392-404. 1989; Wimley, W., et al. *Protein Sci* 3(9):1362-73. 1994; Moller, P., et al. *Am J Pathol* 149(1):9-13. 1996; Ouellette, A. J. and Selsted, M. *Faseb J* 10(11): 1280-9. 1996; Taupin, D., et al. *Lab Invest* 75(1):25-32. 1996; Turner, J. R. and Odze, R. (1996). *Hum Pathol* 27(1):63-9. 1996; Ronnblom, A., et al. *J Intern Med* 245(4):91-7 1999; Wong, W., et al. (2000). *J Pathol* 190(1):107-13. 2000; Andersson, N., et al. *Biochem Biophys Res Commun* 332(2):404-10. 2005; Stewart, C. and Hillery, S. *J Clin Pathol* 60(11):1284-9. 2007) and synaptophysin (SYP) (Andersson, N., et al. *Biochem Biophys Res Commun* 332(2):404-10. 2005). Chromogranin A (CHGA) and its derived peptides, which are stored and released from dense-core secretory granules of neuroendocrine cells, have been implicated as playing multiple roles in the endocrine, cardiovascular, and nervous systems. Synaptophysin I (SYP) is a synaptic vesicle membrane protein that is ubiquitously expressed throughout the brain without a definite synaptic function.

The markers used to identify Paneth cells include lysozyme, defensin, and matrix metallopeptidase 7 (MMP7) (Ho, S., et al. *Gastroenterol.* 97(2):392-404. 1989). Lysozyme (LYZ or muramidase) (E.C. 3.2.1.17) catalyzes the hydrolysis of 1,4-beta-linkages between N-acetylmuramic acid and N-acetyl-D-glucosamine residues in a peptidoglycan and between N-acetyl-D-glucosamine residues in chitodextrins. Defensins (DEFA1) are small peptides that are produced by leukocytes and epithelial cells. Human defensin α-1 is a 3.5-kDa, 30-amino-acid peptide that has shown effector functions in host innate immunity against some microorganisms (Semenza, G. Ann. *Rev Cell Biol* 2:255-313. 1986; Wimley, W., et al. *Protein Sci* 3(9):1362-73. 1994; Moller, P., et al. *Am J Pathol* 149(1):9-13. 1996; Ouellette, A. and Selsted, M. *Faseb J* 10(11):1280-9. 1996; Taupin, D., et al. *Lab Invest* 75(1):25-32. 1996; Turner, J. and Odze, R. *Hum Pathol* 27(1): 63-9. 1996). Matrix metalloproteinases (MMPs) are an important family of metal-dependant enzymes that are responsible for the degradation of extracellular matrix components. MMPs are involved in various physiologic processes including embryogenesis and tissue remodeling. They also play a key role in invasion and metastasis of tumor cells, which require proteolysis of basal membranes and extracellular matrix (Ayabe, T., et al. *J Biol Chem* 277(7):5219-28. 2002; Satchell, D., et al. (2003). *J Biol Chem* 278(16):13838-46. 2003; Weeks, C., et al. *J Biol Chem* 281(39):28932-42. 2006).

The epithelial cells on the surfaces of the intestinal lumen are subjected to a wide range of assaults including microbial, chemical, and physical forces (Savage, D.C. *Am J Clin Nutr* 25(12):1372-9. 1972; Keren, D. F. *Am J Surg Pathol.* 12 Suppl 1:100-5. 1988; Ouellette, A. J. and M. E. Selsted. *Faseb J.* 10(11):1280-9. 1996; Neutra, M. R. *Am J Physiol.* 274(5 Pt 1): G785-91. 1998; Owen, R. L. *Semin Immunol* 11(3):157-63. 1999; Neutra, M. R., et al. *Nat Immunol* 2(11):1004-9. 2001; Otte, J. M. and Podolsky, D. *Am J Physiol Gastrointest Liver Physiol* 286(4):G613-26. 2004); thus they also may contribute to patho-physiologic impairment in diseases. Additionally, these cells are targets for inflammation, infection, and malignant transformation.

Biomarkers for Pathogenesis

Several biomarkers have been utilized as potential indicators for pathogenic processes.

SCYA (small inducible cytokine subfamily) 16 and 20 (or CCL 16 and 20) are members of a family of cytokines characterized by two adjacent cysteines (C—C) involved in immunoregulatory and inflammatory processes. They display chemotactic activity for lymphocytes and monocytes but not for neutrophils (Hieshima et al. J Biol Chem 272.5846-53.1997). CCL16 has been reported to be up-regulated selectively by IL-10 in inflammatory cell recruitment and cytokine and chemokine production during ulcerative colitis (Pannellini et al. Int J Immunopathol Pharmacol 17.171-80.2004). This chemokine significantly enhances the effector and the antigen-presenting function of macrophages and augments the cytolytic activity T cell which in turn activate caspase-8 via overexpression of TNF-alpha and Fas ligand in tumor target cells (Cappello et al. J Leukoc Biol 75.135-42.2004). Intratumoral injection of adenoviral vectors expressing CCL16 prevented metastatic spread and cured 63% of mice bearing the 4T1 mammary adenocarcinoma, a model of spontaneous metastasis (Guiducci et al. J Immunol 172.4026-36.2004). CCL20 expression in intestinal epithelial-type cells is induced by proinflammatory cytokines such as IL-1 and TNF-alpha primarily through activation of NF-kappaB (Fujiie et al. Int Immunol 13.1255-63.2001).

Retinoids, which have roles in the modulation of cell growth, differentiation, and apoptosis, are mediated by nuclear retinoic acid receptors (RARs) and retinoid X receptors (RXRs) ((Clifford et al. EMBO J. 15.4142-55.1996)). Altered expression of nuclear retinoid receptors is associated with the malignant transformation of human cells (Zhao et al. Exp Cell Res 219.555-61.1995). RAR beta is the best-studied RAR subtype in the biology of retinoid effects on carcinogenesis and is the receptor subtype whose expression is frequently most decreased in lung cancer. Three different isoforms of this receptor have been reported in humans: beta1, beta2 and beta4 (Zelent et al. EMBO J. 10.71-81.1991). Close investigation of the importance of the distinct functions of these isoforms in the pathogenesis of cancer identifies Beta 1 and 2 as tumor suppressors (Petty et al. J Natl Cancer Inst 97.1645-51.2005), (Soprano and Soprano J Nutr 132.3809S-13S.2002). Isoform beta1 is a fetal isoform not generally detected in normal tissues of adult humans, although it is expressed in small-cell lung cancer (Houle et al. Cancer Res 54.365-9.1994). Loss of expression of RARbeta2 is associated with esophageal squamous cell carcinomas (Ralhan et al. Int J Cancer 118.1077-89.2006), cerebral glioma (Klein et al. Neurochirurgie 51.147-54.2005), and epidermoid lung cancer ((Houle, Rochette-Egly and Bradley Proc Natl Acad Sci USA 90.985-9.1993). It's inactivation by hypermethylation is reported in oral premalignant lesions, head and neck squamous cell carcinomas (HNSCCs) and in human colon cancer (Youssef et al. Clin Cancer Res 10.1733-42.2004).

NCAM (neural cell adhesion molecule) is an epithelial cell adhesion molecule that is found in normal colon epithelium as well as in colon tumors. Roesler et al reported that this adhesion molecule was present more often in colon cancers with a more benign course compared to clinically aggressive tumors of the colon, leading to the conclusion that this molecule might serve as a tumor suppressor in colon carcinoma (Roesler et al. Am J Surg 174.251-7.1997).

The tissue inhibitor of metalloproteinase (TIMP) gene encodes an extracellular matrix protein. It has been shown to increase cell death and growth inhibition (via delaying the G1 phase), and thus is presumed to be involved in tumor suppression (Wang et al. Cancer 112.1325-36.2008; Smith et al. Cytokine 9.770-80.1997). It originally was reported in several human cell lines including CaCo-2, a colon adenocarcinoma cell line. ((Kishnani et al. Matrix Biol 14.479-88.1995). Lee et al have demonstrated greater hypermethylation of TIMP3 in colon carcinoma compared to normal colon mucosa and adenomas (Lee et al. Lab Invest 84.884-93.2004), although a subsequent study by Xu et al showed no change in the methylation of this gene (Xu et al. World J Gastroenterol 10.3441-54.2004).

The small GTP-binding proteins of Rab family have more than 30 proteins that play important roles at defined steps of vesicular transport in protein secretion and the endocytosis pathway. Rab33B is a Golgi-specific rab protein; it plays a role in the recycling of glycosyltransferases from the Golgi to the ER. (Valsdottir et al. FEBS Lett 508.201-9.2001). No reports linking this specific protein with any cancer could be found in the literature. Rab32 is down regulated in colon cancer (Mori et al. Cancer Res 64.2434-8.2004). Rab25 mRNA also was detected in several colon carcinoma lines, including LIM1215 and HT-29 (Goldenring et al. Methods Enzymol 329.225-34.2001). Some other members of the Rab family have been reported to be upregulated and aid in the development and aggressiveness of liver and several epithelial cancers (ovarian, breast, skin) (Gebhardt et al. Am J Pathol 167.243-53.2005; Cheng et al. Nat Med 10.1251-6.2004).

SOD3 (superoxide dismutase 3), a surface bound epithelial enzyme known to protect cells from oxygen free radical damage, is underexpressed in human intestinal tumor-derived epithelial cell (HITEC) lines. In a mouse model, Gao et al have shown that a chimeric recombinant SOD2/3 reduces lung leakage by 13% in acute lung injury (Gao et al. Am J Physiol Lung Cell Mol Physiol 284.L917-25.2003).

Myb (myeloblastosis) family transcription factors, A-Myb, B-Myb, and c-Myb, also called oncoproteins, share a highly conserved DNA binding domain and bind to the same DNA sequences, but have completely different biological roles.

A-Myb is regulated by the cell cycle machinery. The carboxy-terminal domain of A-Myb itself acts as a cell cycle sensor; its activity is maximal during the G1/S-transition and the S-phase of the cell cycle. (Ziebold et al. Curr Biol 7.253-60.1997). This transcription factor has been linked to the regulation of proliferation and/or differentiation of normal B cells and is overexpressed in Burkitt's lymphoma cells (Golay et al. Leuk Lymphoma 26.271-9.1997; Facchinetti et al. Biochem J 324 (Pt 3).729-36.1997).

The VCAM1 (vascular cell adhesion molecule 1) gene is a member of the Ig superfamily and encodes a cell surface sialoglycoprotein expressed by cytokine IL-6 and TNFalpha in activated endothelium (Khatib et al. Am J Pathol 167.749-59.2005). VCAM1 expression is variable in different types of carcinomas; it is detectable in colon cancers (Banner, Savas and Woda Ultrastruct Pathol 19.113-8.1995) and liver metastasis (Kitakata et al. Cancer Res 62.6682-7.2002), but not in adenocarcinoma of lung (Jiang et al. Mod Pathol 11.1189-92.1998) or esophagus (Heidemann et al. Int J Oncol 28.77-85.2006), and is down-regulated during nodal metastasis in breast cancer. Madhavan and Heidmann had proposed a potential role of VCAM-1 in the development of metastasis, since they found it was strongly expressed in squamous cell carcinoma (Madhavan et al. Pathol Oncol Res 8.125-8.2002; Heidemann et al. Int J Oncol 28.77-85.2006). However Lieder's group observed a gradual decrease in expression of VCAM-1 with progressive metastatic disease (Lieder et al. Anticancer Res 25.4141-7.2005).

MSH2 (Muts (*Escherichia coli*) Homolog 2 (colon cancer, nonpolyposis Type 1)) is a human analog of the protein found in *E. coli* that plays a critical role in DNA nucleotide mismatch repair. It is well known that deletion of mismatch repair genes results in microsatellite instability (MSI), which is implicated in 15-20% of colorectal cancers (Hoops and Traber Hematol Oncol Clin North Am 11.609-33.1997; Lynch and Kaul J Natl Cancer Inst 92.511-2.2000). According to a recent study by Parc et al, microsatellite unstable tumors exhibited a better recurrence free survival than microsatellite stable tumors (Parc et al. Int J Cancer 86.60-6.2000).

Apoptosis Inhibitor 2 (API2) initially was identified in mucosa associated lymphoid tumors (MALT) and subsequently has been shown to inhibit apoptosis in a p53 mediated process (Stoffel and Le Beau Hum Hered 51.1-7.2001). Carcinogenic cells that have undergone numerous genetic mutations somehow escape apoptosis. Without being limited by theory, one likely explanation is underexpression of API2 in such cells.

Interferon induced protein 56, referred to as IFI-56K, is highly inducible by interferon gamma as well as by viral stimuli. Gene array studies have shown downregulation of this mRNA in oligodendrogliomas (Huang et al. Oncogene 23.6012-22.2004), however, large-cell lymphoma-derived cell lines show significant upregulation (Gaiser et al. J Hematother Stem Cell Res 11.423-8.2002). The literature contains a limited number of reports about the possible role of this protein.

Presenilin 2 (PSEN4; Alzheimer disease 4) has been associated with Alzheimer's disease (AD) and its expression signifies the induction and/or proliferation of an inflammatory response in AD brain (Riazanskaia et al. Mol Psychiatry 7.891-8.2002).

The GTPase Ran regulates multiple cellular functions throughout the cell cycle, including nucleocytoplasmic transport, nuclear membrane and spindle assembly (Trieselmann et al. J Cell Sci 116.4791-8.2003). A gene expression profiling study by Harousseau et al. correlated abnormal expression of RAN with rapid relapses of multiple myeloma (Harousseau, Shaughnessy and Richardson Hematology Am Soc Hematol Educ Program 237-56.2004).

The Fos gene family consists of 4 members: FOS, FOSB, FOSL1, and FOSL2. These genes encode leucine zipper proteins that dimerize with proteins of the JUN family and form the transcription factor complex AP-1. The FOS proteins function as regulators of cell proliferation, differentiation, and transformation. They have been implicated in gliomas (Debinski and Gibo Mol Cancer Res 3.237-49.2005), breast cancer (Belguise et al. Oncogene 24.1434-44.2005) and colorectal adenocarcinomas (Wang et al. Int J Cancer 101.301-10.2002).

Gastrointestinal (GI) diseases, such as colon cancer, inflammatory bowel disease (IBD), short bowel syndrome, gastroesophageal reflux disease (GERD), irritable bowel syndrome (IBS), and iatrogenic injuries to the billiary epithelium, have a significant health and economic impact worldwide. Many treatments focus on symptom relief, and are not curative. Studies have suggested the main affected cellular component of these diseases is the epithelium.

Colorectal cancer (CRC) is the second leading cause of cancer death and is the third most common cause of malignancy in the U.S. While early stage disease can be cured with multimodality therapies, the majority of patients present with Stage III or IV disease (Jemal et al. CA Cancer J Clin 58.71-96.2008). The prognosis for patients with advanced CRC generally is poor.

Currently, no specific biomarker exists to aid in early diagnosis and/or management of CRC. While the actual cause of CRC remains unknown, the source of this disease is transformation of the epithelial cells lining the colon and or rectum. Previous studies with colonic tumor epithelial cell lines and/or tissues indicate that in most cases, tumor development is associated with aberrant gene expression (Rieker et al. Pathol Oncol Res 14.199-204.2008; Hagymasi et al. Ory Hetil 148.779-85.2007). Comparisons of the gene and/or protein expression profiles of normal and cancerous tissues in histological samples have identified several candidates that may be responsible for cancer development (Solmi et al. BMC Cancer 6.250.2006; Lepourcelet et al. Development 132.415-27.2005; Solmi et al. Int J Oncol 25.1049-56.2004; Ohnishi et al. Cancer Res 58.2440-4.1998; Hargest and Williamson Gut 37.826-9.1995). However, none of these genes or molecules have proved to be specific. This partially may be due to the fact that studies that compare differential gene expression between tumor and normal colorectal epithelium have been limited by the lack of paired normal and tumor-derived colorectal epithelial cell lines from the same individual.

Identification of early stage CRC biomarkers is vital for earlier CRC detection, biopsies, therapeutic target identification, drug testing, efficacy and treatment. However, significant difficulties for identifying these biomarkers exist. Most subjects with early CRC are asymptomatic, and symptoms usually do not appear until the cancer has reached an advanced stage (Schneider et al. Cancer 110.2075-82.2007; Glimelius et al. Acta Oncol 31.645-51.1992). Additionally, many individuals do not avail themselves of colonoscopy (the best means of early detection) due to its costly and invasive nature. Therefore, a high percentage of CRC cases are not detected until the cancer has progressed substantially, invaded adjoining tissues, and/or metastasized, which accounts for both the high percentage of reoccurrence and relatively high mortality rate observed (Walgenbach-Brunagel et al. J Cell Biochem 104.286-94.2008; Shapero et al. Gastrointest Endosc 65.640-5.2007). Further, the vast majority of CRC biomarkers that have been discovered do not have a function in vivo, are not very effective in early detection of CRC, recognize only a small subset of cancers, and often only detect CRC after it has progressed to later stages and grades.

Research efforts have utilized whole tissue sections, peripheral blood cells, serum and urine. These models do not allow the identification of the specific cellular, molecular, and genetic changes that the colonic epithelium undergoes throughout its malignant transformation.

Chronic inflammatory diseases, such as, for example, ulcerative colitis (UC) and Crohn's disease (CD), have been known for many years to predispose to cancer development (Herszenyi, Miheller and Tulassay Dig Dis 25.267-9.2007; Svrcek et al. Histopathology 50.574-83.2007; van Hogezand et al. Scand J Gastroenterol Suppl 48-53.2002).

Models incorporating malignant transformed cell lines, isolated epithelial cells, and animals have been used to study the functional capabilities, and alterations in the acute and chronic inflammatory or malignant states of epithelial cells. However, each of these model systems has limitations and differs markedly from an in vivo system of primary epithelial cells. For example, malignant cell lines usually have chromosomal abnormalities that cause instability. Tumor lines also differ from cell line to cell line, and from passage to passage (Jobin et al. J Immunol 158.226-34.1997; Khan et al. Anticancer Res 11.1343-8.1991; Owen-Schaub et al. Cancer Res 54.1580-6.1994). The use of freshly isolated epithelial cells often is complicated due to the mixture of several cell types present (T cells, B cells, or macrophages), especially when diseased tissue is used as cell source). Additionally, the isolation procedure can alter the phenotype of the cells by cleaving certain molecules from the cell surface. Furthermore, surface and crypt epithelial cells may have different phenotypes and functions and are not usually used in fully separated populations.

A model incorporating SV40 transformed epithelial cell lines established from human, mouse and rat epithelium (Brandsch et al. Scand J Gastroenterol 33.833-8.1998; Moyer et al. Prog Clin Biol Res 279.363-72.1988; Quaroni and Beaulieu Gastroenterology 113.1198-213.1997; Schorkhuber et al. Cell Biol Toxicol 14.211-23.1998). has been utilized. Although this model system allows the cells to retain some specific functions and to survive indefinitely, there has been concern about the altered growth control in these cells through the transfection of viral DNA (such as the large T-antigen gene from SV40) (Haufel et al. J Cell Biol 117.825-39.1992; Kim et al. Dev Biol Stand 94.297-302.1998; Ozer Prog Mol Subcell Biol 24.121-53.2000). Similarly, findings with animal model systems show that these do not always mimic precisely the functional scenarios of human intestinal epithelial cells in vivo (Seshimo et al. Cell Struct Funct 18.345-54.1993).

Cell lines of non-transformed human intestinal epithelial cells and of colorectal cancer cells (derived from primary cells and not artificially transformed) have long been needed for advancing research into the cause(s), prevention, treatment, and cure of colorectal cancer as well as other GI disorders such as, but not limited to, inflammatory bowel disease (IBD), Barrett's esophagitis/esophageal adenocarcinoma, gastritis, gastric cancer, ulcerative colitis (UC), Crohn's Disease (CD), and irritable bowel syndrome.

An understanding of the pathogenesis of CRC is heavily dependent on identifying differences between normal and tumorous colon epithelium. A non-transformed comparative cell line model using cells derived from normal and tumorous colon epithelium from the same individual would provide insight into these differences. However, no such model has been available. Therefore a need exists for an adequate preclinical model that provides an environment similar to the physiological environment of a human gastrointestinal tract.

The described invention provides a preclinical, in vitro system comprising gastrointestinal epithelial stem cell-like progenitor cells having the structural and functional characteristics of the normal human gastrointestinal tract. The system is useful for identifying specific bio-molecules that are involved in, or indicative of, inflammatory (e.g. ulcerative colitis and Crohn's disease) processes and/or cancerous development. Further, the specific biomolecules involved in, or indicative of, cancerous development may be used to develop and commercialize diagnostic and/or therapeutic constructs (such as antibodies, peptides, and small interfering RNA) against these molecules.

The described invention also provides a system useful for simulating microenvironments that may cause malignant changes on normal Human Intestinal Primary Epithelial Cells (HIPECs) as well as for evaluating of the effects of various therapeutic agents in reversing the malignant transformation process.

The described invention further provides a cell system useful for identifying biomarkers for colon cancer and other tumors of the gastrointestinal tract. The described invention moreover provides a system useful for studying differential alterations in the cellular machinery of tumorous epithelial stem cells by comparing these cells with their normal counterparts.

SUMMARY

Figure 1:
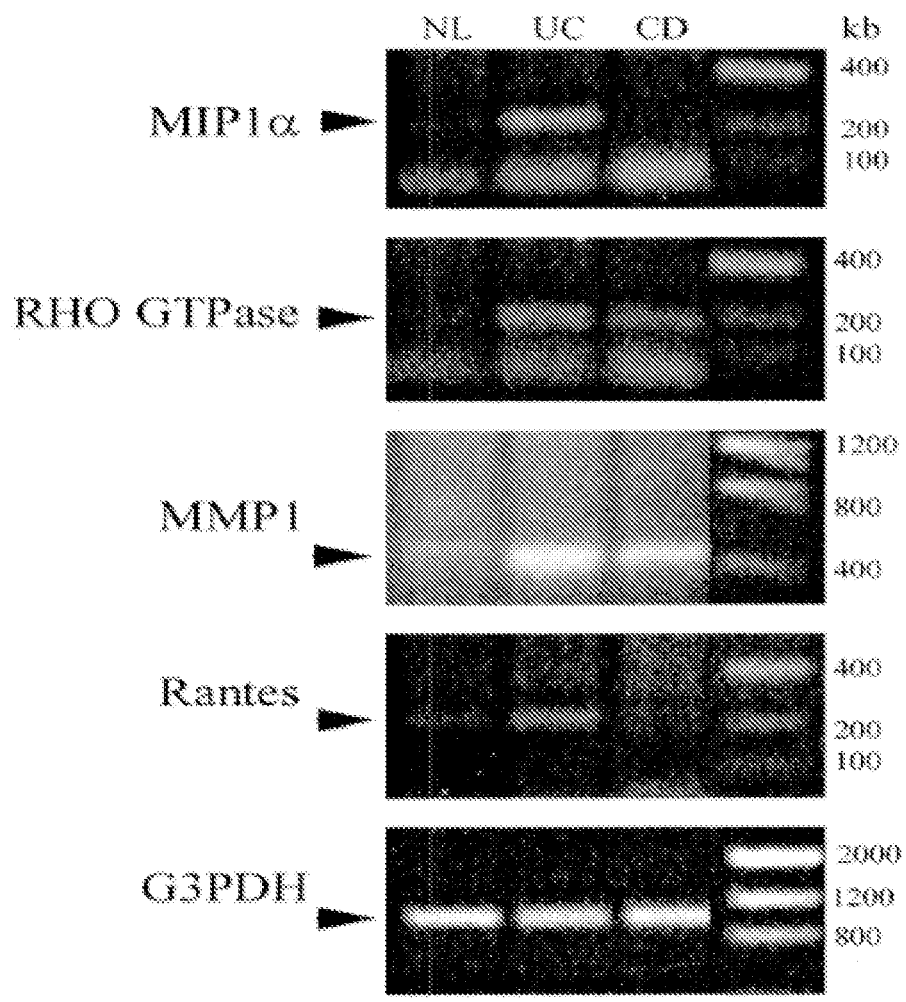
FIG. 1 shows biomarkers that were identified in epithelial cell lines derived from patients with IBD (both UC and CD) samples. Total RNA was extracted from a panel (normal control (NL); ulcerative colitis (UC); and Crohn's disease (CD)) of HIPEC monolayers and processed for RT-PCR (35 cycles) with specific primers. Electrophoresis of amplified PCR products on 1.8% agarose gel and subsequent staining with ethidium bromide, showed distinct bands of predicted molecular weight for MIP1α, RHO GTPase, MMP1 and Rantes. Detection of glyceraldehyde-3-phosphate dehydrogenase (G3PDH; housekeeping gene) mRNA in all lanes served as a control (lower panels) for normalization. All four genes examined were aberrantly expressed in UC, CD, or in both when compared to NL control.

According to one aspect, the described invention provides a method for identifying a therapeutic target to treat a colon cancer in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; (f) measuring the level of expression of a biomarker, wherein the level of expression of the biomarker is measured in the normal human intestinal primary epithelial cell line of step (e) and in the diseased human intestinal primary epithelial cell line of step (e); and (g) identifying a therapeutic target for the treatment of colon cancer by comparing the level of expression of the biomarker in the normal human intestinal primary cell line of step (f) and in the diseased human intestinal primary epithelial cell line of step (f). According to one embodiment, the biomarker is selected from the group consisting of STX5A, GZMB, PCSK5, and SOD3. According to another embodiment, step (f) further comprises the step of performing an assay that detects at least one of (i) at least one overexpressed gene in a sample obtained from the subject and (ii) at least one under-expressed gene in a sample obtained from the subject. According to another embodiment, the assay in step (f) is a microarray hybridization assay. According to another embodiment, the cell lines of step (f) are compared by immunoassay. According to another embodiment, the gastrointestinal segment is at least one gastrointestinal segment selected from the group consisting of an esophagus segment, a stomach segment, a jejunum segment, an ileum segment, a duodenum segment, an ascending colon segment, a transverse colon segment, a sigmoid colon segment, or a rectum segment. According to another embodiment, the normal differentiable segment-specific human stem cell-like progenitor cells have a phenotype of at least cytokeratin (+) and β-1-integrin(+). According to another embodiment, the normal differentiable segment-specific human stem cell-like progenitor cells have a phenotype of cytokeratin (+), β-1-integrin(+), defensin-5(+), trefoil factor-3(+), mucin-2(+), chomogranin-A(+), intestinal alkaline phosphatase(+), and lysozyme(+).

According to another aspect, the described invention provides a method for identifying at least one therapeutic target to treat ulcerative colitis in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; (f) measuring the level of expression of a biomarker, wherein the level of expression of the biomarker is measured in the normal human intestinal primary epithelial cell line of step (e) and in the diseased human intestinal primary epithelial cell line of step (e); and (g) identifying a therapeutic target for the treatment of ulcerative colitis by comparing the level of expression of the biomarker within the normal human intestinal primary cell line of step (f) and in the diseased human intestinal primary epithelial cell line of step (f). According to another embodiment, the biomarker is selected from the group consisting of BST2, MMP1, CACNA1E, PCSK5, GSTT1, SOD3, IL1RL1, ARH1 and IFIT156. According to another embodiment, step (f) further comprises the step of performing an assay that detects at least one of (i) at least one overexpressed gene in a sample obtained from the subject or (ii) at least one underexpressed gene in a sample obtained from the subject. According to another embodiment, the assay in step (f) is a microarray hybridization assay. According to another embodiment, in step (d), the biomarker is in a regulated state. According to another embodiment, the cell lines of step (f) are compared by an immunoassay. According to another embodiment, the gastrointestinal segment is an esophagus segment, a stomach segment, a duodenum segment, a jejunum segment, an ileum segment, an ascending colon segment, a transverse colon segment, a sigmoid colon segment, or a rectum segment. According to another embodiment, the normal differentiable segment-specific human stem cell-like progenitor cells have a phenotype of at least cytokeratin (+) and β-1-integrin(+). According to another embodiment, the normal differentiable segment-specific human stem cell-like progenitor cells have a phenotype of cytokeratin (+), β-1-integrin(+), defensin-5(+), trefoil factor-3(+), mucin-2(+), chomogranin-A(+), intestinal alkaline phosphatase(+), and lysozyme(+).

According to another aspect, the described invention provides a method for identifying at least one therapeutic target to treat Crohn's disease in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; (f) measuring the level of expression of a biomarker, wherein the level of expression of the biomarker is measured in the normal human intestinal primary epithelial cell line of step (e) and in the diseased human intestinal primary epithelial cell line of step (e); and (g) identifying a therapeutic target for the treatment of Crohn's disease by comparing the level of expression of the biomarker in the normal human intestinal primary cell line of step (f) and in the diseased human intestinal primary epithelial cell line of step (f). According to another embodiment, the biomarker is selected from the group consisting of CACNA1E, GSTT1, PCSK5, COL15A1, EDIL3 and MM2. According to another embodiment, step (f) further comprises the step of performing an assay that detects at least one of (i) at least one overexpressed gene in a sample obtained from the subject or (ii) at least one underexpressed gene in a sample obtained from the subject. According to another embodiment, the assay in step (f) is a microarray hybridization assay. According to another embodiment, in step (d), the biomarker is in a regulated state. According to another embodiment, the cell lines of step (f) are compared by an immunoassay. According to another embodiment, the gastrointestinal segment is an esophagus segment, a stomach segment, a jejunum segment, an ileum segment, a duodenum segment, an ascending colon segment, a transverse colon segment, a sigmoid colon segment, or a rectum segment. According to another embodiment, the normal differentiable segment-specific human stem cell-like progenitor cells have a phenotype of at least cytokeratin (+) and β-1-integrin(+). According to another embodiment, the normal differentiable segment-specific human stem cell-like progenitor cells have a phenotype of cytokeratin (+), β-1-integrin(+), defensin-5(+), trefoil factor-3(+), mucin-2(+), chomogranin-A(+), intestinal alkaline phosphatase(+), and lysozyme(+).

According to another aspect, the described invention provides a method for identifying at least one therapeutic target to treat a gastrointestinal disease in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; and (f) identifying at least one biomarker as a therapeutic target for treating a gastrointestinal disease by comparing the normal human intestinal primary epithelial cell line and the diseased human intestinal primary epithelial cell line of step (e). According to another embodiment, the gastrointestinal disease is selected from the group consisting of achalasia, Barrett's oesophagus, colorectal cancer, gastric cancer, oesophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux oesophagitis, and ulcerative colitis. According to another embodiment, step (f) further comprises the step of performing an assay that detects at least one of (i) at least one overexpressed gene in a sample obtained from the subject and (ii) at least one underexpressed gene in a sample obtained from the subject. According to another embodiment, the assay in step (f) is a microarray hybridization assay. According to another embodiment, step (f) further comprises the step of comparing telomerase activity of the normal human intestinal primary epithelial cell line of step (c) and the cancerous human intestinal primary epithelial cell line of step (d) after exposing the normal human intestinal primary epithelial cell line of step (c) and the cancerous human intestinal primary epithelial cell line of step (d) to a therapeutic agent. According to another embodiment, in step (d) the biomarker is in a regulated state. According to another embodiment, the cell lines of step (f) are compared by an immunoassay. According to another embodiment, the gastrointestinal disease is colon cancer. According to another embodiment, the gastrointestinal segment is an esophagus segment, a stomach segment, a jejunum segment, an ileum segment, a duodenum segment, an ascending colon segment, a transverse colon segment, a sigmoid colon segment, or a rectum segment. According to another embodiment, the normal differentiable segment-specific human stem cell-like progenitor cells have a phenotype of at least cytokeratin (+) and β-1-integrin(+). According to another embodiment, the normal differentiable segment-specific human stem cell-like progenitor cells have a phenotype of cytokeratin (+), β-1-integrin(+), defensin-5(+), trefoil factor-3(+), mucin-2(+), chromogranin-A(+), intestinal alkaline phosphatase(+), and lysozyme(+).

According to another aspect, the described invention provides a method for monitoring the therapeutic efficacy of a therapeutic agent for treating a gastrointestinal inflammatory disease, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; (f) measuring the level of expression of a biomarker, wherein the level of expression of the biomarker is measured in the normal human intestinal primary epithelial cell line of step (e) and in the diseased human intestinal primary epithelial cell line of step (e); (g) correlating the difference between the level of the biomarker measured in the normal human intestinal primary epithelial cell line and the level of expression of the biomarker measured in the diseased human intestinal primary epithelial cell with the therapeutic efficacy of the therapeutic agent. According to another embodiment, the biomarker is selected from the group consisting of STX5A, GZMB, and PCSK5. According to another embodiment, the biomarker is selected from the group consisting of BST2, MMP1, CACNA1E, PCSK5, GSTT1, IL1RL1, ARH1 and IFIT156. According to another embodiment, the biomarker is SOD3. According to another embodiment, the gastrointestinal segment is at least one gastrointestinal segment selected from the group consisting of an esophagus segment, a stomach segment, a jejunum segment, an ileum segment, a duodenum segment, an ascending colon segment, a transverse colon segment, a sigmoid colon segment, or a rectum segment. According to another embodiment, the normal differentiable segment-specific human stem cell-like progenitor cells have a phenotype of at least cytokeratin (+) and β-1-integrin(+). According to another embodiment, the normal differentiable segment-specific human stem cell-like progenitor cells have a phenotype of cytokeratin (+), β-1-integrin(+), defensin-5(+), trefoil factor-3(+), mucin-2(+), chromogranin-A(+), intestinal alkaline phosphatase(+), and lysozyme(+). According to another embodiment, the gastrointestinal disease is selected from the group consisting of achalasia, Barrett's oesophagus, colorectal cancer, gastric cancer, oesophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux oesophagitis, and ulcerative colitis.

DETAILED DESCRIPTION

Glossary

The term "analyze" (or "analysis") in its various grammatical forms as used herein refers to the process whereby a material is separated into constituent parts or elements or essential features. Analyses according to the present invention may be performed by numerous assays including, but not limited to, ELISA, HPLC, PCR, real-time PCR, permeability assays, immunochemistry, flow cytometry, TEER, SDS-PAGE, microscopic analysis, fluorescence microscopy, electron microscopy, NMR, LC-MS, or other analytical or bioanalytical assays known to artisans of skill in the art.

As used herein, the term "antibody" includes, by way of example, both naturally occurring and non-naturally occurring antibodies. Specifically, the term "antibody" includes polyclonal antibodies and monoclonal antibodies, and fragments thereof. Furthermore, the term "antibody" includes single chain antibodies, chimeric antibodies, wholly synthetic antibodies, and fragments thereof. The terms "epitope" and "antigenic determinant" are used interchangeably herein to refer to the site on a molecule that an antibody combining site (ACS) recognizes and with which that antigenic antibody binds (combines). The epitope may be primary, secondary, or tertiary-sequence related.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The terms "bio-similar matrix environment" and "BSME" are used interchangeably herein to refer to a growth substrate upon which human gastrointestinal stem-cell-like progenitor cells may be grown. A segment-specific BSME (herein referred to as "SS-BSME") is formed when each BSME is supplemented with gastrointestinal mucosal tissue derived growth supporting factors (MTD-GSF) appropriate for the isolated viable stem-cell-like progenitor cells of the gastrointestinal mucosal tissue segment of the human gastrointestinal tract that the BSME is to host. Thus, in some embodiments, stomach-BSME is supplemented with growth supporting factors derived from the mucosal tissues of the stomach. In some embodiments, duodenum-BSME is supplemented with growth supporting factors derived from the mucosal tissues of the duodenum. In some embodiments, jejunum-BSME is supplemented with growth supporting factors derived from the mucosal tissues of the jejunum. In some embodiments, ileum-BSME is supplemented with growth supporting factors derived from the mucosal tissues of the ileum. In some embodiments, colon-BSME is supplemented with growth supporting factors derived from the mucosal tissues of the colon. In some embodiments, rectum-BSME is supplemented with growth supporting factors derived from the mucosal tissues of the rectum. Each SS-BSME is adjusted to a pH most appropriate for the gastrointestinal stem-like epithelial progenitor cell it is to host. Thus, the stomach-BSME is adjusted to about pH 1-2.0. The duodenum-BSME is adjusted to about pH 4-5.5. The jejunum-BSME is adjusted to about pH 5.5-7. The ileum-BSME is adjusted to about 7-7.5. The colon-BSME and rectum-BSME were adjusted to about pH 7-7.5.

The term "correlate" as used herein refers to place or bring into a mutual or reciprocal relation, or to establish an orderly connection between two (or more) sets of measures thought to be related.

The term "compare" as used herein refers to the examination of two or more objects, substances, molecules, states, proteins, nucleic acids, peptides, antibodies, segments, or subjects in order to note similarities and/or differences.

The term "crypt" as used herein refers to a pit-like depression or tubular recess. For example, within the gastrointestinal tract, at the base of the intestinal villi lie crypts where the epithelial cells proliferate.

The term "cultivate" and its various grammatical forms, as used herein, refers to the promoting, fostering, improving the growth of, or producing by allowing reproduction in predetermined media under controlled laboratory conditions.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The phrase "cytokine profile" refers to a set of characteristics or analysis of at least one cytokine of a cell(s), tissue(s), or organ(s).

The term "daughter cell" as used herein refers to one of the resultant cells that is generated when a cell undergoes cell division and divides into two cells. A cell that undergoes cell division and divides into two cells is referred to as a "parent" cell.

The term "differentiation" or "cellular differentiation" as used herein refers to the process by which a less specialized cell becomes a more specialized cell type. In adults, adult stem cells divide and create fully differentiated daughter cells during tissue repair and during normal cell turnover. Cell differentiation causes a cells' size, shape, polarity, metabolic activity, and responsiveness to signals to change dramatically. These changes largely are due to highly controlled modifications in gene expression. With a few exceptions, cellular differentiation almost never involves a change in the DNA sequence itself; thus, different cells can have very different physical characteristics despite having the same genome. The term "differentiated" as used herein refers to having a different character or function from the surrounding structures or from the original type. The term "differentiable" as used herein refers to the ability to undergo differentiation or to become differentiated.

The term "disease" or "disorder" are used interchangeably herein to refer to an impairment of health or a condition of abnormal functions. The term "diseased state" as used herein refers to being in a condition of disease or disorder. The term "syndrome" as used herein refers to a pattern of symptoms indicative of some disease or condition. The term "condition" as used herein refers to a variety of health states and is meant to include disorders or disease caused by any underlying mechanism or disorder.

Diseases of the human gastrointestinal tract include, but are not limited to, achalasia, Barrett's oesophagus, colorectal cancer, gastric cancer, esophageal cancer, celiac disease, ulcerative colitis, Crohn's disease, diverticulosis, diverticulitis, gastritis, irritable bowel syndrome, microscopic colitis, collagenous colitis, lymphocytic colitis, pancreatitis, reflux esophagitis and other inflammatory, infectious, or malignant conditions. Disease states often are quantified in the art using well known scoring systems, such as those elucidated in Goodman & Gilman's The Pharmacological Basis of Therapeutics, 10th Edition, Eds. J. G. Hardman and L. E. Limbird, McGraw-Hill Publishing, New York, N.Y., 2001, the entirety of which is incorporated herein by reference.

The phrase "DNA characteristic" refers to a trait, property or biological activity of a DNA molecule that may be used as an indicator.

The term "drug" as used herein refers to a therapeutic agent or any substance, other than food, used in the prevention, diagnosis, alleviation, treatment, or cure of disease. A drug is: (a) any article recognized in the official United States Pharmacopeia, official Homeopathic Pharmacopeia of the United States, or official National Formulary, or any supplement to any of them; (b) articles intended for use in the diagnosis, cure, mitigation, treatment, or prevention of disease in man or other animals; (c) articles (other than food) intended to affect the structure or any function of the body of man or other animals, and d) articles intended for use as a component of any articles specified in (a), (b) or (c) above.

The term "efficacy" as used herein means a therapeutic agent is therapeutically effective. Generally, a greater level of efficacy will be achieved by increasing the dose and/or frequency of administration of a therapeutic agent given to a population, such that a greater proportion of the population will receive a benefit and/or there will be a greater magnitude of benefit in an individual patient, or cell. If a first therapeutic agent is more potent than a second therapeutic agent, it will reach a greater level of efficacy than the second therapeutic agent using identical amounts of each.

The terms "expose" in its various grammatical forms, as used herein, refers to subjecting or allowing to be subjected to an action, influence, or condition.

The term human "gastrointestinal epithelial stem cell-like progenitor cell" as used herein refers to a cell having the phenotype cytokeratin(+), $\beta$-1-integrin(+), defensin-5(+), trefoil factor-3(+), mucin-2(+), chomogranin-A(+), intestinal alkaline phosphatase(+), lysozyme(+) or at least $\beta$-1-integrin (+), and cytokeratin(+).

The term "gastrointestinal mucosal tissue segments" as used herein refers to isolated anatomical segments of the human gastrointestinal tract. Gastrointestinal mucosal tissue segments include those prepared from the stomach, the duodenum, the jejunum, the ileum, the ascending colon, the transverse colon, the sigmoid, and the rectum.

The terms "gastrointestinal malignancy" or "colon cancer" are used interchangeably herein to refer to neoplastic changes in the epithelial linings of the colon and/or any other parts of the gastrointestinal tract characterized by uncontrolled growth of undifferentiated (anaplastic) cells that tend to invade surrounding tissue and to metastasize to distant body sites.

The terms "gene expression" and "expression" are used interchangeably herein to refer to the process by which inheritable information from a gene, such as a DNA sequence, is made into a functional gene product, such as protein or RNA.

The term "HIPEC" as used herein refers to human intestinal primary epithelial cell lines derived from gastrointestinal epithelial stem cell-like progenitor cells.

The term "HITEC" as used herein refers to human intestinal tumor-derived epithelial cells.

The term "human gastrointestinal tract" as used herein refers to the coordinated structure (mouth to rectum) having the function of ingesting and absorbing nutrients and excreting unabsorbed and waste products.

The term "inflammation" as used herein refers to a physiologic response to infection and injury in which cells involved in detoxification and repair are mobilized to the compromised site by inflammatory mediators. The classic signs of inflammation are pain (dolor), heat (calor), redness (rubor), swelling (tumor), and loss of function (functio laesa). Histologically, inflammation involves a complex series of events, including dilatation of arterioles, capillaries, and venules, with increased permeability and blood flow; exudation of fluids, including plasma proteins; and leukocytic migration into the inflammatory focus.

The term "acute inflammation" as used herein refers to inflammation, usually of sudden onset, characterized by the classical signs, with predominance of the vascular and exudative processes. The term "chronic inflammation" as used herein refers to inflammation of slow progress and marked chiefly by the formation of new connective tissue; it may be a continuation of an acute form or a prolonged low-grade form, and usually causes permanent tissue damage.

Regardless of the initiating agent, the physiologic changes accompanying acute inflammation encompass four main features: (1) vasodilation, which results in a net increase in blood flow, is one of the earliest physical responses to acute tissue injury; (2) in response to inflammatory stimuli, endothelial cells lining the venules contract, widening the intracellular junctions to produce gaps, leading to increased vascular permeability which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

During the inflammatory process, soluble inflammatory mediators of the inflammatory response work together with cellular components in a systemic fashion in the attempt to contain and eliminate the agents causing physical distress. The term "inflammatory mediators" as used herein refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, proinflammatory cytokines, including, but not limited to, interleukin-1, interleukin-4, interleukin-6, interleukin-8, tumor necrosis factor (TNF), interferon-gamma, and interleukin 12.

The term "isolate" as used herein refers to a process of obtaining a substance, molecule, protein, peptide, nucleic acid, virus, or antibody that is substantially pure and is free of other substances with which it ordinarily is found in nature or in vivo systems to an extent practical and appropriate for its intended use. The terms "substantially or essentially free" or "substantially or essentially pure" are used interchangeably to refer to a material, which is at least about 50%, at least about 60%, at least about 70%, at least about 80%, and/or at least about 90% free from components that normally accompany or interact with it as found in its naturally occurring environment. The term "measure" as used herein refers to any standard of comparison, estimation or judgment, or to ascertaining the extent, dimensions, quantity, or capacity by comparison with a standard.

The term "mucosa" as used herein refers to the mucous tissue lining various tubular structures, which comprises an epithelium, a lamina propria, and in the digestive tract, a layer of smooth muscle (muscularis mucomucosa).

The term "mucosal" as used herein means relating to the mucosa or mucous membrane.

The term "mutual" as used herein refers to something common to or shared by tow or more things.

The term "native" as used herein refers to the condition of an organ, molecule, compound, protein, or nucleic acid as it would normally occur in nature. For example, a native human gastrointestinal tract refers to a gastrointestinal tract found within a normal human subject.

The term "normal" is used herein to refer to a state of natural occurrence or on average being subtantially free from any infection or other form of disease or malformation, or from experimental therapy or manipulation.

The term "overexpressed" as used herein refers to an increased quantity of a gene or gene product.

The term "progenitor cell" as used herein refers to an immature or undifferentiated cell population in the gastrointestinal tract. Progenitor cells have a capacity for self-renewal and differentiation, although these properties may be limited. The majority of progenitor cells may lie dormant or possess little activity in the tissue in which they reside. They exhibit slow growth and their main role is to replace cells lost by normal attrition. Upon tissue damage or injury, progenitor cells may be activated by growth factors or cytokines, leading to increased cell division important for the repair process.

The term "regional specificity" as used herein refers to the ability of a therapeutic agent to affect a specific identified segment of the human gastrointestinal tract.

The term "regulated" as used herein refers to a modulation of gene expression. For example, transcription of a gene may be regulated by various factors such as, but not limited to, specificity factors, repressors, general transcription factors, activators or enhancers. "Up-regulation" is a process which occurs within a cell triggered by a signal (originating internal or external to the cell) which results in increased expression of one or more genes and as a result the protein(s) encoded by those genes. "Down-regulation" is a process resulting in decreased gene and corresponding protein expression.

The phrase "RNA characteristic" refers to a trait, property or biological activity of a RNA molecule that may be used as an indicator.

The term "specificity" as used herein refers to the ability of a biological molecule to selectively affect only one substance; for example, an antibody that binds to an antigen.

The term "stem cell" as used herein refers to undifferentiated cells having high proliferative potential with the ability to self-renew that can generate daughter cells that can undergo terminal differentiation into more than one distinct cell type. A cell that is able to differentiate into many cell types may be referred to as "pluripotent." A cell that is able to differentiate into all cell types may be referred to as "totipotent." Pluripotent stem cells undergo further specialization into multipotent progenitor cells that then give rise to functional cells. Examples of stem and progenitor cells include: hematopoietic stem cells (adult stem cells) from the bone marrow that give rise to red blood cells, white blood cells, and platelets; mesenchymal stem cells (adult stem cells) from the bone marrow that give rise to stromal cells, fat cells, and types of bone cells; epithelial stem cells (progenitor cells) that give rise to the various types of skin cells; and muscle satellite cells (progenitor cells) that contribute to differentiated muscle tissue.

The term "subject" or "individual" or "patient" are used interchangeably to refer to a member of an animal species of mammalian origin, including but not limited to, a mouse, a rat, a cat, a goat, sheep, horse, hamster, ferret, pig, a dog, a guinea pig, a platypus, a rabbit and a primate, such as, for example, a monkey, ape, or human.

The term "therapeutic agent" as used herein refers to a drug, molecule, nucleic acid, protein, composition or other substance that provides a therapeutic effect.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the $ED_{50}$ which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest, reduction or elimination of the progression of a disease manifestation. A therapeutic effect may directly or indirectly kill the diseased cells, arrest the accumulation of diseased cells, or reduce the accumulation of diseased cells in a human subject with a disease such as, but not limited to, achalasia, Barrett's esophagus, colorectal cancer, gastric cancer, esophageal cancer, coeliac disease, colitis, Crohn's disease, diverticulosis, diverticulitis, gastritis, inflammatory bowel disease, ulcerative colitis, irritable bowel syndrome, microscopic colitis, collagenous colitis, lymphocytic colitis, pancreatitis, reflux esophagitis, and ulcerative colitis.

The terms "therapeutically effective amount" and "pharmaceutically effective amount" are used interchangeably to refer to the amount that results in a therapeutic beneficial effect. The term as used herein shall also mean the dosage of a therapeutic agent which directly or indirectly reduces or increases the activity of molecules secreted by diseased and/or non-diseased cells participating in a disease manifestation, such that the amount of therapeutic agent arrests, reduces, or eliminates altogether the degree of the disease manifestation. Typically, a therapeutically effective amount will also eliminate, reduce, or prevent the progression of one or more diseases. A skilled artisan recognizes that in many cases a therapeutic agent may not provide a cure, but may only provide a partial benefit. Furthermore, the skilled artisan recognizes that because individual patients and disease states may vary, some patients may receive little, or no benefit at all. A dosage of therapeutic agent that "kills," "arrests," "reduces," or "eliminates" as described above, in at least some patients, is considered therapeutically effective. The term "dosage" as used herein refers to the dose or amount, and frequency of administering of a therapeutic agent in prescribed amounts. The term "dose" as used herein refers to the amount of therapeutic agent to be taken or applied all at one time or in fractional amounts within a given period.

The term "therapeutic target" as used herein refers to a native protein, molecule, compound, nucleic acid, organ, gland, ligand, receptor, organelle, or cell whose activity is modified by a drug resulting in a desirable therapeutic effect.

As used herein the term "treating" includes abrogating, substantially inhibiting, slowing or reversing the progression of a condition, substantially ameliorating clinical or aesthetical symptoms of a condition, substantially preventing the appearance of clinical or aesthetical symptoms of a condition, and protecting from harmful or annoying stimuli.

The term "variation" as used herein refers to a difference or deviation in structure or character from others of the same species or group.

The term "villi" as used herein refers to projections from the surface, especially of a mucous membrane. Intestinal villi are projections, about 0.5 mm to about 1.5 mm in length, of the mucous membrane of the small intestine. They are leaf-shaped in the duodenum and become shorter, more finger-shaped, and sparser in the ileum.

The term "underexpressed" as used herein refers to decreased quantity of a gene or gene product.

1. Method for Identifying Therapeutic Targets to Treat Gastrointestinal Disease

According to one aspect, the described invention provides a method for identifying a therapeutic target to treat a gastrointestinal disease in a subject in need thereof, the method comprising steps: (a) isolating normal differentiable segment-specific human stem cell-like progenitor cells from normal mucosal tissue derived from at least one normal gastrointestinal segment of the subject; (b) isolating diseased differentiable segment-specific human stem cell-like progenitor cells from diseased muscosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line (HIPEC); (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; and (f) identifying at least one biomarker as a therapeutic target by comparing the normal human intestinal primary epithelial cell line and the diseased human intestinal primary epithelial cell line of step (e).

According to one embodiment, the gastrointestinal disease is achalasia. According to another embodiment, the gastrointestinal disease is Barrett's oesophagus. According to another embodiment, the gastrointestinal disease is colorectal cancer. According to another embodiment, the gastrointestinal disease is gastric cancer. According to another embodiment, the gastrointestinal disease is oesophageal cancer. According to another embodiment, the gastrointestinal disease is coeliac disease. According to another embodiment, the gastrointestinal disease is colitis. According to another embodiment, the gastrointestinal disease is Crohn's disease. According to another embodiment, the gastrointestinal disease is diverticulosis. According to another embodiment, the gastrointestinal disease is diverticulitis. According to another embodiment, the gastrointestinal disease is gastritis. According to another embodiment, the gastrointestinal disease is inflammatory bowel disease. According to another embodiment, the gastrointestinal disease is ulcerative colitis. According to another embodiment, the gastrointestinal disease is irritable bowel syndrome. According to another embodiment, the gastrointestinal disease is microscopic colitis. According to another embodiment, the gastrointestinal disease is collagenous colitis. According to another embodiment, the gastrointestinal disease is lymphocytic colitis. According to another embodiment, the gastrointestinal disease is pancreatitus. According to another embodiment, the gastrointestinal disease is reflux oesophagitis. According to another embodiment, the gastrointestinal disease is ulcerative colitis.

According to another embodiment, step (f) further comprises the step of performing an assay that detects at least one of either (i) at least one overexpressed gene or (ii) at least one underexpressed gene in a sample obtained from the subject. According to some such embodiments, the assay is a microarray hybridization assay.

According to another embodiment, step (f) further comprises the step of identifying at least one variation in a DNA characteristic.

According to another embodiment, step (f) further comprises the step of identifying at least one variation in an RNA characteristic.

According to another embodiment, step (f) further comprises the step of identifying at least one variation in a cytokine profile.

According to another embodiment, step (f) further comprises the step of comparing telomerase activity of the normal HIPEC line and the diseased HIPEC line of step (e).

According to another embodiment, the normal HIPEC line and the diseased HIPEC are compared by gene array. According to some embodiments, the normal HIPEC line and the diseased HIPEC are compared by telomerase assay. According to some embodiments, the normal HIPEC line and the diseased HIPEC are compared by RT-PCR. According to some embodiments, the normal HIPEC line and the diseased HIPEC are compared by Northern analysis. According to some embodiments, the normal HIPEC line and the diseased HIPEC are compared by fluorescence 2-dimensional difference gel electrophoresis. According to some embodiments, the normal HIPEC line and the diseased HIPEC are compared by iTRAQ (isobaric tag for relative and absolute quantitation). According to some embodiments, the normal HIPEC line and the diseased HIPEC are compared by cICAT (cleavable isotope coded affinity tag). According to some embodiments, proteins expressed by the normal HIPEC line and the diseased HIPEC are compared by immunoassay. According to some such embodiments, the immunoassay is an ELISA. According to some such embodiments, the immunoassay is an immunoblot. According to some such embodiments, the immunoassay is a protein array. According to some such embodiments, the immunoassay is flow cytometry.

According to another embodiment, the gastrointestinal disease is colon cancer.

According to another embodiment, the gastrointestinal segment is an esophagus segment. According to another embodiment, the gastrointestinal segment is a stomach segment. According to another embodiment, the gastrointestinal segment is a duodenum segment. According to another embodiment, the gastrointestinal segment is a jejunum segment. According to another embodiment, the gastrointestinal segment is an ileum segment. According to another embodiment, the gastrointestinal segment is an ascending colon segment. According to another embodiment, the gastrointestinal segment is a transverse colon segment. According to another embodiment, the gastrointestinal segment is a sigmoid colon segment. According to another embodiment, the gastrointestinal segment is a rectum segment.

According to another embodiment, the normal differentiable segment-specific human stem cell-like progenitor cells have a phenotype of at least cytokeratin(+) and $\beta$-1-integrin (+).

According to some embodiments, the normal differentiable segment-specific human stem cell-like progenitor cells have a phenotype of cytokeratin(+), $\beta$-1-integrin(+), defensin-5(+), trefoil factor-3(+), mucin-2(+), chromogranin-A(+), intestinal alkaline phosphatase(+) and lysozyme (+).

2. Method for Identifying Therapeutic Targets to Treat Colon Cancer

According to another aspect, the described invention provides a method for identifying a therapeutic target to treat colon cancer in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subjects's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; (f) measuring a level of expression of a biomarker, wherein the level of expression of the biomarker is measured in the normal human intestinal primary epithelial cell line of step (e) and in the diseased human intestinal primary epithelial cell line of step (e); and (g) identifying a therapeutic target for the treatment of colon cancer by comparing the level of expression of the biomarker within the normal human intestinal primary cell line of step (f) and the diseased human intestinal primary epithelial cell line of step (f).

According to some embodiments, the biomarker is STX5A. According to another embodiment, the biomarker is GZMB. According to another embodiment, the biomarker is PCSK5. According to another embodiment, the biomarker is SOD3.

According to another embodiment, step (f) further comprises the step of performing an assay that detects at least one of (i) at least one overexpressed gene and (ii) at least one underexpressed gene in a sample obtained from the subject.

According to another embodiment, the assay in step (f) is a microarray hybridization assay.

According to another embodiment, step (f) further comprises the step of identifying at least one variation in a DNA characteristic. According to another embodiment, step (f) further comprises the step of identifying at least one variation in an RNA characteristic.

According to another embodiment, the cell lines of step (f) are compared by gene array. According to another embodiment, the cell lines of step (f) are compared by RT-PCR. According to another embodiment, the cell lines of step (f) are compared by Northern analysis. According to another embodiment, the cell lines of step (f) are compared by fluorescence 2-dimensional difference gel electrophoresis. According to another embodiment, the cell lines of step (f) are compared by iTRAQ. According to another embodiment, the cell lines of step (f) are compared by cICAT. According to another embodiment, the cell lines of step (f) are compared by immunoassay.

According to another embodiment, the immunoassay is an ELISA. According to another embodiment, the immunoassay is an immunoblot. According to another embodiment, the immunoassay is a protein array. According to another embodiment, the immunoassay comprises flow cytometry.

According to another embodiment, the gastrointestinal segment is an esophagus segment. According to another embodiment, the gastrointestinal segment is a stomach segment. According to another embodiment, the gastrointestinal segment is a duodenum segment. According to another embodiment, the gastrointestinal segment is a jejunum segment. According to another embodiment, the gastrointestinal segment is an ileum segment. According to another embodiment, the gastrointestinal segment is an ascending colon segment. According to another embodiment, the gastrointestinal segment is a transverse colon segment. According to another embodiment, the gastrointestinal segment is a sigmoid colon segment. According to another embodiment, the gastrointestinal segment is a rectum segment.

According to another embodiment, the normal differentiable segment-specific human stem cell-like progenitor cells have a phenotype of at least cytokeratin (+) and $\beta$-1-integrin (+).

According to another embodiment, the normal differentiable segment-specific human stem cell-like progenitor cells have a phenotype of cytokeratin (+), $\beta$-1-integrin(+), defensin-5(+), trefoil factor-3(+), mucin-2(+), chomogranin-A(+), intestinal alkaline phosphatase(+), and lysozyme(+).

According to some embodiments, the described invention provides a method for identifying a therapeutic target to treat a colon cancer in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line, wherein a biomarker is in a regulated state; (e) exposing the normal human intestinal primary epithelial cell line of step (c) and the diseased human intestinal primary epithelial cell line of step (d) to a therapeutic agent; (f) measuring a level of expression of the biomarker of step (d) in the normal human intestinal primary epithelial cell line of step (e) and in the diseased human intestinal primary epithelial cell line of step (e); and (g) comparing the level of expression of the biomarker within the normal human intestinal primary cell line of step (f) and the diseased human intestinal primary epithelial cell line of step (f), whereby a change in the level of expression of the biomarker of step (d) identifies a therapeutic target for the treatment of the colon cancer.

According to another embodiment, the regulated state of step (d) is an up-regulated state. According to another embodiment, the regulated state of step (d) is a down-regulated state.

According to another embodiment, the change in the level of expression of the biomarker of step (g) is an increase in the level of expression. According to another embodiment, the change in the level of expression of the biomarker of step (g) is a decrease in the level of expression.

3. Method for Identifying Therapeutic Targets to Treat Ulcerative Colitis

According to another aspect, the described invention provides a method for identifying a therapeutic target to treat ulcerative colitis in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line;

(d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; (f) measuring a level of expression of a biomarker, wherein the level of expression of the biomarker is measured in the normal human intestinal primary epithelial cell line of step (e) and in the diseased human intestinal primary epithelial cell line of step (e); and (g) identifying a therapeutic target for the treatment of colon cancer by comparing the level of expression of the biomarker within the normal human intestinal primary cell line of step (f) and the diseased human intestinal primary epithelial cell line of step (f).

According to one embodiment, the biomarker is BST2. According to another embodiment, the biomarker is MMP1. According to another embodiment, the biomarker is CACNA1E. According to another embodiment, the biomarker is PCSK5. According to another embodiment, the biomarker is GSTT1. According to another embodiment, the biomarker is SOD3. According to another embodiment, the biomarker is IL1RL1. According to another embodiment, the biomarker is ARH1. According to another embodiment, the biomarker is IFIT156.

According to another embodiment, step (f) further comprises the step of performing an assay that detects at least one of (i) at least one overexpressed gene or (ii) at least one underexpressed gene in a sample obtained from the subject.

According to another embodiment, the assay in step (f) is a microarray hybridization assay. According to another embodiment, step (f) further comprises the step of identifying at least one variation in a DNA characteristic. According to another embodiment, step (f) further comprises the step of identifying at least one variation in an RNA characteristic. According to another embodiment, the cell lines of step (f) are compared by gene array. According to another embodiment, the cell lines of step (f) are compared by RT-PCR. According to another embodiment, the cell lines of step (f) are compared by Northern analysis. According to another embodiment, the cell lines of step (f) are compared by fluorescence 2-dimensional difference gel electrophoresis. According to another embodiment, the cell lines of step (f) are compared by iTRAQ. According to another embodiment, the cell lines of step (f) are compared by cICAT.

According to another embodiment, the proteins expressed by cell lines of step (f) are compared by immunoassay. According to another embodiment, the immunoassay is an ELISA. According to another embodiment, the immunoassay is an immunoblot. According to another embodiment, the immunoassay is a protein array. According to another embodiment, the immunoassay comprises flow cytometry.

According to another embodiment, the gastrointestinal segment is an esophagus segment. According to another embodiment, the gastrointestinal segment is a stomach segment. According to another embodiment, the gastrointestinal segment is a duodenum segment. According to another embodiment, the gastrointestinal segment is a jejunum segment. According to another embodiment, the gastrointestinal segment is an ileum segment. According to another embodiment, the gastrointestinal segment is an ascending colon segment. According to another embodiment, the gastrointestinal segment is a transverse colon segment. According to another embodiment, the gastrointestinal segment is a sigmoid colon segment. According to another embodiment, the gastrointestinal segment is a rectum segment.

According to another embodiment, the normal differentiable segment-specific human stem cell-like progenitor cells have a phenotype of at least cytokeratin (+) and $\beta$-1-integrin (+).

According to another embodiment, the normal differentiable segment-specific human stem cell-like progenitor cells have a phenotype of cytokeratin (+), $\beta$-1-integrin(+), defensin-5(+), trefoil factor-3(+), mucin-2(+), chomogranin-A(+), intestinal alkaline phosphatase(+), and lysozyme(+).

According to some embodiments, the described invention provides a method for identifying a therapeutic target to treat ulcerative colitis in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; wherein the normal human intestinal primary epithelial cell line and the diseased human intestinal primary epithelial cell line have a mutual biomarker, wherein the biomarker is in a regulated state; (f) measuring the level of expression of the biomarker of step (e) in the normal human intestinal primary epithelial cell line and in the diseased human intestinal primary epithelial cell line; and (g) comparing the level of expression of the biomarker in the normal human intestinal primary cell line of step (f) and in the diseased human intestinal primary epithelial cell line of step (f), such that a change in the level of expression of the biomarker of step (e) identifies a therapeutic target for the treatment of ulcerative colitis.

According to another embodiment, the regulated state of step (d) is an up-regulated state. According to another embodiment, the regulated state of step (d) is a down-regulated state.

According to another embodiment, the change in the level of expression of the biomarker of step (g) is an increase in the level of expression. According to another embodiment, the change in the level of expression of the biomarker of step (g) is a decrease in the level of expression.

4. Method for Identifying Therapeutic Targets to Treat Crohn's Disease

According to another aspect, the described invention provides a method for identifying a therapeutic target to treat Crohn's disease in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; (f) measuring the level of expression of a biomarker, wherein the level of expression of the biomarker is measured in the normal human intestinal primary epithelial cell line of step (e) and in the diseased human intestinal primary epithelial cell line of step (e); and (g) identifying a therapeutic target for the treatment of colon cancer by comparing the level of expression of the biomarker within the normal human intestinal primary cell line of step (f) and the diseased human intestinal primary epithelial cell line of step (f).

According to another embodiment, the biomarker is CACNA1E. According to another embodiment, the biomarker is GSTT1. According to another embodiment, the biomarker is PCSK5. According to another embodiment, the biomarker is COL15A1. According to another embodiment, the biomarker is EDIL3. According to another embodiment, the biomarker is MM2.

According to another embodiment, step (f) further comprises the step of performing an assay that detects at least one of at least one overexpressed gene or at least one underexpressed gene in a sample obtained from the subject.

According to another embodiment, the assay in step (f) is a microarray hybridization assay.

According to another embodiment, step (f) further comprises the step of identifying at least one variation in a DNA characteristic. According to another embodiment, step (f) further comprises the step of identifying at least one variation in an RNA characteristic.

According to another embodiment, the proteins expressed by the cell lines of step (f) are compared by gene array. According to another embodiment, the cell lines of step (f) are compared by RT-PCR. According to another embodiment, the cell lines of step (f) are compared by Northern analysis. According to another embodiment, the cell lines of step (f) are compared by fluorescence 2-dimensional difference gel electrophoresis. According to another embodiment, the cell lines of step (f) are compared by iTRAQ. According to another embodiment, the cell lines of step (f) are compared by cICAT.

According to another embodiment, the cell lines of step (f) are compared by immunoassay. According to another embodiment, the immunoassay is an ELISA. According to another embodiment, the immunoassay is an immunoblot. According to another embodiment, the immunoassay is a protein array. According to another embodiment, the immunoassay comprises flow cytometry.

According to another embodiment, the gastrointestinal segment is an esophagus segment. According to another embodiment, the gastrointestinal segment is a stomach segment. According to another embodiment, the gastrointestinal segment is a duodenum segment. According to another embodiment, the gastrointestinal segment is a jejunum segment. According to another embodiment, the gastrointestinal segment is an ileum segment. According to another embodiment, the gastrointestinal segment is an ascending colon segment. According to another embodiment, the gastrointestinal segment is a transverse colon segment. According to another embodiment, the gastrointestinal segment is a sigmoid colon segment. According to another embodiment, the gastrointestinal segment is a rectum segment.

According to another embodiment, the normal differentiable segment-specific human stem cell-like progenitor cells have a phenotype of at least cytokeratin (+) and $\beta$-1-integrin (+). According to another embodiment, the normal differentiable segment-specific human stem cell-like progenitor cells have a phenotype of cytokeratin (+), $\beta$-1-integrin(+), defensin-5(+), trefoil factor-3(+), mucin-2(+), chomogranin-A(+), intestinal alkaline phosphatase(+), and lysozyme(+).

According to some embodiments, the described invention provides a method for identifying a therapeutic target to treat Crohn's disease in a subject in need thereof, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line, wherein a biomarker is in a regulated state; (e) exposing the normal human intestinal primary epithelial cell line of step (c) and the diseased human intestinal primary epithelial cell line of step (d) to a therapeutic agent; (f) measuring the level of expression of the biomarker of step (d) in the normal human intestinal primary epithelial cell line of step (e) and in the diseased human intestinal primary epithelial cell line of step (e); and (g) comparing the level of expression of the biomarker within the normal human intestinal primary cell line of step (f) and in the diseased human intestinal primary epithelial cell line of step (f), whereby a change in the level of expression of the biomarker of step (d) identifies a therapeutic target for the treatment of Crohn's disease.

According to another embodiment, the regulated state of step (d) is an up-regulated state. According to another embodiment, the regulated state of step (d) is a down-regulated state. According to another embodiment, the change in the expression level of the biomarker of step (g) is an increase in the expression level. According to another embodiment, the change in the expression level of the biomarker of step (g) is a decrease in the expression level.

5. Method for Monitoring Treatment of a Gastrointestinal Disease

According to another aspect, the described invention provides a method for monitoring the efficacy of a therapeutic agent for treating a gastrointestinal inflammatory disease, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal segment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) exposing the normal human intestinal primary epithelial cell line of step (c) and the diseased human intestinal primary epithelial cell line of step (d) to a therapeutic agent; (f) measuring the level of expression of a biomarker, wherein the level of expression of the biomarker is measured in the normal human intestinal primary epithelial cell line of step (e) and in the diseased human intestinal primary epithelial cell line of step (e); (g) correlating the difference between the level of expression of the biomarker measured in the normal human intestinal primary epithelial cell line and the level of expression of the biomarker measured in the diseased human intestinal primary epithelial cell with the treatment efficacy of the therapeutic agent.

According to some embodiments, wherein step (g) the correlating the difference between the level of expression of the biomarker measured in the normal human intestinal primary epithelial cell line and the level of expression of the biomarker measured in the diseased human intestinal primary epithelial cell with the treatment efficacy of the therapeutic agent is by use of a computer.

According to some embodiments, wherein step (g) the correlating the difference between the level of expression of the biomarker measured in the normal human intestinal primary epithelial cell line and the level of expression of the biomarker measured in the diseased human intestinal primary epithelial cell with the treatment efficacy of the therapeutic agent allowing for optimizing the therapeutic efficacy of a treatment for a gastrointestinal inflammatory disease. According to some such embodiments, the correlating the difference between the level of expression of the biomarker measured in the normal human intestinal primary epithelial cell line and the level of expression of the biomarker measured in the diseased human intestinal primary epithelial cell with the treatment efficacy of the therapeutic agent allowing for optimizing the therapeutic efficacy of a treatment for a gastrointestinal inflammatory disease is by use of a computer.

According to another such embodiment, the gastrointestinal disease is colon cancer. According to another embodiment, the gastrointestinal disease is ulcerative colitis. According to another embodiment, the gastrointestinal disease is Crohn's disease. gastrointestinal disease is achalasia. According to another embodiment, the gastrointestinal disease is Barrett's oesophagus. According to another embodiment, the gastrointestinal disease is colorectal cancer. According to another embodiment, the gastrointestinal disease is gastric cancer. According to another embodiment, the gastrointestinal disease is oesophageal cancer. According to another embodiment, the gastrointestinal disease is coeliac disease. According to another embodiment, the gastrointestinal disease is colitis. According to another embodiment, the gastrointestinal disease is diverticulosis. According to another embodiment, the gastrointestinal disease is diverticulitis. According to another embodiment, the gastrointestinal disease is gastritis. According to another embodiment, the gastrointestinal disease is inflammatory bowel disease. According to another embodiment, the gastrointestinal disease is irritable bowel syndrome. According to another embodiment, the gastrointestinal disease is microscopic colitis According to another embodiment, the gastrointestinal disease is collagenous colitis. According to another embodiment, the gastrointestinal disease is lymphocytic colitis. According to another embodiment, the gastrointestinal disease is pancreatitis. According to another embodiment, the gastrointestinal disease is reflux oesophagitis.

According to another embodiment, the biomarker is CACNA1E. According to another embodiment, the biomarker is PCSK5. According to another embodiment, the biomarker is COL15A1. According to another embodiment, the biomarker is EDIL3. According to another embodiment, the biomarker is MM2. According to one embodiment, the biomarker is BST2. According to another embodiment, the biomarker is MMP1. According to another embodiment, the biomarker is GSTT1. According to another embodiment, the biomarker is SOD3. According to another embodiment, the biomarker is IL1RL1. According to another embodiment, the biomarker is ARH1. According to another embodiment, the biomarker is IFIT 156. According to some embodiments, the biomarker is STX5A. According to another embodiment, the biomarker is GZMB. According to another embodiment, the biomarker is SOD3.

According to another embodiment, the gastrointestinal segment is an esophagus segment. According to another embodiment, the gastrointestinal segment is a stomach segment. According to another embodiment, the gastrointestinal segment is a duodenum segment. According to another embodiment, the gastrointestinal segment is a jejunum segment. According to another embodiment, the gastrointestinal segment is an ileum segment. According to another embodiment, the gastrointestinal segment is an ascending colon segment. According to another embodiment, the gastrointestinal segment is a transverse colon segment. According to another embodiment, the gastrointestinal segment is a sigmoid colon segment. According to another embodiment, the gastrointestinal segment is a rectum segment.

According to another embodiment, the normal differentiable segment-specific human stem cell-like progenitor cells have a phenotype of cytokeratin(+), β-1-integrin(+), defdefensin-5(+), trefoil factor-3(+), mucin-2(+), chromogranin-A (+), intestinal alkaline phosphatase(+), and lysozyme(+).

According to another embodiment, the normal differentiable segment-specific human stem cell-like progenitor cells have a phenotype of at least cytokeratin (+) and β-1-integrin (+).

According to another embodiment, the described invention provides a method of monitoring treatment of a gastrointestinal disease in a subject being treated with a therapeutic agent, the method comprising the steps: (a) performing an assay that detects a change in one or more biomarkers indicative of transformation of an intestinal epithelial cell in a sample obtained from a subject; (b) performing an assay that detects a change in expression of at least one overexpressed and underexpressed gene in a sample obtained from a subject; and (c) correlating the assay results obtained from the assays performed in step (a) and step (b) to the treatment efficacy of a therapeutic agent in the patient.

According to one embodiment, the sample is a tissue sample. According to another embodiment, the sample is a blood sample. According to another embodiment, the sample is a serum sample. According to another embodiment, the sample is a plasma sample.

According to another embodiment, the assay in step (a) further comprises the steps: (i) isolating differentiable segment-specific human stem cell-like progenitor cells from mucosal tissue derived from at least one gastrointestinal segment; (ii) cultivating the differentiable segment-specific human stem cell-like progenitor cells on a biosimilar matrix environment formed from the mucosal tissue derived from at least one gastrointestinal segment to produce a HIPEC line derived from the differentiable segment-specific epithelial stem cell-like progenitor cells; and (iii) comparing at least one aspect of the HIPEC line to a reference HIPEC line.

According to another such embodiment, the at least one aspect in step (iii) comprises a variation in a DNA characteristic. According to another embodiment, the at least one aspect in step (iii) comprises a variation in a RNA characteristic. According to another embodiment, the at least one aspect in step (iii) comprises a variation in a cytokine profile.

According to another such embodiment, the assay in step (b) is a microarray hybridization assay.

6. Method for Diagnosing a Gastrointestinal Disease

According to another aspect, the described invention provides a method for diagnosing a gastrointestinal disease in a subject, the method comprising the steps: (a) isolating normal differentiable segment-specific human stem cell-like progenitor cells from normal mucosal tissue of the subject derived from at least one normal gastrointestinal segment; (b) isolating diseased differentiable segment-specific human stem cell-like progenitor cells from diseased mucosal tissue derived from at least one segment of the subject's diseased human gastrointestinal egment; (c) cultivating the normal differentiable segment-specific human stem cell-like progenitor cells from step (a) on a biosimilar matrix environment formed from the normal mucosal tissue derived from the at least one normal human gastrointestinal segment to produce a normal human intestinal primary epithelial cell line; (d) cultivating the diseased differentiable segment-specific human stem cell-like progenitor cells from step (b) on a biosimilar matrix environment formed from the diseased mucosal tissue of step (b) to produce a diseased human intestinal primary epithelial cell line; (e) measuring the level of expression of a biomarker, wherein the level of expression of the biomarker is measured in the normal human intestinal primary epithelial cell line of step (e) and in the diseased human intestinal primary epithelial cell line of step (e); (f) correlating the difference between the level of expression of the biomarker measured in the normal human intestinal primary epithelial cell line and the level of expression of the biomarker measured in the diseased human intestinal primary epithelial cell line with a gastrointestinal disease state.

According to some embodiments, wherein step (g) correlating the difference between the level of expression of the biomarker measured in the normal human intestinal primary epithelial cell line and the level of expression of the biomarker measured in the diseased human intestinal primary epithelial cell line with a gastrointestinal disease state is by use of a computer.

According to another embodiment, the gastrointestinal disease is colon cancer. According to another embodiment, the gastrointestinal disease is ulcerative colitis. According to another embodiment, the gastrointestinal disease is Crohn's disease. According to another embodiment, the gastrointestinal disease is achalasia. According to another embodiment, the gastrointestinal disease is Barrett's oesophagus. According to another embodiment, the gastrointestinal disease is colorectal cancer. According to another embodiment, the gastrointestinal disease is gastric cancer. According to another embodiment, the gastrointestinal disease is oesophageal cancer. According to another embodiment, the gastrointestinal disease is coeliac disease. According to another embodiment, the gastrointestinal disease is colitis. According to another embodiment, the gastrointestinal disease is diverticulosis. According to another embodiment, the gastrointestinal disease is diverticulitis. According to another embodiment, the gastrointestinal disease is gastritis. According to another embodiment, the gastrointestinal disease is inflammatory bowel disease. According to another embodiment, the gastrointestinal disease is irritable bowel syndrome. According to another embodiment, the gastrointestinal disease is microscopic colitis According to another embodiment, the gastrointestinal disease is collagenous colitis. According to another embodiment, the gastrointestinal disease is lymphocytic colitis. According to another embodiment, the gastrointestinal disease is pancreatitis. According to another embodiment, the gastrointestinal disease is reflux oesophagitis.

According to another embodiment, the biomarker is CACNA1E. According to another embodiment, the biomarker is PCSK5. According to another embodiment, the biomarker is COL15A1. According to another embodiment, the biomarker is EDIL3. According to another embodiment, the biomarker is MM2. According to one embodiment, the biomarker is BST2. According to another embodiment, the biomarker is MMP1. According to another embodiment, the biomarker is GSTT1. According to another embodiment, the biomarker is SOD3. According to another embodiment, the biomarker is IL1RL1. According to another embodiment, the biomarker is ARH1. According to another embodiment, the biomarker is IFIT156. According to some embodiments, the biomarker is STX5A. According to another embodiment, the biomarker is GZMB.

According to another embodiment, the biomarker is SOD3 and wherein step (f) the difference between the level of expression of the biomarker measured in the normal human intestinal primary epithelial cell line and the level of expression of the biomarker measured in the diseased human intestinal primary epithelial cell line is at least about 2-fold.

According to another embodiment, the described invention provides a method of diagnosing a gastrointestinal disease in a subject, the method comprising the steps: (a) performing an assay that detects at least one biomarker indicative of transformation of an intestinal epithelial cell in a sample obtained from the subject; (b) performing an assay that detects at least one of (i) at least one overexpressed gene and (ii) at least one underexpressed gene in a sample obtained from the subject; and (c) correlating the assay results obtained from the assays performed in step (a) and step (b) to the presence or absence of at least one transformed intestinal epithelial cell in the patient.

According to some such embodiments, the assay in step (a) further comprises the steps: (i) isolating differentiable gastrointestinal segment-specific human stem cell-like progenitor cells from mucosal tissue derived from at least one gastrointestinal segment; (ii) cultivating the differentiable gastrointestinal segment-specific human stem cell-like progenitor cells on a biosimilar matrix environment formed from the mucosal tissue derived from the at least one segment to produce a human intestinal primary epithelial cell line; and (iii) comparing at least one aspect of the human intestinal primary epithelial cell line to at least one aspect of a reference human intestinal tumor-derived epithelial cell line.

According to some such embodiments, the at least one aspect in step (iii) comprises a variation in a DNA characteristic. According to some such embodiments, the at least one aspect in step (iii) comprises a variation in an RNA characteristic. According to some such embodiments, the at least one aspect in step (iii) comprises a variation in a cytokine profile.

According to some such embodiments, the assay in step (b) is a microarray hybridization assay.

According to some such embodiments, the method further comprises the step of performing at least one additional assay that detects at least one additional diagnostic indicator. Such additional diagnostic indicators include, but are not limited to, increased telomerase activity.

According to another embodiment, the sample is a tissue sample. According to another embodiment, the sample is a blood sample. According to another embodiment, the sample is a serum sample. According to another embodiment, the sample is a plasma sample.

7. Paired Epithelial Cell System

The described invention provides for a paired epithelial cell system obtained from tumorous and normal segments of the gastrointestinal (GI) tract. Such a system is established from isolated stem cell-like progenitor cells from various segments of the human gastrointestinal tract, e.g., human esophageal normal epithelial cells (HENEC), and human esophageal tumor epithelial cells (HETEC), human gastric normal epithelial cells (HGNEC), and human gastric tumor epithelial cells (HGTEC), etc.

According to one embodiment, the paired epithelial cell system from actively inflamed (diseased) and non-inflamed (normal) segments of the gastrointestinal tract can be established from isolated stem cell-like progenitor cells from various segments of the human GI tract, including, but not limited to, human epithelial cells from actively inflamed (AIEC) and uninflamed (UIEC) tissues from patients with ulcerative colitis (UC), Crohn's disease (CD), and irritable bowel syndrome (IBS).

It generally is believed that better recurrence-free survival in patients will be correlated with aberrant gene expression. For example, better recurrence free survival in patients may be correlated with aberrant MSH2 gene expression. Consequently, such patients may be selected for various treatment regimens depending on prognosis as indicated by such MSH2 expression.

General methods in molecular genetics and genetic engineering useful in the present invention are described in the current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found in Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al. eds., Wiley & Sons.). Reagents, cloning vectors, and kits for genetic manipulation are available from commercial vendors such as BioRad, Stratagene, Invitrogen, ClonTech, and Sigma-Aldrich Co.

Cell culture methods useful in the present invention are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Other relevant texts are Creating a High Performance Culture (Aroselli, Hu. Res. Dev. Pr. 1996) and Limits to Growth (D. H. Meadows et al., Universe Publ. 1974). Tissue culture supplies and reagents are available from commercial vendors such as Gibco/BRL, Nalgene-Nunc International, Sigma Chemical Co., and ICN Biomedicals.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and" and "the" include plural references unless the context clearly dictates otherwise. All technical and scientific terms used herein have the same meaning.

Publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Isolation and Culture of HIPEC and HITEC Lines 1.1. Isolation of Human Gastrointestinal Segment-Specific Stem-Cell-like Progenitor Cells and Establishment of Epithelial Cell Lines in Long Term Culture Human intestinal primary epithelial cell lines (HIPEC) and human intestinal tumor-acquired epithelial cell lines (HITEC) are derived from gastrointestinal epithelial stem cell-like progenitor cells obtained from normal colon epithelium and from cancerous colon epithelium. Normal intestinal epithelial cells (IECs) are obtained from patients with colon cancer using surgical specimens excised at least 10 cm away from the tumor. Cancer tissue IECs are excised from the same patient. Both surgical specimens are made available from the Departments of Surgery and Pathology at the Robert Wood Johnson University Hospital.

1.1(a) Tissue Isolation

Surgical specimens of tissue are transported from an operating room to the laboratory within 30 minutes of surgery. The specimens are rinsed vigorously in sterile phosphate buffered saline (1×), pH 7.4 (PBS) to remove loosely adherent material, gently rubbed with sterile gauze, and washed at least ten times in PBS supplemented with antibiotic and antimycotic (1% penicillin/streptomycin) (ICN Biomedical, Costa Mesa, Calif.) ("supplemented PBS").

The mucosa is stripped off by careful dissection from the underlying submucosa and minced into small pieces (Panja, A. Lab. Invest. 2000. 80:9; 1473-1475, incorporated herein by reference in its entirety). Tissue pieces are treated with 1 mM dithiothreitol for 15 minutes (Sigma Chemical Co., St. Louis, Mo.) in RPMI 1460 (Gibco).

1.1(b) Generation of Mucosal Tissue Derived Growth Supporting Factors (MTD-GSF)

A portion (approximately 5 grams or one-third of the specimen) of the mucosal tissue pieces is cultured (250 mg/ml) overnight in serum free minimum essential medium (MEM) to generate culture supernatants containing autologous growth factor(s)/cytokines that mimic the cytokine milieu of the mucosal site. The collected supernatant is diluted in F-12 medium (Gibco/Invitrogen, Carlsbad, Calif.) and supplemented with hydrocortisone (5 µM), transferin (50 µg/ml), insulin (0.2 µg/ml), epidermal growth factor (5 ng/ml), and retinoic acid (25 µg/ml) (Sigma-Aldrich, St. Louis, Mo.).

1.1(c) Cell Isolation

The remaining tissue pieces are processed for isolation of surface and crypt epithelial cells by using sequential protease (dispase) treatments.

Mucosal tissue segments are treated with dispase (0.5 mg/ml in RPMI 1406 (Invitrogen, Carlsbad, Calif.)) solution for up to five treatments (5 minutes for the first treatment, 30 minutes for second and third treatments, then 40 minutes each for the next two treatments) to obtain intestinal epithelial cells (IECs). At each interval, sample tissue (for histological examination to detect the disappearance of surface epithelium and subsequent crypt cell liberation) and cell suspensions are collected (Panja et al. J Immunol 161.3675-84.1998). Epithelial cells are separated by percoll density gradient, and the purity of IECs is evaluated by staining with anti-CD3, CD14, CD20, CD45 mAbs and anti-cytokeratin-18 antibody (Panja et al. J Exp Med 178.1115-9.1993; Panja, Barone and Mayer J Exp Med 179.943-50.1994). Only cell preparations having greater than 95% viability will be used in the experiments. The IECs from fourth and fifth dispase treatments are used as a source of gastrointestinal segment-specific stem-cell-like progenitor cells for the generation of normal and diseased (e.g. colon cancer, ulcerative colitis, Crohn's disease, Barrett's esophagitis, gastric cancer, esophageal cancer, celiac disease, irritable bowel syndrome etc.) primary epithelial cell lines.

1.1(d) Formation of Bio-Similar-Matrix-Environments (BSMEs) on Plastic Surfaces

The de-epithelialized mucosal tissues remaining after the dispase treatment are collected and homogenized in PBS (1 ml/1 mg tissue). A cocktail of protease inhibitors, which includes PMSF (1 mM), Aprotinin (0.15 Units/ml), Lenpeptin (5 µg/ml), Pepstatin (1 µg/ml) and fluoride (1 mM), are added to the homogenate (0.5 ml of protease inhibitor cocktail for 20 grams of tissue lysate) to prevent degradation of matrix protein substances that may provide anchorage and/or support for epithelial growth. This mucosal tissue homogenate is diluted to 1 mg/ml in RPMI medium (Invitrogen, Carlsbad, Calif.) and used to coat the surfaces of plastic Petri dishes for 30 minutes to form a bio-similar-matrix-environment (BSME) on the plastic surface. The resulting BSME facilitates the attachment and growth of the isolated gastrointestinal stem-cell-like progenitor cells. Colon-BSME is supplemented with growth supporting factors derived from the mucosal tissues of the colon; and rectum-BSME is supplemented with growth supporting factors derived from the mucosal tissues of the rectum.

Isolated gastrointestinal stem-cell-like epithelial progenitor cells, are cultured for 24 hours in F-12 medium (Mediatech, Inc., Manassas, Va.) (1×106 cells/ml) supplemented with MTD-GSF (10%) on the appropriate BSME. Each of the isolated stem-cell-like progenitor cells are seeded onto the appropriate media. Thus, the stem-cell-like progenitor cells isolated from the colon are seeded onto colon-BSME; and the stem-cell-like progenitor cells isolated from the rectum are seeded onto rectum-BSME.

Figure 2:
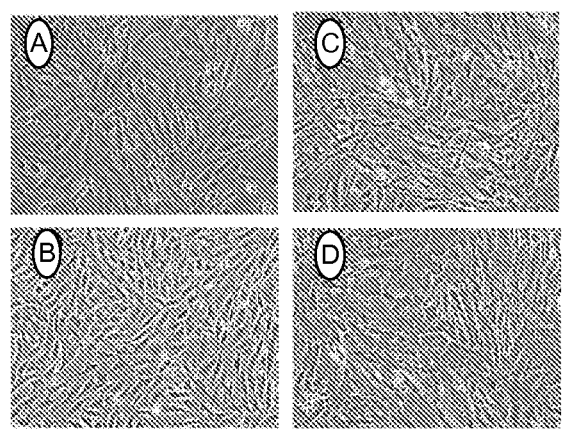
FIG. 2 shows light photomicrographs of one embodiment of primary epithelial monolayers derived from stem-cell-like progenitor crypt cells isolated from various segments of the human gastrointestinal tract of different subjects. (A) ascending colon segment; (B) transverse colon segment; (C) sigmoid segment, derived from normal portion of sigmoid resected from a patient with colon cancer; (D) rectum segment.

FIG. 2 shows light photomicrographs (Zeiss axiovert) of representative primary epithelial monolayers from stem cells isolated from the (a) ascending colon; (b) transverse colon, (c) sigmoid colon, and (d) rectum. Monolayers from all colonic HIPEC lines had similar morphology with polygonal shape with slight variations among each other. Without being limited by theory, the variance in morphology may represent an actual regional difference or may relate to the age or density of the cells in culture. The HIPEC monolayers are detached easily from the plastic surface and can be subjected to multiple passages (up to 24 passages in cases of normal tissue derived cells) allowing up to $165 \times 10^9$ cells in 18-24 passages to be obtained. A portion of each HIPEC line from each passage is kept frozen in multiple aliquots and the capacity to grow in culture after thawing was tested. The defrosted cells from each passage were capable of growing in secondary cultures.

Figure 6:
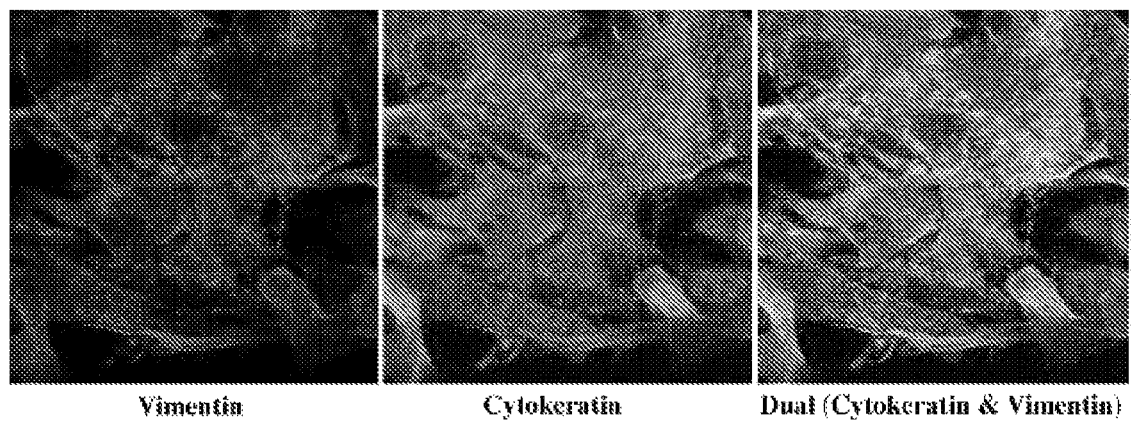
FIG. 6 shows that dual immunofluorescence staining of HIPECs derived from a patient with antibodies against vimentin (red) (marker for mesenchymal origin) and cytokeratin 18 (green) (marker for epithelial origin) demonstrated the presence of both of these lineage markers at the initial stage (between passage 2-3) of culture.
Figure 7:
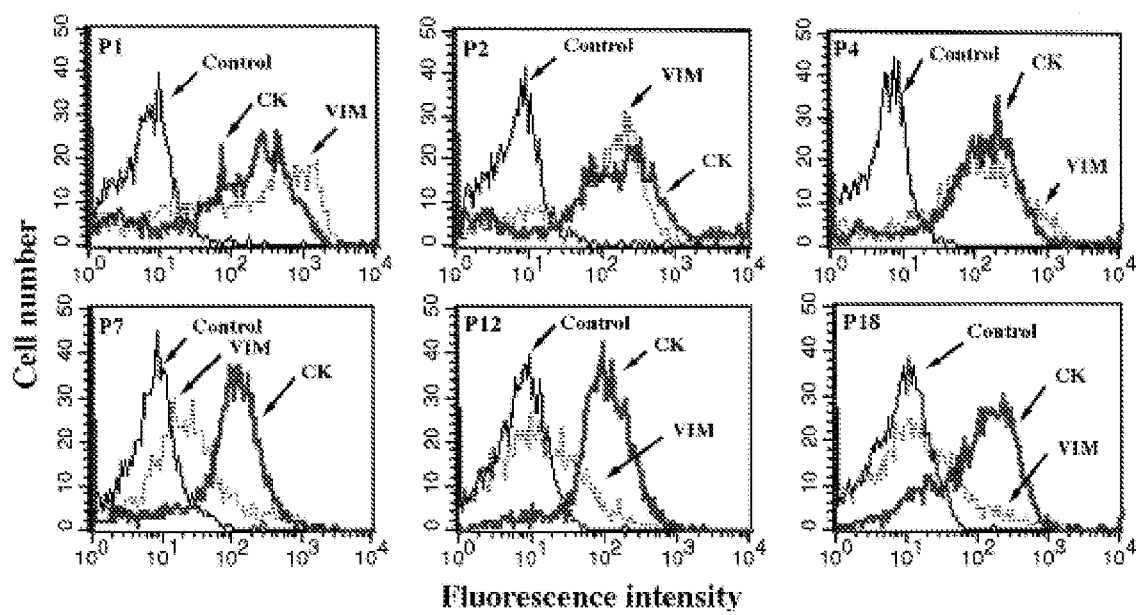
FIG. 7 shows a flow cytometric analysis of cytokeratin 18 (an epithelial marker) and vimentin (a mesenchymal marker) expression on HIPECs from different patients at various stages (passages 1-18) of cell growth.

FIG. 6 and FIG. 7 show the stem cell nature of the isolated cells which can be programmed to lose the mesenchymal marker (vimentin) and to retain the epithelial lineage property of cytokeratin expression. Further, this epithelial lineage may be conditioned to differentiate into at least 4 subtypes of epithelial cells (columnar, goblet, entero-endocrine and Paneth).

Example 2

Proof of Epithelial Origin of HIPEC Lines 2.1(a) Cytokeratin 18 Staining

Cells of epithelial origin are known specifically to contain cytoskeletal keratin. The intermediate filament system of intestinal epithelial cells in vivo contains cytokeratin 18 and 8. In order to confirm the epithelial origin of the HIPEC cells in culture, these cells are stained with an antibody (anti-cytokeratin 18) against one of the two intestinal epithelial filament proteins.

Gastrointestinal stem-cell-like progenitor cells, as isolated in Example 1 (see above), are grown on cover slips (Fisher Scientific). After permeabilization and fixation, cells are stained with anti-CK-18 antibody. The cover slips are washed three times in PBS/BSA and subsequently fixed in cold methanol at −20° C. for 10 minutes. The coverslips then are incubated in 2% FCS/PBS for 5 minutes. A FITC conjugated antibody against anti-human cytokeratin (Sigma) is used to detect the presence of cytokeratin and is incubated for 45 minutes followed by washings with 1% PBS/BSA.

Figure 3:
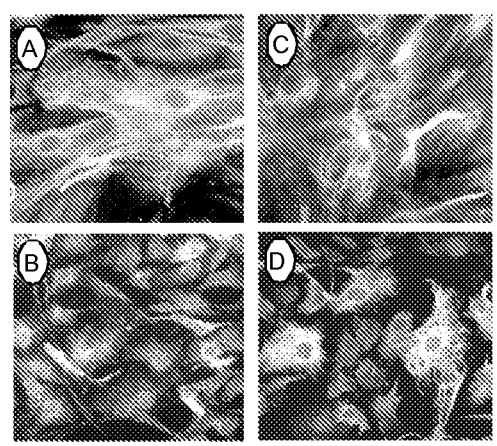
FIG. 3 shows primary cell culture derived from isolated stem-cell-like progenitor cells derived from different subject's (A) ascending colon segment; (B) transverse colon segment; (C) sigmoid segment, derived from normal portion of sigmoid resected from a patient with colon cancer; (D) a rectum segment grown on mucosal derived matrix coated plastic surface in culture stained with anti-cytokeratin-18 antibody. Expression of cytokeratin-18 is present in 100% of cells.

As shown in FIG. 3, expression of the CK-18 is present (green fluorescence) in about 100% of cells of the monolayer as confirmed by fluorescence microscopic analysis.

2.1(b) Flow Cytometric Analysis of Secretory Component (SC), Von Willebrand's Factor (VWF), and Carcinoembryonic Antigen (CEA) Expression by HIPEC Lines.

Dissociated cells from HIPEC monolayers of ascending colon, transverse colon, sigmoid, and rectum are permeabilized by treatment with permeafix (for CEA and VWF) and stained (FIG. 4) with an anti-CEA (right panel—green lines), anti-VWF (middle panel—green lines), or control antibody (black lines). For the detection of SC, staining is performed on unpermeabilized cells with an anti-SC antibody (left panel—blue lines) or an isotype control (left panel—black lines).

Figure 4:
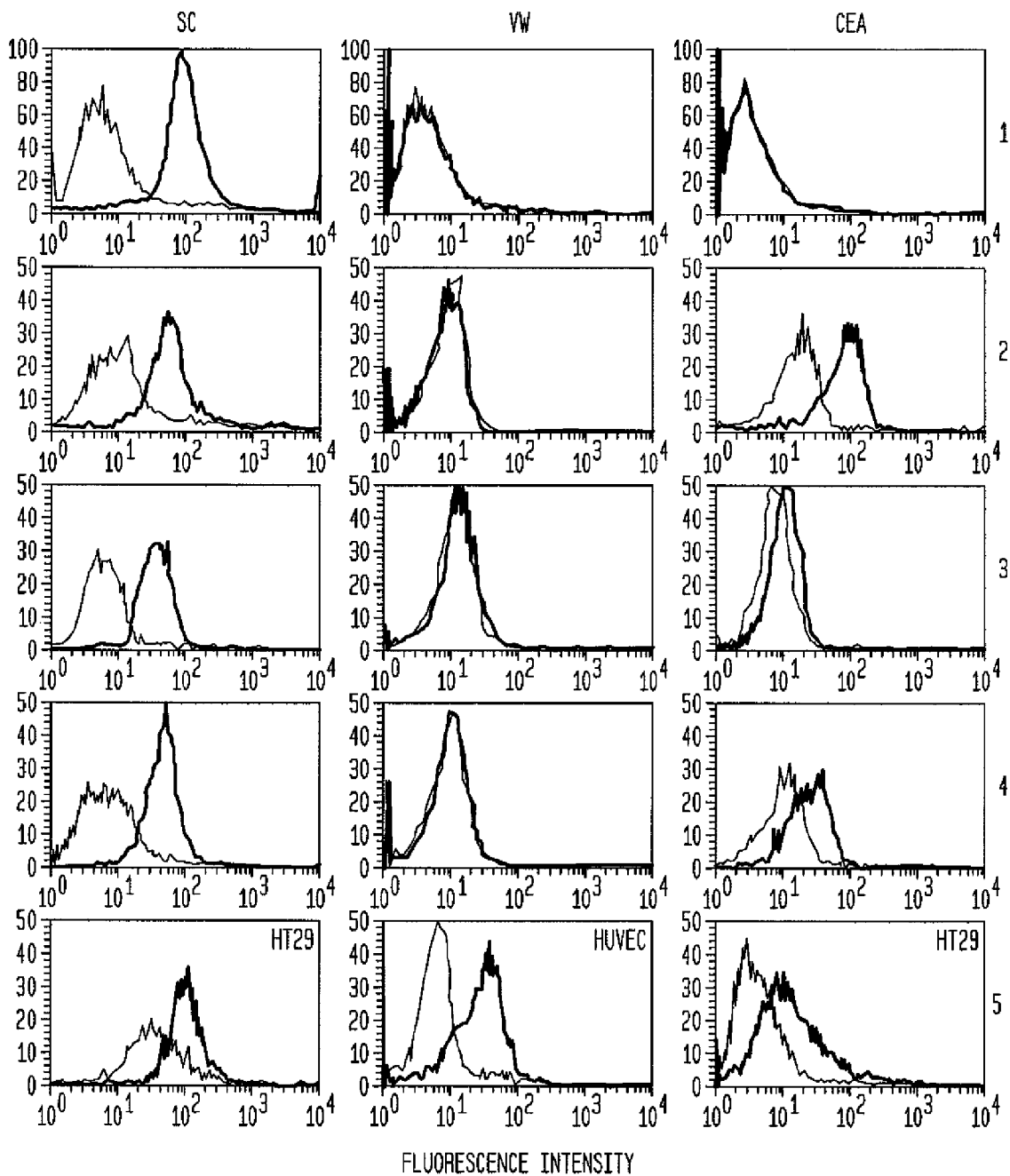
FIG. 4 shows flow cytometric analysis of secretory component (SC), von Willebrand's Factor (VWF), and carcinoembryonic antigen (CEA) expression by HIPEC lines derived from different subjects. Dissociated cells from HIPEC monolayers of ascending colon, transverse colon, sigmoid, and rectum were permeabilized by treatment with permeafix (for CEA and VWF) and stained with anti-CEA (right panel—green lines), anti-VWF (middle panel—green lines) or control antibody (black lines). For the detection of SC, staining was performed on unpermeabilized cells with an anti-SC antibody (left panel—blue lines) or an isotype control (left panel—black lines). All HIPEC lines were positive for secretory component (left panel) and negative for VWF (middle panel) and SMC (data not shown). Variable level of CEA expression (middle panel) was seen in all colonic HIPEC lines). 1=ascending colon; 2=transverse colon; 3=sigmoid; 4=rectum; 5=control cell line.

FIG. 4 shows that all HIPEC lines are strongly positive for secretory component (SC), usually expressed only in the epithelial cells (FIG. 4 left panel). They also express, to a varying degree, carcinoembryonic antigen (CEA), another specific marker for intestinal epithelial cells (FIG. 4 middle panel). All HIPEC lines are negative for Von-Willebrand's Factor, a marker for cells of endothelial origin (FIG. 4 right panel) and SMC (data not shown). Variable levels of CEA expression (middle panel) are seen in all colonic HIPEC lines.

Example 3

Characterization of HIPEC Lines 3.1. Morphology

The morphology of the HIPEC cell lines is examined using light microscopy. The epithelial origin of the cells is confirmed by staining with anti-cytokeratin 18. Electron microscopy is used to evaluate the ultrastructural characteristics of the cells. The cells were found to have a structural organization typical of intestinal epithelial cells as well as microvilli found at the apical membrane and a basement membrane formed at the base of the monolayer.

3.2. HIPEC Lines are Non-Transformed

Soft agar was prepared as follows: a) 1% agarose solution (5 ml) was added into a 10 cm² petri dish until the plate was completely covered; b) the agarose was pipetted off leaving a thin film of agarose on the bottom of the petri dish; c) after drying the plate for 20 minutes with the lid on, 10 ml of cell suspension ($0.5 \times 10^6$) was added on the top of the agarose film; d) medium was replaced every 4-5 days. Suspensions (2.0 ml) of normal HIPEC and control HT-29 cells were grown on soft agar medium for 3 weeks. The culture dishes were stained with 0.1% crystal violet for 5 minutes, destained, and photographed.

Figure 5:
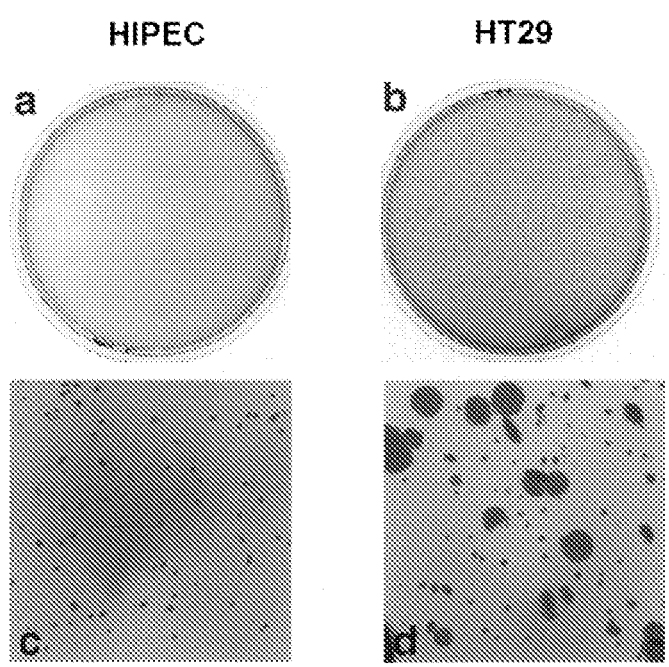
FIG. 5 shows HIPEC lines derived from a patient that were grown on soft agar, stained with 0.1% crystal violet, destained, and photographed (10× magnification). A) and C) normal colonic HIPEC line; B) and D) control malignant colonic epithelial cell line HT29. No growth is observed on A) and C); foci formation and cell growth were observed on B) and D).

FIG. 5 shows that normal colonic HIPEC lines (a, c), failed to grow in this medium, while foci formation and cell growth was observed in the cultures with control malignant colonic epithelial cell line HT-29 (b, d).

A karyotype analysis of the HIPEC cells revealed no chromosomal abnormalities.

These results confirm that the HIPEC lines do not possess a transformed phenotype or malignant nature, and thus are non-transformed.

Example 4

Establishment of a Model System to Compare Functional and Genotypic Differences Between Affected and Unaffected Epithelium of Patients Suffering from Colorectal Cancer (CRC)

Multiple pairs (normal and diseased) of HIPEC and HITEC lines will be generated from the gastrointestinal epithelium of individuals affected by a cancer, such as an esophageal cancer, a gastric cancer, and a colorectal cancer ("affected epithelium") and from the epithelium from the same regional segment of the GI tract unaffected by cancer ("unaffected epithelium") for the identification of molecular biomarkers and for study of the pathophysiological mechanisms of cancerous development in the human GI tract. As used herein, the term "unaffected epithelium" refers to epithelium that is at least 10 cm away from the tumor. Such multiple lines will aid in identifying and separating markers specific to disease from inherent normal variations in expression patterns between individuals and their conditions.

In order to ensure the reliability of data used to identify the differences between normal and CRC epithelium, each HIPEC lines will be fully characterized as follows:

a) Demonstration of uniform morphology: One of the decisive criteria for HIPECs to be considered as epithelial cells is a demonstration of typical morphological features, such as a polygonal shape. The morphology of HIPEC lines will be examined and photographed under light microscopy and DIC interference contrast (DIC) microscopy using a Zeiss Axiovert 25 inverted microscope equipped with a digital imaging system.

b) Demonstration of ultrastructural features typical of epithelial cells, including: microvilli, tight junctions, and microfilaments: Ultrastructural studies will be carried out utilizing a Jeol JEM-1200EX electron microscope. Confluent monolayers grown on collagen coated transwell nylon membranes (Costar) will be fixed with 3% glutaraldehyde in 0.1M PBS, pH 7.2, at 4° C. for 1 hour and post fixed in 1% osmium tetroxide. After dehydration in ethanol, the samples will be embedded in Epon. Thin sections will be stained with uranyl acetate and lead citrate. In some cases, embedded monolayers will be reembedded and sectioned perpendicularly.

c) Expression of junctional complex proteins, such as E-cadherin, β-catenin, and Tight junction protein ZO-1 (Zonula occludens protein 1, ZO-1): One of the unique features of epithelial cells is their ability to form tight junctions between the cells. Demonstration of the presence of junction complexes in HIPEC monolayers will confirm their epithelial identity, and validate use of this cell system for barrier function studies.

Analysis of junction protein expression will be carried out by both immunohistochemical and western blot analysis. For western blot analysis, cell lysate samples (containing 25 µg (for β-catenin), 50 µg (for ZO-1) and 80 µg (for E-cadherin) of protein per lane) will be run on a 7.5% SDS-polyacrylamide gel under reducing conditions. After 2 hours of electrophoresis at 200 volts in Laemmli running buffer, the proteins will be transferred to nitrocellulose by electroblotting in 25 mM Tris, 192 mM glycine and 20% methanol transfer buffer. Proteins on the nitrocellulose will be detected after 1 hour of blocking in 10% non-fat dry milk. The blot then will be incubated with primary antibodies (Transduction Laboratories). After overnight incubation, the blot will be washed extensively in TBS-Tween followed by incubation with an HRP-conjugated sheep anti-mouse immunoglobulin (Amersham, Piscataway, N.J.) for 1 hour. The blot will be washed and signals will be detected on a X-ray film by enhanced chemiluminescence (Amersham).

The expression of junction proteins by all cells in the monolayer will be confirmed immunohistochemically. Subconfluent monolayers of HIPEC lines will be grown on glass cover slips (Fisher Scientific), washed three times in PBS/BSA and subsequently fixed in cold methanol at −20° C. for 10 minutes. The coverslips will be incubated in 2% FCS/PBS for 5 minutes. Primary antibodies against anti-human E-cadherin (Transduction Laboratories), β-catenin (Transduction Laboratories, San Diego, Calif.) or an appropriate isotype-matched control antibody will be added and incubated at 4° C. for 1 hour. FITC-conjugated goat anti-mouse immunoglobulins used as secondary antibodies will be incubated for another 1 hour. Between each incubation the coverslips will be rinsed with cold PBS.

d) Expression of epithelial specific markers, such as cytokeratin, secretory component (SC), carcinoembryonic antigen (CEA), and intestinal alkaline phosphatase:

Expression of cell type specific cytoskeletal protein will be determined by intracellular staining with monoclonal antibodies (mAbs) against cytokeratin-18 (Sigma), or an appropriate isotype control antibody. Cells will be dissociated with trypsin, then permeabilized and fixed by incubation with permeafix (Ortho) for 1 hour at room temperature. Cells then will be washed twice with PBS/BSA and resuspended at $4 \times 10^6$ cells/ml. A 25 µl fraction of the suspension ($10^5$ cells) will be incubated at 4° C. for 45 minutes with an appropriate amount of antibody (as determined through serial dilution analysis with control cells). Either the above mentioned mAbs or an appropriate isotype control will be used. This will be followed by 3 washes with PBS/BSA and subsequent incubation of the cell suspension with FITC conjugated F(ab)'$_2$ goat anti-mouse IgG (except for cytokeratin, since the anti-cytokeratin is a FITC conjugated antibody) for another 45 minutes. After this second incubation, cells will be washed three times with PBS/BSA, resuspended in 200 µl of PBS and analyzed with a FACScan flow cytometer.

Immunohistochemical Detection of Epithelial Specific Markers Secretory Component (SC) and Carcinoembryonic Antigen (CEA): Expression of SC and CEA, combined with a lack of smooth muscle actin expression in these cells, will rule out contamination by myofibroblasts (Valentich et al. Am J Physiol 272.C1513-24.1997). Secretory component serves as a characteristic marker of epithelial cell type and indicates the differentiating stage of intestinal epithelium (glandular epithelium) (Ahnen, Brown and Kloppel Gastroenterology 89.667-82.1985; Brandtzaeg Histochem J 9.553-72.1977). The level of SC expression (high or low) in HIPECs (duodenum segment through rectum segment) will indicate the maturity (crypt or surface like cells) of the cells, which will be used in subsequent studies of IgA transport using the cell system of the present invention (Lamm et al. APMIS 103.241-6.1995).

Expression of epithelial cell specific surface molecules (CEA and SC) will be assessed by immunofluorescence staining using monoclonal antibodies (commercially available from SIGMA and DAKO, respectively) against these molecules. An unrelated control antibody will serve as a negative control. Additionally, to ascertain that HIPEC lines are not contaminated with smooth muscle or endothelial cells, the cells will be treated with an antibody directed to a marker for smooth muscle cells (anti-smooth muscle actin) and an antibody directed to a marker for endothelial cells (Von-Willebrand Factor). It is worth noting that that to our knowledge there is no specific marker for fibroblasts. Although there are cases in the literature where vimentin has been described as a marker for mesenchymal cells, recent data demonstrates that it is expressed by epithelial cells as well.

Dissociated HIPECs will be washed twice in PBS/BSA and then stained by the procedure described above. Stained cell suspensions will be analyzed on a flow cytometer (BD) gating on viable cells, as described in (Panja et al. J Immunol 161.3675-84.1998; Martin and Panja Am J Physiol Gastrointest Liver Physiol 282.G92-G104.2002), incorporated herein by reference in its entirety. Mean channel fluorescence, which correlates with fluorescence intensity, will be determined from the peak of positively stained cells and will be recorded on a log scale.

e) Obtain evidence of cytokine production and receptor expression (IL-6, IL-8, IL-10, GM-CSF, Gro-α, and TGF-β): Tests to determine the cytokine production ability of the cell system of the present invention will validate the functional properties of the cell system model. Intestinal epithelial cells (IECs) are considered as potential antigen presenting cell (APC) participants in mucosal immunoregulatory events. One general property of an APC is its ability to produce regulatory or accessory cytokines. The terms "regulatory cytokine" and "accessory cytokine" are used interchangeably herein to refer to cytokines that can either enhance T cell activation, inhibit T cell activation, or are proinflammatory; these cytokines include, but not limited to, IL-1, IL-6, TNF-α, IL-10, TGF-β, IL-8, Gro-α, MCP-1, and MIP-1α. IECs also are capable of cytokine production. Several studies have shown that intestinal epithelial cells are capable of producing many of the cytokines (IL-6, GM-CSF) known to be associated with enhanced APC function in conventional APCs. However, the cytokine profile of IECs differs from conventional APCs in that they fail to produce IL-113 (Panja, Siden and Mayer Clin Exp Immunol 100.298-305.1995), a cytokine believed to be important for T cell activation.

HIPECs derived from each segment of the intestine will be seeded at a concentration of 100,000 cells/ml/well in 24 well plates and cultured in serum free HIPEC medium for 24 hours at 37° C. Culture supernatants will be centrifuged and filtered through a 0.25 µm filter and kept frozen at −20° C. until assayed. The cytokine content of culture supernatants will be measured using quantitative ELISA kits following the manufacturers' directions (Immunotech, for IL-6, and R & D Systems for IL-8, GM-CSF, and Gro-α). Briefly, about 50 µl to about 200 µl of a standard or a test sample (HIPEC supernatant) will be added to ELISA wells (are coated with a specific cytokine antibody) in duplicate and incubated at room temperature for 2 hours. ELISA wells then will be washed 3 times in kit wash buffer, and the appropriate substrate or cytokine conjugate then will be added to each well. The ELISA wells will be washed again after 2 hours of incubation. The color development reaction will be stopped after 15 minutes and the intensity of the color will be measured by reading the absorbance at 405 nM. The sensitivity for IL-6 is 3 pg/ml, for IL-8 10 pg/ml, for GM-CSF 0.5 pg/ml and for Gro-α 10 pg/ml.

4.1. Cytokine Production and T Cell Activation by Paired HIPEC Lines:

Intestinal epithelial cells (IECs) play a critical role in immune response regulation by cognate interactions (meaning these mediated through surface molecules) as well as non-cognate interactions (meaning the mediated through soluble factors/cytokines) in the intestine. Altered cytokine production may lead to an active immune response in the mucosal environment leading to inflammation and tissue destruction. Previous studies from a number of laboratories have shown that multiple cytokines are produced in the mucosa (Podolsky J Gastroenterol 32.122-6.1997; Fiocchi Am J Physiol 273.G769-75.1997; Panja and Mayer Baillieres Clin Gastroenterol 10.407-25.1996). These operate as a cytokine network in a redundant, overlapping and synergistic fashion. Because pathophysiological consequences may result from the unregulated action or inappropriate production of particular cytokines, the levels of immunoregulatory and proinflammatory cytokine production by HIPEC lines derived from patients with CRC and from normal controls will be measured to determine the extent to which epithelial cells contribute to the altered cytokine concentration seen in CRC mucosa. The constitutive secretion level of proinflammatory and anti-inflammatory/inhibitory cytokines in HIPEC cultures will be measured using direct binding ELISA kits (R & D Systems); these cytokines include, but are not limited to, IL-6, IL-8, GM-CSF, TNF-α, IL-10, and TGF-β. Levels of cytokine production in affected cell lines will be compared and contrasted to levels of cytokine production in unaffected cell lines.

Previous studies with freshly isolated IECs have shown that production of several cytokines (GM-CSF and IL-8) is significantly increased in IBD (Panja Gastroenterology (abstract) 106(4):A750.1994). However, freshly isolated CRC cells often are contaminated with other cell types, making it difficult to interpret the results.

Cytokine production by unaffected (HIPEC) and affected (HITEC) CRC cell lines will provide more reliable information about the contribution of intestinal epithelial cells to cancer-induced inflammatory states.

Non-transformed HIPEC lines, which represent a system more comparable to physiological conditions, will be used to measure the level of production of several cytokines (GM-CSF and IL-8) in CRC. The presence of immunophenotypic/genotypic alterations also will be identified.

Table 1 shows altered genes in HITEC compared to normal counterpart HIPEC. The cytokine profile of normal HIPEC lines is similar to what has been observed in freshly isolated IECs.

TABLE 1

Altered Gene Expression in HITEC Relative to HIPEC Lines

| UniGene Symbol | Gene Description | Fold-increased | Fold-decreased |
|---|---|---|---|
| PMPCB | peptidase (mitochondrial processing) beta | | 4.04 |
| GTPBP1 | GTP binding protein 1 | 2.16 | |
| RAB2 | RAB2, member RAS oncogene family | | 2.25 |
| PSMB6 | proteasome (prosome, macropain) subunit, beta type, 6 | | 2.38 |
| PSMD8 | proteasome (prosome, macropain) 26S subunit, non-ATPase, 8 | | 2.09 |
| TIMP3 | tissue inhibitor of metalloproteinase (Sorsby fundus dystrophy, pseudoinflammatory) | 8.51 | 0.12 |
| ECM1 | extracellular matrix protein 1 | | 3.15 |
| BRCA1 | breast cancer 1, early onset | | 5.69 |
| CRKL | v-crk avian sarcoma virus CT10 oncogene homolog-like | | 5.98 |
| D10S170 | DNA segment, single copy, probe pH 4 (transforming sequence, thyroid-1 | | 3.48 |
| COL1A2 | collagen, type I, alpha 2 | | 3.42 |
| FXR2 | fragile X mental retardation, autosomal homolog 2 | | 2.08 |
| SCA2 | spinocerebellar ataxia 2 (olivoponotcerebellar ataxia 2, autosomal dominant, ataxin 2) | | 2.22 |
| ADAM20 | a disintegrin and metalloproteinase domain 20 | | 2.09 |
| STX3A | syntaxin 3A | | 4.23 |
| WISP1 | WNT1 inducible signaling pathway protein 1 | 2.05 | |
| CLN2 | ceroid-lipofuscinosis, neuronal 2, late infantile (Jansky-Bielschowsky disease) | 2.18 | |
| KCNS3 | potassium voltage-gated channel, delayed-rectifier, subfamily S, member 3 | 52.41 | |
| MKI67 | antigen identified by monoclonal antibody Ki-67 | | 12.25 |
| NAPTB | Neuronal adaptin-like protein, beta-subunit | 11.98 | |
| CACNA1E | calcium channel, voltage-dependent, alpha 1E subunit | 121.38 | |
| ITGA7 | integrin, alpha 7 | 4.82 | |
| MLH1 | mutL (E. coli) homolog 1 (colon cancer, nonpolyposis type 2) | | 2.57 |
| MSH2 | mutS (E. coli) homolog 2 (colon cancer, nonpolyposis type 10 | | 5.14 |
| MYBL1 | v-myb avian myeloblastosis viral oncogene homolog-like 1 | | 31.26 |
| SCYA20 | small inducible cytokine subfamily A (Cys-Cys), member 20 | 6.66 | |
| MADCAM1 | mucosal vascular addressin cell adhesion molecule 1 | 2.41 | |
| NPAS1 | neuronal PAS domain protein 1 | 3.08 | |
| API2 | apoptosis inhibitor 2 | | 5.14 |
| BCL2L1 | BCL2-like 1 | | 2.01 |
| SACM2L | suppressor of actin mutations 2, yeast, homolog-like | | 7.02 |
| AQP2 | aquaporin 2 (collecting duct) | 2.59 | |
| BNIP1 | BCL2/adenovirus E1B 19 kD-interacting protein 1 | 2.74 | |
| RARB | retinoic acid receptor, beta | 17.71 | |
| K-ALPHA-1 | tubulin, alpha, ubiquitous // Dilution 1:625 | 2.02 | |
| IL13RA1 | interleukin 13 receptor, alpha 1 | 2.49 | |
| IL18R1 | interleukin 18 receptor 1 | 4.42 | |
| TTC1 | tetratricopeptide repeat domain 1 | | 7.10 |
| GAPD | glyceraldehyde-3-phosphate dehydrogenase // Dilution 1:25 | 2.19 | |
| PCSK5 | proprotein convertase subtilisin/kexin type 5 | 148.52 | |
| PCSK7 | proprotein convertase subtilisin/kexin type 7 | | 2.45 |

TABLE 1-continued

Altered Gene Expression in HITEC Relative to HIPEC Lines

| UniGene Symbol | Gene Description | Fold-increased | Fold-decreased |
|---|---|---|---|
| ALCAM | activated leucocyte cell adhesion molecule | | 2.28 |
| BST1 | bone marrow stromal cell antigen 1 | | 2.18 |
| MSLN | mesothelin | | 12.92 |
| PSMC2 | proteasome (prosome, macropain) 26S subunit, ATPase, 2 | | 2.20 |
| RASA1 | RAS p21 protein activator (GTPase activating protein) 1 | | 4.55 |
| RGS10 | regulator of G-protein signalling 10 | | 2.71 |
| ELAVL3 | ELAV (embryonic lethal, abnormal vision, *Drosophila*)-like 3 (Hu antigen C) | | 2.28 |
| SPC18 | signal peptidase complex (18 kD) | | 8.42 |
| HLA-B | major histocompatibility complex, class I, B | | 2.41 |
| X | HLA-DR alpha-chain | | 11.77 |
| DCC | deleted in colorectal carcinoma | | 4.26 |
| FXR1 | fragile X mental retardation, autosomal homolog 1 | | 5.37 |
| SOX9 | SRY (sex-determining region Y)-box 9 (campomelic dysplasia, autosomal sex-reversal) | | 2.20 |
| PCSK1 | proprotein convertase subtilisin/kexin type 1 | | 5.38 |
| CLIC2 | chloride intracellular channel 2 | | 2.37 |
| ADAM23 | a disintegrin and metalloproteinase domain 23 | | 5.75 |
| APAF1 | apoptotic protease activating factor | 2.98 | |
| STX5A | syntaxin 5A | | 482.28 |
| KCNJ1 | potassium inwardly-rectifying channel, subfamily J, member 1 | 2.21 | |
| PRSC1 | protease, cysteine, 1 (legumain) | 5.45 | |
| APLP2 | amyloid beta (A4) precursor-like protein 2 | 4.91 | |
| PRSS15 | protease, serine, 15 | 2.45 | |
| MIC2 | antigen identified by monoclonal antibodies 12E7, F21 and O13 | | 3.25 |
| NOVA1 | neuro-oncological ventral antigen 1 | | 2.89 |
| F12 | coagulation factor XII (Hageman factor) | | 2.66 |
| F13B | coagulation factor XIII, B polypeptide | 2.06 | |
| CLCN5 | chloride channel 5 (nephrolithiasis 2, X-linked, Dent disease) | | 4.70 |
| GLI | glioma-associated oncogene homolog (zinc finger protein) | | 2.17 |
| ITGA2B | integrin, alpha 2b (platelet glycoprotein IIb of IIb/IIIa complex, antigen CD41B) | | 8.31 |
| ITGAX | integrin, alpha X (antigen CD11C (p150), alpha polypeptide) | | 2.53 |
| MOS | v-mos Moloney murine sarcoma viral oncogene homolog | | 7.98 |
| SCYA21 | small inducible cytokine subfamily A (Cys-Cys), member 21 | | 2.68 |
| SCYA23 | small inducible cytokine subfamily A (Cys-Cys), member 23 | | 2.31 |
| NCAM1 | neural cell adhesion molecule 1 | 5.42 | |
| MYO9B | myosin IXB | | 2.27 |
| MJD | Machado-Joseph disease (spinocerebellar ataxia 3, olivopontocerebellar ataxia 3, autosomal dominant, ataxin 3) | | 7.49 |
| DDB1 | damage-specific DNA binding protein 1 (127 kD) | | 7.68 |
| IL6 | interleukin 6 (interferon, beta 2) | | 18.88 |
| IL15 | interleukin 15 | 4.03 | |
| CLN3 | ceroid-lipofuscinosis, neuronal 3, juvenile (Batten, Spielmeyer-Vogt disease) | 3.78 | |
| IL11RA | interleukin 11 receptor, alpha | | 4.20 |
| IL17R | interleukin 17 receptor | | 2.56 |
| YWHAZ | tyrosine 3-monooxygenase/tryptophan 5-monooxygenase activation protein, zeta polypeptide // Dilution 1:5 | | 2.05 |
| TTC2 | tetratricopeptide repeat domain 2 | | 5.38 |
| PKD2 | polycystic kidney disease 2 (autosomal dominant) | | 26.03 |
| PSMA5 | proteasome (prosome, macropain) subunit, alpha type, 5 | 12.76 | |
| RAB3B | RAB3B, member RAS oncogene family | | 117.44 |
| CAMLG | calcium modulating ligand | | 14.58 |
| CEACAM4 | carcinoembryonic antigen-related cell adhesion molecule 4 | | 10.46 |
| PSMD1 | proteasome (prosome, macropain) 26S subunit, non-ATPase, 1 | | 2.15 |
| PSMD4 | proteasome (prosome, macropain) 26S subunit, non-ATPase, 4 | 3.56 | |

TABLE 1-continued

Altered Gene Expression in HITEC Relative to HIPEC Lines

| UniGene Symbol | Gene Description | Fold-increased | Fold-decreased |
|---|---|---|---|
| RGS13 | regulator of G-protein signalling 13 | | 9.51 |
| RGS2 | regulator of G-protein signalling 2, 24 kD | | 16.16 |
| RGS4 | regulator of G-protein signalling 4 | | 2.42 |
| RIN1 | ras inhibitor | 2.40 | |
| GAGE5 | G antigen 5 | 2.30 | |
| GAGE7 | G antigen 7 | | 3.14 |
| EMP1 | epithelial membrane protein 1 | | 5.35 |
| CASP13 | caspase 13, apoptosis-related cysteine protease | | 2.60 |
| STXBP3 | syntaxin binding protein 3 | 4.88 | |
| CANPX | calpain-like protease CANPX | | 2.16 |
| CAPN5 | calpain 5 | 3.87 | |
| PLOD | procollagen-lysine, 2-oxoglutarate 5-dioxygenase (lysine hydroxylase, Ehlers-Danlos syndrome type VI) | | 2.15 |
| KCNJ13 | potassium inwardly-rectifying channel, subfamily J, member 13 | | 2.47 |
| ELA2 | elastase 2, neutrophil | 3.23 | |
| GZMB | granzyme B (granzyme 2, cytotoxic T-lymphocyte-associated serine esterase 1) | 15.34 | |
| MCC | mutated in colorectal cancers | 2.14 | |
| MYH9 | myosin, heavy polypeptide 9, non-muscle | 7.66 | |
| MYL1 | myosin, light polypeptide 1, alkali; skeletal, fast | | 6.23 |
| HRK | harakiri, BCL2-interacting protein (contains only BH3 domain) | 2.23 | |
| ARHGAP1 | Rho GTPase activating protein 1 | 2.26 | |
| G3BP | Ras-GTPase-activating protein SH3-domain-binding protein | | 5.70 |
| GNB3 | guanine nucleotide binding protein (G protein), beta polypeptide 3 | | 2.36 |
| IFNA2 | interferon, alpha 2 | 4.10 | |
| UBC | ubiquitin C | | 3.04 |
| HD | huntingtin (Huntington disease) | | 2.17 |
| MCF2 | MCF.2 cell line derived transforming sequence | 2.58 | |
| NAGLU | N-acetylglucosaminidase, alpha-(Sanfilippo disease IIIB) | 2.04 | |
| IL3RA | interleukin 3 receptor, alpha (low affinity) | | 2.90 |
| PRNP | prion protein (p27-30) (Creutzfeld-Jakob disease, Gerstmann-Strausler-Scheinker syndrome, fatal familial insomnia) | | 2.04 |
| GAPD | glyceraldehyde-3-phosphate dehydrogenase // Dilution 1:625 | 2.05 | |
| GAPD | glyceraldehyde-3-phosphate dehydrogenase | | 2.74 |
| KLK10 | kallikrein 10 | | 3.74 |
| RAB3A | RAB3A, member RAS oncogene family | | 2.89 |
| PSMD7 | proteasome (prosome, macropain) 26S subunit, non-ATPase, 7 (Mov34 homolog) | | 3.34 |
| RGS5 | regulator of G-protein signalling 5 | | 2.12 |
| ERG | v-ets avian erythroblastosis virus E26 oncogene related | | 4.41 |
| ETV6 | ets variant gene 6 (TEL oncogene) | 2.25 | 0.44 |
| ADAM3B | a disintegrin and metalloproteinase domain 3b (cyritestin 2) | | 6.05 |
| TSC1 | tuberous sclerosis 1 | | 2.24 |
| CAPN4 | calpain, small polypeptide | | 3.22 |
| PAH | phenylalanine hydroxylase | | 2.52 |
| SCYA3 | small inducible cytokine A3 (homologous to mouse Mip-1a) | | 11.78 |
| SCN4A | sodium channel, voltage-gated, type IV, alpha polypeptide | | 10.97 |
| MMP13 | matrix metalloproteinase 13 (collagenase 3) | | 2.69 |
| MMPL1 | matrix metalloproteinase-like 1 | | 15.02 |
| ICAM2 | intercellular adhesion molecule 2 | 2.98 | |
| M1S1 | membrane component, chromosome 1, surface marker 1 (40 kD glycoprotein, identified by monoclonal antibody GA733) | | 2.53 |
| MCF2 | MCF.2 cell line derived transforming sequence | | 3.43 |
| SCYA14 | small inducible cytokine subfamily A (Cys-Cys), member 14 | 3.10 | |
| SCYA17 | small inducible cytokine subfamily A (Cys-Cys), member 17 | 0.49 | 2.04 |
| SIP2-28 | calcium and integrin binding protein (DNA-dependent protein kinase interacting protein) | 3.30 | |
| NF2 | neurofibromin 2 (bilateral acoustic neuroma) | | 2.26 |
| NRAS | neuroblastoma RAS viral (v-ras) oncogene homolog | | 2.23 |

TABLE 1-continued

Altered Gene Expression in HITEC Relative to HIPEC Lines

| UniGene Symbol | Gene Description | Fold-increased | Fold-decreased |
|---|---|---|---|
| MYHL | myosin, heavy polypeptide-like (110 kD) | | 2.69 |
| CACNA1C | calcium channel, voltage-dependent, L type, alpha 1C subunit | | 3.03 |
| CACNA1E | calcium channel, voltage-dependent, alpha 1E subunit | | 3.00 |
| WNT1 | wingless-type MMTV integration site family, member 1 | | 2.38 |
| X | alkali myosin light chain 3 mRNA, complete cds | | 4.03 |
| GNG11 | guanine nucleotide binding protein 11 | | 18.99 |
| TNFRSF6 | tumor necrosis factor receptor superfamily, member 6 | | 2.04 |
| IL8 | interleukin 8 | | 27.07 |
| GJB5 | gap junction protein, beta 5 (connexin 31.1) | | 2.40 |
| UBC | ubiquitin C | 2.14 | 0.47 |
| HEXA | hexosaminidase A (alpha polypeptide) | | 13.38 |
| IGHG3 | immunoglobulin gamma 3 (Gm marker) | 2.83 | 0.35 |
| IL4R | interleukin 4 receptor | | 2.54 |
| YWHAZ | tyrosine 3-monooxygenase/tryptophan 5-monooxygenase activation protein, zeta polypeptide | | 13.92 |
| SNCA | synuclein, alpha (non A4 component of amyloid precursor) | | 9.28 | f) Evidence of non-transformed state by soft agar assay and karyotype analysis: The non malignant nature of the HIPEC lines will be demonstrated by soft agar assay, karyotype analysis, and by injection of these cell lines into nude mice.

Soft agar assay: A concentration of 2% agarose (Bacto agar DIFCO) will be prepared in DMEM medium at 40° C. and added to 100 mm culture dishes. The agar will be allowed to solidify in the incubator. A suspension (50,000 cells/ml in DMEM cell culture medium with 0.5% agarose) of normal HIPEC lines or control colonic adenocarcinoma cell line (HT-29) will be overlaid on the solidified agar layer. Plates will be incubated at 37° C. Liquid medium will be added 3 days after the incubation and renewed every 3 days. Cell growth will be observed for 3 weeks.

Karyotype analysis: HIPEC cells grown on in situ coverslips will be treated with colcemide (0.01 µg/ml) for 30 minutes. The cells will be subjected to hypotonic shock with 0.07M KCl for 30 minutes at 37° C. followed by fixation with methanol/glacial acetic acid (3:1). Chromosome preparations will be made by air dry method, giemsa banding, and karyotyping as described by Seabright et. al. (Seabright Lancet 2.971-2.1971).

4.2. Injections into Nude Mice:

g) Demonstration that cells are capable of being maintained in culture and in a cryofrozen condition for extended periods of time.

Epithelial cell lines derived from affected regions of CRC (HITEC; human intestinal tumorogenic epithelial cells) will be characterized in a similar fashion to the HIPEC lines as described above in Example 3. The non-transformed state assay will be omitted.

Example 5

Identification of Potential Therapeutic Targets and Treatment Efficacy Markers

It has been hypothesized that cellular, molecular, genetic, and functional changes in IEC are involved in CRC. A comparison of specific genes expression in affected and unaffected IEC may be important to understand mechanisms of the CRC for identification of genes for use as biomarkers, and for identification of potential therapeutic targets or treatment efficacy markers.

Paired nontransformed cell lines derived from the tumorous (HITEC) and normal (HIPEC) epithelium of the same patient with colorectal cancer have been used in pilot studies to identify differences in the morphology, function and gene expression of these epithelia.

5.1. Gene Array Analysis

An understanding of pathogenetic mechanisms of cancer in the human colonic epithelium have not progressed very far, at least in part because there has not been a comprehensive study comparing the genetic properties of paired epithelial cells originating from normal and tumorous colonic epithelium of the same individual.

According to the described invention, several paired HIPEC (normal) and HITEC (tumor) lines have been established from patients undergoing colon resection secondary to carcinoma and their morphologic and phenotypic characteristics, telomerase activity, and gene expression compared.

a) Gene array analysis was performed by microarray hybridization. Total RNA from confluent monolayers of HIPEC and HITEC were used for expression analysis of 1,154 genes (representing oncogenes/suppressors, matrix proteins, G proteins, receptors and channels, apoptosis/proteases and cytokines) by using the ExpressChip™ DNA microarray system (Mergen Ltd, San Leandro, Calif.).

5.2. RNA Isolation

Trizol (Gibco BRL) was added (5 ml/T75flask) to HIPEC monolayers on plastic surfaces and homogenized by Pasteur pipette followed by addition of 0.5 ml of chloroform with 4% isoamyl alcohol. After mixing, the suspension was placed on ice for 15 minutes and centrifuged at 12,000 RPM for 15 minutes. After centrifugation, the aqueous phase was transferred to a fresh tube; an equal volume of isopropanol was added, kept on ice for 15 minutes and centrifuged again at 12,000 RPM for 15 minutes. After removal of the supernatant, the RNA pellet was washed with 75% ethanol by vortexing and subsequent centrifugation for 8 minutes at 7,500 RPM. The pellet was then dried and dissolved in diethylpyrocarbonate (DEPC, Sigma) treated RNAse free sterile water. RNA concentration of all preparations was determined by measuring the absorbance at 260 nm/280 nm (260/280 ration). Only those samples with a 260/280 ratio greater than 1.9 were used for the experiments. Each RNA preparation was be checked for lack of degradation by mini-gel prior to the use for gene array analysis.

5.3. cDNA Synthesis and Microarray Hybridization

The ExpressChip DNA microarray system was used to perform the genetic analysis using the total RNA from confluent monolayers of both cell lines. Total cellular RNA (50 µg) was annealed to the oligo(dT) oligonucleotide and reverse-transcribed in the presence of Cy3-labeled (Control) or Cy5-labeled (experimental) dUTP (Amersham Pharmacia Biotech, Piscataway, N.J.), using 10,000 Units/ml of Superscript II reverse transcriptase (Life Technologies). The resulting Cy3- and Cy5-labeled cDNA was treated with RNase One (Promega, Madison, Wis.) for 10 minutes at 37° C., combined and purified by passing through a Centricon-50 filtration spin column (Millipore, Bedford, Mass.) to a final volume of 6.5 ml. The cDNA probes were combined with 32.5 ml of hybridization solution and 1.0 ml of blocking solution to a final volume of 40 ml. The probe mixture was heated at 94° C. for 2 minutes and then centrifuged at 11,500 g for 10 minutes. Next, the supernatant was transferred to a clean tube and incubated at 50° C. for 1 hour before hybridizing to the microarrays. Hybridizations were performed on cDNA microarray glass slides ExpressChip™ EO2 (Mergen Ltd, San Leandro, Calif.) consisting of 1,154 cDNAs representing families of cytokines/receptors, surface antigens, matrix metalloproteinases, proteases, and oncogenes. The hybridization solution (40 ml) was then placed on a pretreated (UV-cross linked) microarray slide, covered with a coverglass (60 mm) and incubated in a hybridization chamber overnight at 50° C. After hybridization, the slide was washed at room temperature, first with 0.2×SSC, 0.1% SDS for 20 minutes with gentle shaking, and then with 0.2×SSC twice (20 minutes each). The slide then was dried by spinning at low speed (150 g) in a centrifuge for 5 minutes and stored in a dark box free from dust.

5.4. Analysis of Gene Array Data

Slides were scanned using a microarray scanner. The final intensities of red and green channels were filtered and the ratio of the red to the green intensity was determined. cDNA microarray results were derived by comparing total RNA from HITECs (Cy5-labeled) vs. HIPECs (Cy3-labeled). These experiments were conducted in triplicate and the results were analyzed using GeneSpring software (Silicon Genetics, Redwood City, Calif.). To generate the relative intensity (ratio) values, each gene's measured intensity was divided by its control channel value in each sample. To correct for artifacts caused by nonlinear rates of dye incorporation as well as inconsistencies of the relative fluorescence intensity between some red and green dyes, an intensity-dependent normalization (Lowess normalization) was used. This normalization method fits a curve through the data and uses this curve to adjust the control value for each measurement. The average expression level of each gene in 2 groups was calculated with a cutoff value set to 1.7 or 0.5 for the ratio of median. Above 2 and below 0.5 were assigned as cutoff values, for up regulation of gene expression and/or down regulation of gene expression, respectively.

5.5. Results

Figure 9:
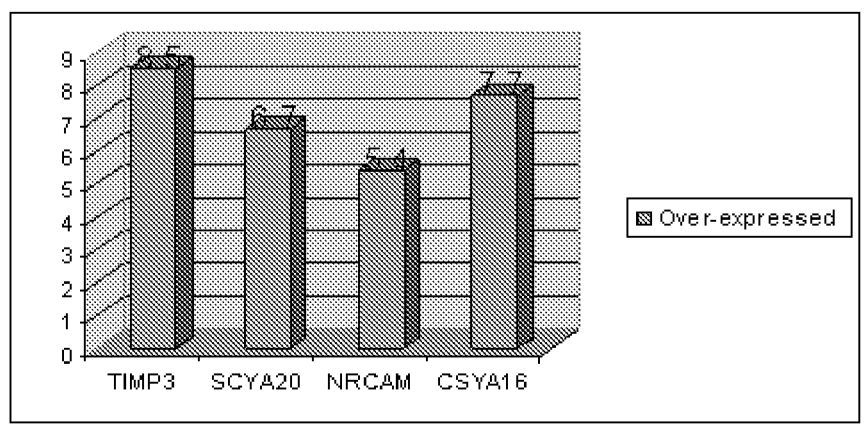
FIG. 9 shows a microarray analysis of over-expressed genes in tumor derived epithelial cells (HITEC) compared to their normal mucosa derived counterpart (HIPEC) from the same individual.
Figure 10:
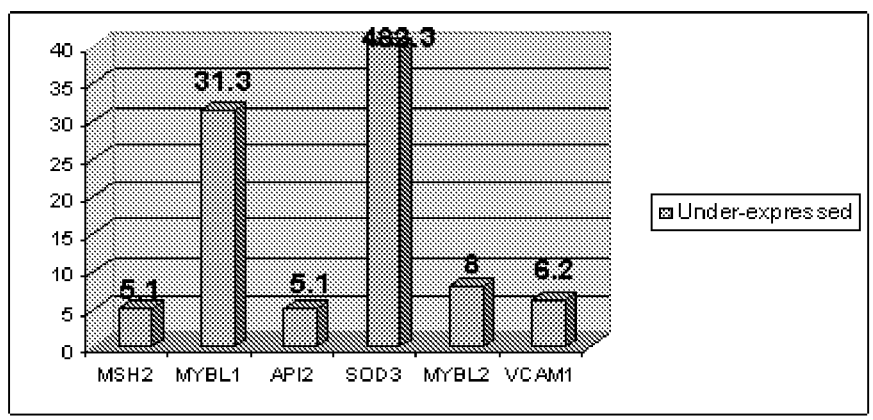
FIG. 10 shows a microarray analysis of under-expressed genes in tumor derived epithelial cells (HITEC) compared to normal mucosa derived counterpart (HIPEC) from the same individual.

The HITEC lines had aberrant expression of several genes in contrast to the HIPEC lines. The results of microarray analysis of over-expressed genes in HITEC compared to HIPEC from the same individuals are shown in FIG. 9. The results of microarray analysis of underexpressed genes in HITEC compared to HIPEC from the same individual are shown in FIG. 10. The data revealed that about 50 genes were upregulated and 106 genes were downregulated in each HITEC compared to its normal counterpart HIPEC (see Table 1). Table 2 and Table 3 show over-expressed genes and underexpressed genes in tissue from subjects with GI disorders with an increase in expression greater than 5-fold (i.e., S/C ratios >5, with at least one value above threshold; S=sample; C=control). Table 5 shows altered genes in CD; Table 6 shows altered genes in UC. Among the most abundantly increased (greater than 6 fold) transcripts were the TIMP3, MIP3a, and IL-10 inducible chemokine (SCYA16), retinoic acid receptor beta, RAB33 (RAS oncogene) (see Table 2, Table 5, and Table 6). Among the most underexpressed (at least 6 fold less than control) genes were interferon induced protein 56 (IFIT1), presenilin-2 (PSEN2), VCAM1, MYBL2, SOD3, RAN (RAS oncogene), and FOSL1 (see Table 2, Table 5, and Table 6).

TABLE 2

Genes over- and under-expressed in HITEC compared to the normal counterpart in HIPEC

| Gene | Over-expression (fold-increase) (S/C) | Under-expression (fold-decrease) (C/S) |
|---|---|---|
| MSH2 | | 5.1 |
| MYBL1 | | 31.3 |
| API2 | | 5.1 |
| SOD3 | | 482.3 |
| MYBL2 | | 8 |
| VCAM1 | | 6.2 |
| TIMP 3 | 8.5 | |
| SCYA20 | 6.7 | |
| NRCAM | 5.4 | |
| CSYA16 | 7.7 | |

Among the overexpressed (greater than 6-fold increase) genes were tissue inhibitor of metalloproteinase 3 (TIMP 3), small inducible cytokine subfamily member A 20, and small inducible cytokine family A member 16 (CSYA 16). TIMP 3, SCYA20, NCAM, and CSYA16 had 8.5, 6.7, and 7.7 fold increase in gene expression, respectively in comparison to HIPEC. The HITEC line also exhibited underexpression of several genes. Mutants (*Escherichia coli*) homolog 2 (MSH2), MYBL1, API2, SOD3, MYBL2, and VCAM1 showed a 5.1, 31.3, 5.1, 482.3, 8, and 6.2 fold decrease in expression compared to its normal counterpart.

TABLE 3

Over- and Under-expressed Genes in Gastrointestinal Disorders.

| Gene | Over-expressed Ratio S/C in Crohn's Disease | Over-expressed Ratio S/C in Ulcerative Colitis | Under-expressed Ratio S/C in Ulcerative Colitis | Under-expressed Ratio S/C in Crohn's Disease |
|---|---|---|---|---|
| SCYB6 | | 5.4 | | 5.1 |
| PSMB9 | | 6.4 | | |
| TNFAIP6 | | 6.7 | | |
| hla-f | | 6.8 | | |
| SCYA3 | | 14.2 | | |
| APOC1 | 26.9 | 31.3 | | |
| IFIT1 | | 35.9 | | |
| SCYA20 | 6.1 | 41.5 | | |
| GSTT1 | 123.4 | 58.4 | | |
| SCYA5 | | 64.9 | | |
| ARHI | | 74.8 | | |
| MMP1 | 42.7 | 122.6 | | |

TABLE 3-continued

Over- and Under-expressed Genes in Gastrointestinal Disorders.

| Gene | Over-expressed Ratio S/C in Crohn's Disease | Over-expressed Ratio S/C in Ulcerative Colitis | Under-expressed Ratio S/C in Ulcerative Colitis | Under-expressed Ratio S/C in Crohn's Disease |
|---|---|---|---|---|
| BST2 |  | 247.9 |  |  |
| IL1RL1 |  | 301.6 |  |  |
| PDCD2 | 5.8 |  |  |  |
| TIM | 6.4 |  |  |  |
| NPAS1 | 6.5 |  |  |  |
| ARHGAP5 | 7.1 |  |  |  |
| APBA2 | 8.0 |  |  |  |
| NRCAM | 9.0 |  |  |  |
| SFRP1 | 9.1 |  |  |  |
| IL18R1 | 9.5 |  |  |  |
| CACNA1H | 10.0 |  |  |  |
| ARHGDIB | 18.9 |  |  |  |
| PCSK5 | 35.5 |  |  |  |
| BST2 | 41.3 |  |  |  |
| EDIL3 | 60.1 |  |  |  |
| MET |  |  | 5.1 |  |
| CLU |  |  | 5.3 |  |
| HLA-DPB1 |  |  | 5.5 | 40.7 |
| IL18 |  |  | 5.9 | 11.6 |
| MM2 |  |  | 10.7 | 46.6 |
| HLA-B |  |  | 12.6 |  |
| ITGAV |  |  | 30.2 |  |
| SOD3 |  |  | 286.4 |  |
| MYLK |  |  |  | 6.2 |
| MYLB1 |  |  |  | 9.5 |
| RPL32 |  |  |  | 13.1 |
| COL7A1 |  |  |  | 31 |
| TNFSF10 |  |  |  | 47.8 |
| COL15A1 |  |  |  | 64.6 |
| API2 |  |  |  | 80.1 |

TABLE 5

Altered Gene Expression in Crohn's Disease Patients

| Unigene Symbol | Gene description | Over-expressed in CD (S/C) | Under-expressed in CD (C/S) |
|---|---|---|---|
| PDCD2 | programmed cell death 2 | 5.84 |  |
| NGAP | ras GTPase activating protein-like | 3.41 |  |
| 5T4 | 5T4 oncofetal trophoblast glycoprotein |  | 2.54 |
| COVA1 | cytosolic ovarian carcinoma antigen 1 |  | 11.86 |
| BST2 | bone marrow stromal cell antigen 2 | 41.28 |  |
| FLT3LG | fms-related tyrosine kinase 3 ligand | 3.51 |  |
| RPL32 | ribosomal protein L32 |  | 13.06 |
| ECM1 | extracellular matrix protein 1 | 6.17 |  |
| BRCA1 | breast cancer 1, early onset |  | 6.55 |
| D10S170 | DNA segment, single copy, probe pH 4 (transforming sequence, thyroid-1) | 0.28 |  |
| COL1A2 | collagen, type 1, alpha 2 |  | 2.48 |
| COL13A1 | collagen, type XIII, alpha I |  | 2.20 |
| MM2 | paraneoplastic neuronal antigen |  | 46.63 |
| TIAF1 | TGFB1-induced anti-apoptotic factor 1 | 2.06 |  |
| IL18 | interleukin 18 (interferon-gamma-inducing factor) |  | 11.64 |
| STX11 | syntaxin 11 | 11.28 |  |
| KCNC4 | potassium voltage-gated channel, Shaw-related subfamily, member 4 | 4.12 |  |
| CLN2 | ceroid-lipofuscinosis, neuronal 2, late infantile (Jansky-Bielschowsky disease) | 2.36 |  |
| CST3 | cystatin C (amyloid angiopathy and cerebral hemorrhage) | 2.05 |  |
| APBB2 | amyloid beta (A4) precursor protein-binding, family B, member 2 (Fe65-like) |  | 13.13 |
| APBA3 | amyloid beta (A4) precursor protein-binding, family A, member 3 (X11-like 2) | 2.11 |  |
| KCNQ3 | potassium voltage-gated channel, KQT-like subfamily, member 3 |  | 13.97 |
| KCNS3 | potassium voltage-gated channel, delayed-rectifier, subfamily S, member 3 | 45.58 |  |
| MMP1 | matrix metalloproteinase 1 (interstitial collagenase) | 42.73 |  |
| MMP3 | matrix metalloproteinase 3 (stromelysin 1, progelatinase) |  | 3.84 |
| CACNA1E | calcium channel, voltage-dependent, alpha 1E subunit | 160.77 |  |

TABLE 5-continued

Altered Gene Expression in Crohn's Disease Patients

| Unigene Symbol | Gene description | Over-expressed in CD (S/C) | Under-expressed in CD (C/S) |
|---|---|---|---|
| GLI3 | GLI-Kruppel family member GLI3 (Greig cephalopolysyndactyly syndrome) | 5.66 | |
| ITGA | integrin, alpha 7 | 5.60 | |
| ITGAV | integrin, alpha V (vitronectin receptor, alpha polypeptide, antigen CD51) | | 2.61 |
| MSH2 | mutS (E. coli) homolog 2 (colon cancer, nonpolyposis type 1) | | 2.12 |
| MYBL1 | v-myb avian myeloblastosis viral oncogene homolog-like 1 | | 9.49 |
| SCYA20 | small inducible cytokine subfamily A (Cys-Cys), member 20 | 6.10 | |
| NPAS1 | neuronal PAS domain protein 1 | 6.46 | |
| ASPA | aspartoacylase (aminoacylase 2, Canavan disease) | | 17.28 |
| API2 | apoptosis inhibitor 2 | | 80.07 |
| BNIP1 | BCL2/adenovirus E1B 19 kD-interacting protein 1 | 2.64 | |
| IGF2 | insulin-like growth factor 2 (somatomedin A) | | 2.86 |
| GSTT1 | glutathione S-transferase theta 1 | 123.36 | |
| MYO1C | myosin 1C | 2.75 | |
| MYO5A | myosin VA (heavy polypeptide 12, myoxin) | | 7.70 |
| IFNB1 | interferon, beta 1, fibroblast | | 2.01 |
| CLN2 | ceroid-lipofuscinosis, neuronal 2 late infantile (Jansky-Bielschowsky disease) | 2.13 | 0.47 |
| G6PC | glucose-6-phosphatase, catalytic (glycogen storage disease type 1, von Gierke disease) | | 12.86 |
| IL13RA1 | interleukin 13 receptor, alpha 1 | 2.40 | |
| IL15RA | interleukin 15 receptor, alpha | | 2.92 |
| IL18R1 | interleukin 18 receptor 1 | 9.51 | |
| TTC1 | tetratricopeptide repeat domain 1 | | 8.17 |
| IRS2 | insulin receptor substrate 2 | 2.42 | |
| | proprotein convertase subtilisin/kexin type 5 | 1389.26 | |
| ALCAM | activated leucoyte cell adhesion molecule | | 2.92 |
| MFGE8 | milk fat globule-EGF factor 8 protein | 3.34 | |
| BST1 | bone marrow stromal cell antigen 1 | 6.11 | |
| PSMB3 | proteasome (prosome, macropain) subunit, beta type 3 | | 3.74 |
| RASA1 | RAS p21 protein activator (GTPase activating protein) 1 | | 2.30 |
| RAN | RAN, member of RAS oncogene family | | 2.67 |
| HLA-DPB1 | major histocompatibility complex, class II, DP beta 1 | | 40.72 |
| BRCA1 | breast cancer 2, early onset | | 13.53 |
| COL15A1 | collagen, type XV, alpha 1 | | 64.56 |
| MDU1 | antigen identified by monoclonal antibodies 4F2, TRA1.10, TROP4 and T43 | | 2.63 |
| CST6 | cystatin E/M | 2.04 | |
| ADAM21 | a disintegrin and metalloproteinase domain 21 | | 10.37 |
| C1NH | complement component 1 inhibitor (angioedema, hereditary) | 3.57 | |
| CASP9 | caspase 9, apoptosis-related cysteine protease | 2.39 | |
| PRSC1 | protease, cysteine 1 (legumain) | 0.49 | 2.04 |
| CMAH | cytidine monophosphate-N-acetylneuraminic acid hydroxylase (CMP-N-acetylneuraminate) | 2.43 | |
| APBB1 | amyloid beta (A4) precursor protein-binding, family A, member 2 (X11-like) | 8.00 | |
| CASP2 | caspase 2, apoptosis-related cysteine protease | | 11.70 |
| MMP2 | matrix metalloproteinase 2 (gelatinase A, 72 kD gelatinase, 72 kD type IV collagenase) | | 2.00 |

TABLE 5-continued

Altered Gene Expression in Crohn's Disease Patients

| Unigene Symbol | Gene description | Over-expressed in CD (S/C) | Under-expressed in CD (C/S) |
|---|---|---|---|
| MIC2 | antigen identified by monoclonal antibodies 12E7, F21 and O13 | 2.27 | 0.44 |
| SCN2A2 | sodium channel, voltage-gated, type II, alpha 2 polypeptide | | 2.14 |
| F10 | coagulation factor X | 3.68 | |
| F3 | coagulation factor III (thromboplastin, tissue factor) | | 3.91 |
| CLCN2 | chloride channel 2 | | 2.22 |
| CLCN3 | chloride channel 3 | | 2.13 |
| GRO1 | GRO1 oncogene (melanoma growth stimulating activity, alpha) | | 3.03 |
| APOC1 | apolipoprotein C-1 | 26.94 | |
| ITGA4 | integrin, alpha 4 (antigen CD49D, alpha 4 subunit of VLA-4 receptor) | 3.00 | |
| MYB | v-myb avian myeloblastosis viral oncogene homolog | 2.33 | |
| SCYA5 | small inducible cytokine A5 (RANTES) | 2.05 | |
| NRCAM | neuronal cell adhesion molecule | 9.00 | |
| HTLF | T-cell leukemia virus enhancer factor | 2.47 | |
| ACCN2 | amiloride-sensitive cation channel 2, neuronal | 3.78 | |
| ARHE | ras homolog gene family, member E | | 2.02 |
| ARHGAP4 | Rho GTPase activating protein 4 | 2.06 | 0.48 |
| IGF2 | insulin-like growth factor 2 (somatomedin A) | 0.32 | 3.11 |
| MYLK | mysoin, light polypeptide kinase | 0.16 | 6.22 |
| IL11RA | interleukin 11 receptor, alpha | 2.03 | 0.49 |
| IL13RA2 | interleukin 13 receptor, alpha 2 | 3.04 | 0.33 |
| YWHAZ | tyrosine 3-monooxygenase/tryptophan 5-monooxygenase activation protein, zeta polypeptide//dilution 1:3125 | 0.16 | 6.11 |
| PSEN2 | presenilin 2 (Alzheimer diease 4) | 0.30 | 3.28 |
| TRAF4 | TNF receptor associated factor 4 | 0.41 | 2.45 |
| PKD2 | polycystic kidney disease 2 (autosomal dominant) | 0.35 | 2.87 |
| PSMA5 | proteasome (prosome, macropain) subunit, alpha type 5 | 0.37 | 2.70 |
| RAB33A | RAB33A, member RAS oncogene family | 3.87 | 0.26 |
| CEACAM4 | carcinoembryonic antigen-related cell adhesion molecule 4 | 0.14 | 7.33 |
| PSMC5 | proteasome (prosome, macropain) 26S subunit, ATPase, 5 | 0.08 | 12.03 |
| PSMD12 | proteasome (prosome, macropain) 26S subunit, non-ATPase, 12 | 0.44 | 2.30 |
| RGS4 | regulator of G-protein signalling 4 | 0.09 | 10.93 |
| RGS7 | regulator of G-protein signalling 7 | 0.05 | 18.59 |
| FUT4 | fucosyltransferase 4 (alpha (1,3) fucosyltransferase, myeloid-specific) | 3.07 | 0.33 |
| AKAP12 | A kinase (PRKA) anchor protein (gravin) 12 | 3.05 | 0.33 |
| hla-f | HLA-F gene for leukocyte antigen F | 0.50 | 2.01 |
| HLA-G | HLA-G histocompatibility antigen, class I, G | 4.04 | 0.25 |
| COL7A1 | collagen, type VII, alpha I (epidermolysis bullosa, dystrophic, dominant and recessive) | 0.03 | 31.01 |
| ACCN2 | amiloride-sensitive cation channel 2, neuronal | 14.53 | 0.07 |
| KCNJ4 | potassium inwardly-rectifying channel, subfamily J, member 4 | 0.35 | 2.84 |
| ELA2 | elastase 2, neutrophil | 11.72 | 0.09 |
| IL1RL1 | interleukin 1 receptor-like 1 | 17.69 | 0.06 |
| SCYA2 | small inducible cytokine A2 (monocyte chemotactic protein 1, homologous to mouse Sig-je) | 0.22 | 4.56 |
| F8C | coagulation factor VIIIc procoagulant component (hemophilia A) | 2.35 | 0.43 |
| MAAT1 | melanoma antigen antigen recognized by T lymphocytes | 0.37 | 2.70 |

TABLE 5-continued

Altered Gene Expression in Crohn's Disease Patients

| Unigene Symbol | Gene description | Over-expressed in CD (S/C) | Under-expressed in CD (C/S) |
|---|---|---|---|
| ICAP-1A | integrin cytoplasmic domain-associated protein 1 | 7.12 | 0.14 |
| LTB | lymphotoxin beta (TNF superfamily, member 3) | 24.48 | 0.04 |
| SCYB6 | small inducible cytokine subfamily B (Cys-X-Cys), member 6 (granulocyte chemotactic protein 2) | 0.20 | 5.12 |
| SCYA16 | small inducible cytokine subfamily A (Cys-Cys), member 16 | 2.01 | 0.50 |
| L1CAM | L1 cell adhesion molecule (hydrocephalus, stenosis of aqueduct of Sylvius 1), MASA | 7.50 | 0.13 |
| TIM | oncogene TIM | 6.36 | 0.16 |
| SFRP1 | secreted frizzled-related protein 1 | 9.09 | 0.11 |
| TNFSF-10 | tumor necrosis factor (ligand) superfamily, member 10 | 0.02 | 47.84 |
| ARHGDIB | Rho GDP dissociation inhibitor (GDI) | 18.93 | 0.05 |
| GNB3 | guanine nucleotide binding protein (G protein), beta polypeptide 3 | 2.36 | 0.42 |
| BCL2L2 | BCL2-like 2 | 0.37 | 2.71 |
| IL1R1 | interleukin 1 receptor, type 1 | 3.94 | 0.25 |
| IL1RAP | interleukin 1 receptor accessory protein | 0.11 | 8.80 |
| PRSS3 | protease, serine, 3 (trypsin 3) | 8.61 | 0.12 |
| PSMA4 | proteasome (prosome, macropain) subunit, alpha type 4 | 0.34 | 2.97 |
| RAB3A | RAB3A, member RAS oncogene family | 0.29 | 3.41 |
| MGP | matrix Gla protein | 3.03 | 0.33 |
| COL11A1 | collagen, type XI, alpha 1 | 8.04 | 0.12 |
| HLA-G | HLA-G histocompatibility antigen, class I, G | 9.76 | 0.10 |
| HLA-G | HLA-G histocompatibility antigen, class I, G | 3.62 | 0.28 |
| KIAA0830 | KIAA0830 protein | 0.34 | 2.98 |
| COL8A1 | collagen, type VIII, alpha 1 | 0.38 | 2.63 |
| PCSK4 | proprotein convertase subtilisin/kexin type 4 | 0.14 | 6.96 |
| PLOD2 | procollagen-lysine, 2 oxyglutarate 5-dioxygenase (lysine hydroxylase) 2 | 0.34 | 2.94 |
| KCNJ8 | potassium inwardly-rectifying channel, subfamily J, member 8 | 23.62 | 0.04 |
| KCNK1 | potassium channel, subfamily K, member 1 (TWIK-1) | 17.39 | 0.06 |
| HAT | airway trypsin-like protease | 0.48 | 2.10 |
| SCYA3 | small inducible cytokine A3 (homologous to mouse Mip-1a) | 8.17 | 0.12 |
| IL12A | interleukin 12A (natural killer cell stimulatory factor 1, cytotoxic lymphocyte maturation factor 1, p35) | 0.07 | 13.55 |
| CASP1 | caspase 1, apoptosis-related cysteine protease (interleukin 1, beta, convertase) | 0.45 | 2.23 |
| SCN1B | sodium channel, voltage-gated, type 1, beta polypeptide | 2.14 | 0.47 |
| SCN9A | sodium channel, voltage-gated, type IX, alpha polypeptide | 0.42 | 2.41 |
| MMP17 | matrix metalloproteinase 17 (membrane-inserted) | 0.32 | 3.09 |
| MMP23A | matrix metalloproteinase 23A | 2.86 | 0.35 |
| F7 | coagulation factor VII (serum prothrombin conversion prothrombin conversion) | 0.05 | 21.19 |
| SCYB5 | small inducible cytokine subfamily B (Cys-X-Cys), member 5 (epithelial-derived neutrophil-activating peptide 78) | 0.28 | 3.60 |
| EDIL3 | EGF-like repeats and discoidin I-like domains 3 | 60.14 | 0.02 |
| M1S1 | membrane component, chromosome 1, surface marker 1 (40 kD glycoprotein, identified by monoclonal antibody GA733) | 2.58 | 0.39 |
| NBL1 | neuroblastoma candidate region, suppression of tumorigenicity 1 | 2.39 | 0.42 |

TABLE 5-continued

Altered Gene Expression in Crohn's Disease Patients

| Unigene Symbol | Gene description | Over-expressed in CD (S/C) | Under-expressed in CD (C/S) |
|---|---|---|---|
| TNFAIP6 | tumor necrosis factor, alpha-induced protein 6 | 0.05 | 20.62 |
| CACNA1A | calcium channel, voltage-dependent P/Q type, alpha 1A subunit | 7.33 | 0.14 |
| CACNA1H | calcium channel, voltage-dependent, alpha 1H subunit | 10.03 | 0.10 |
| CACNA2D1 | calcium channel, voltage-dependent, alpha 2/delta subunit 1 | 0.35 | 2.87 |
| WNT5A | wingless-type MMTV integration site family, member 5A | 0.39 | 2.58 |
| NAIP | neuronal apoptosis inhibitory protein | 0.15 | 6.82 |
| ARHGAP5 | Rho GTPase activating protein 5 | 7.06 | 0.14 |
| ARHI | ras homolog gene family, member 1 | 2.61 | 0.38 |
| RASA2 | RAS p21 protein activator 2 | 11.88 | 0.08 |
| GNG11 | guanine nucleotide binding protein 11 | 0.43 | 2.34 |
| IFIT1 | interferon-inducing protein 56 | 0.03 | 31.13 |
| VMD2 | vitelliform macular dystrophy (Best disease, bestrophin) | 3.66 | 0.27 |
| PSEN2 | presenlin 2 (Alzheimer disease 4) | 0.24 | 4.15 |
| D13S1056E | Probe hTg737 (polycystic kidney disease, autosomal recessive) | 2.74 | 0.37 |

TABLE 6

Altered Gene Expression in Ulcerative Colitis Disease Patients

| Unigene Symbol | Gene description | Over-expressed in UC (S/C) | Under-expressed in UC (C/S) |
|---|---|---|---|
| PDCD2 | programmed cell death 2 | 3.19 | 0.31 |
| GTPBP1 | GTP binding protein 1 | 5.66 | 0.18 |
| KNSL2 | kinesin-like 2 | 0.15 | 6.53 |
| RAB2 | RAB2, member RAS oncogene family | 0.07 | 13.79 |
| COVA1 | cytosolic ovarian carcinoma antigen 1 | 2.41 | 0.41 |
| BST2 | bone marrow stromal cell antigen 2 | 247.90 | 0.00 |
| PSMB8 | proteasome (prosome, macropain) subunit, beta type, 8 (large multifunctional protease 7) | 3.12 | 0.32 |
| FLT3LG | fms-related tyrosine kinase 3 ligand | 12.50 | 0.08 |
| ZMPSTE24 | zinc metalloproteinase, STE24 (yeast, homolog) | 0.49 | 2.05 |
| TIMP1 | tissue inhibitor of metalloproteinase 1 (erythroid potentiating activity, colleganase inhibitor) | 1.01 | 0.99 |
| TIMP3 | tissue inhibitor of metalloproteinase 3 (Sorsby fundus dystrophy, pseudoinflammatory) | 4.37 | 0.23 |
| HLA-C | major histocompatibility complex, class I, C | 2.31 | 0.43 |
| D10S170 | DNA segment, single copy, probe pH 4 (transforming sequence, thyroid-1) | 0.43 | 2.31 |
| MM2 | paraneoplastic neuronal antigen | 0.09 | 10.72 |
| LY6E | lymphocyte antigen 6 complex, locus E | 4.48 | 0.22 |
| SCA2 | spinocerebellar ataxia 2 (olivopontocerebellar ataxia 2, autosomal dominant, ataxin 2) | 0.47 | 2.13 |
| IL18 | interleukin 18 (interferon-gamma-inducing factor) | 0.17 | 5.89 |
| STX3A | syntaxin 3A | 0.28 | 3.57 |
| STX11 | syntaxin 11 | 13.29 | 0.08 |
| KCNC4 | potassium voltage-gated channel, Shaw-related subfamily, member 4 | 3.15 | 0.32 |
| CLN2 | ceroid-lipofuscinosis, neuronal 2, late infantile (Jansky-Bielschowsky disease) | 2.38 | 0.42 |
| KCNQ3 | potassium voltage-gated channel, KQT-like subfamily, member 3 | 0.28 | 3.62 |
| KCNS3 | potassium voltage-gated channel, delayed-rectifier, subfamily S, member 3 | 52.41 | 0.02 |
| MMP1 | matrix metalloproteinase 1 (interstitial collagenase) | 122.60 | 0.01 |
| CACNA1E | calcium channel, voltage-dependent, alpha 1E subunit | 121.38 | 0.01 |

TABLE 6-continued

Altered Gene Expression in Ulcerative Colitis Disease Patients

| Unigene Symbol | Gene description | Over-expressed in UC (S/C) | Under-expressed in UC (C/S) |
|---|---|---|---|
| FOSL2 | FOS-like antigen 2 | 7.83 | 0.13 |
| GRO2 | GRO2 oncogene | 4.90 | 0.20 |
| ITGA7 | integrin, alpha 7 | 0.12 | 8.30 |
| ITGAV | integrin, alpha V (vitronectin receptor, alpha polypeptide, antigen CD51) | 0.03 | 30.23 |
| MYBL1 | v-myb avian myeloblastosis viral oncogene homolog-like 1 | 0.26 | 3.78 |
| SCYA20 | small inducible cytokine subfamily A (Cys-Cys), member 20 | 41.55 | 0.02 |
| LMO4 | LIM domain only 4 | 2.38 | 0.42 |
| NPAS1 | neuronal PAS domain protein 1 | 3.35 | 0.30 |
| APG5L | APG5 (autophagy 5, S. cerevisiae)-like | 0.41 | 2.44 |
| BNIP1 | BCL2/adenovirus E1B 19 kD-interacting protein 1 | 2.33 | 0.43 |
| IGF2 | insulin-like growth factor 2 (somatomedin A) | 0.34 | 2.96 |
| IL1A | interleukin 1, alpha | 5.57 | 0.18 |
| GSTT1 | glutathione S-transferase theta 1 | 58.37 | 0.02 |
| IL18R1 | interleukin 18 receptor 1 | 4.93 | 0.20 |
| YWHAZ | tyrosine 3-monooxygenase/tryptophan 5-monooxygenase activation protein, zeta polypeptide // Dilution 1:3125 | 0.14 | 7.29 |
| TTC1 | tetratricopeptide repeat domain 1 | 0.08 | 12.26 |
| IRS2 | insulin receptor substrate 2 | 3.25 | 0.31 |
| PCSK5 | proprotein convertase subtilisin/kexin type 5 | 519.20 | 0.00 |
| PCSK7 | proprotein convertase subtilisin/kexin type 7 | 0.38 | 2.65 |
| PSMB9 | proteasome (prosome, macropain) subunit, beta type, 9 (large multifunctional protease 2) | 6.45 | 0.16 |
| RASA1 | RAS p21 protein activator (GTPase activating protein) 1 | 0.46 | 2.19 |
| RAN | RAN, member RAS oncogene family | 0.50 | 2.01 |
| FALZ | fetal Alzheimer antigen | 0.38 | 2.62 |
| TIMP2 | tissue inhibitor of metalloproteinase 2 | 0.29 | 3.50 |
| TPP2 | tripeptidyl peptidase II | 0.39 | 2.56 |
| HLA-B | major histocompatibility complex, class I, B | 0.08 | 12.61 |
| HLA-DPB1 | major histocompatibility complex, class II, DP beta 1 | 0.18 | 5.46 |
| CST6 | cystatin E/M | 0.22 | 4.51 |
| DDX17 | DEAD/H (Asp-Glu-Ala-Asp/His) box polypeptide 17 (72 kD) | 0.42 | 2.37 |
| ADAM21 | a disintegrin and metalloproteinase domain 21 | 0.11 | 9.02 |
| WNT2B | wingless-type MMTV integration site family, member 2B | 0.31 | 3.18 |
| SOD3 | superoxide dismutase 3, extracellular | 0.00 | 286.37 |
| CMAH | cytidine monophosphate-N-acetylneuraminic acid hydroxylase (CMP-N-acetylneuraminate | 3.52 | 0.28 |
| APBA2 | amyloid beta (A4) precursor protein-binding, family A, member 2 (X11-like) | 5.45 | 0.18 |
| MME | membrane metallo-endopeptidase (neutral endopeptidase, enkephalinase, CALLA, CD10) | 3.39 | 0.29 |
| NOVA1 | neuro-oncological ventral antigen 1 | 3.88 | 0.26 |
| GRO3 | GRO3 oncogene | 2.24 | 0.45 |
| APOC1 | apolipoprotein C-I | 31.29 | 0.03 |
| ITGA6 | integrin, alpha 6 | 0.12 | 8.31 |
| MET | met proto-oncogene (hepatocyte growth factor receptor) | 0.19 | 5.13 |
| MYB | v-myb avian myeloblastosis viral oncogene homolog | 3.22 | 0.31 |
| SCYA5 | small inducible cytokine A5 (RANTES) | 64.90 | 0.02 |
| NRCAM | neuronal cell adhesion molecule | 2.70 | 0.37 |
| IGF2 | insulin-like growth factor 2 (somatomedin A) | 0.29 | 3.40 |
| IL6 | interleukin 6 (interferon, beta 2) | 2.81 | 0.36 |
| IL1B | interleukin 1, beta | 5.35 | 0.19 |
| IL3 | interleukin 3 (colony-stimulating factor, multiple) | 4.27 | 0.23 |
| MYLK | myosin, light polypeptide kinase | 0.44 | 2.28 |
| MYO6 | myosin VI | 0.45 | 2.22 |
| IFIT2 | interferon-induced protein 54 | 4.84 | 0.21 |
| FIC1 | familial intrahepatic cholestasis 1, (progressive, Byler disease and benign recurrent) | 0.33 | 3.00 |
| IL13RA2 | interleukin 13 receptor, alpha 2 | 4.19 | 0.24 |
| PSEN2 | presenilin 2 (Alzheimer disease 4) | 0.49 | 2.03 |

TABLE 6-continued

Altered Gene Expression in Ulcerative Colitis Disease Patients

| Unigene Symbol | Gene description | Over-expressed in UC (S/C) | Under-expressed in UC (C/S) |
|---|---|---|---|
| PKD2 | polycystic kidney disease 2 (autosomal dominant) | 0.49 | 2.06 |
| PKD2 | polycystic kidney disease 2 (autosomal dominant) | 0.11 | 9.19 |
| RAB4 | RAB4, member RAS oncogene family | 0.34 | 2.94 |
| RAB5B | RAB5B, member RAS oncogene family | 0.18 | 5.43 |
| PSMC5 | proteasome (prosome, macropain) 26S subunit, ATPase, 5 | 0.21 | 4.75 |
| PSMD12 | proteasome (prosome, macropain) 26S subunit, non-ATPase, 12 | 0.45 | 2.22 |
| RGS2 | regulator of G-protein signalling 2, 24 kD | 3.07 | 0.33 |
| RGS4 | regulator of G-protein signalling 4 | 0.11 | 9.51 |
| RGS7 | regulator of G-protein signalling 7 | 0.06 | 16.16 |
| FUT4 | fucosyltransferase 4 (alpha (1,3) fucosyltransferase, myeloid-specific) | 2.04 | 0.49 |
| AKAP12 | A kinase (PRKA) anchor protein (gravin) 12 | 2.06 | 0.48 |
| ENC1 | ectodermal-neural cortex (with BTB-like domain) | 0.47 | 2.14 |
| hla-f | HLA-F gene for leukocyte antigen F | 6.77 | 0.15 |
| HLA-G | HLA-G histocompatibility antigen, class I, G | 3.00 | 0.33 |
| X | MHC class I HLA-J gene, exons 1-8 and complete cds | 4.64 | 0.22 |
| SPG7 | spastic paraplegia 7, paraplegin (pure and complicated autosomal recessive) | 0.47 | 2.12 |
| ACCN2 | amiloride-sensitive cation channel 2, neuronal | 8.60 | 0.12 |
| KCNJ4 | potassium inwardly-rectifying channel, subfamily J, member 4 | 0.35 | 2.83 |
| IL1RL1 | interleukin 1 receptor-like 1 | 301.56 | 0.00 |
| IL16 | interleukin 16 (lymphocyte chemoattractant factor) | 0.25 | 4.05 |
| STUB1 | STIP1 homology and U-Box containing protein 1 | 0.48 | 2.09 |
| LTB | lymphotoxin beta (TNF superfamily, member 3) | 4.79 | 0.21 |
| SCYB6 | small inducible cytokine subfamily B (Cys-X-Cys), member 6 (granulocyte chemotactic protein 2) | 5.45 | 0.18 |
| SCYA16 | small inducible cytokine subfamily A (Cys-Cys), member 16 | 3.46 | 0.29 |
| NF1 | neurofibromin 1 (neurofibromatosis, vonRecklinghausen disease, Watson disease) | 5.25 | 0.19 |
| SPG7 | spastic paraplegia 7, paraplegin (pure and complicated autosomal recessive | 0.47 | 2.11 |
| ARHGDIB | Rho GDP dissociation inhibitor (GDI) | 4.94 | 0.20 |
| BCL2L2 | BCL2-like 2 | 0.42 | 2.36 |
| IFNW1 | interferon, omega 1 | 4.15 | 0.24 |
| IRS2 | insulin receptor substrate 2 | 2.65 | 0.38 |
| IFNAR2 | interferon (alpha, beta and omega) receptor 2 | 2.38 | 0.42 |
| RAC3 | ras-related C3 botulinum toxin substrate 3 (rho family, small GTP binding protein Rac3) | 6.92 | 0.14 |
| CLU | clusterin (complement lysis inhibitor, SP-40,40, sulfated glycoprotein 2, . . . , apolipoprotein J) | 0.33 | 2.99 |
| TNFRSF1B | tumor necrosis factor receptor superfamily, member 1B | 0.25 | 4.03 |
| PRSS11 | protease, serine, 11 (IGF binding) | 0.44 | 2.29 |
| PRSS3 | protease, serine, 3 (trypsin 3) | 7.08 | 0.14 |
| RAB5A | RAB5A, member RAS oncogene family | 0.01 | 68.39 |
| PSMD13 | proteasome (prosome, macropain) 26S subunit, non-ATPase, 13 | 0.46 | 2.18 |
| MGP | matrix Gla protein | 0.24 | 4.17 |
| COL11A1 | collagen, type XI, alpha 1 | 21.90 | 0.05 |
| HLA-G | HLA-G histocompatibility antigen, class I, G | 3.07 | 0.33 |
| KIAA0830 | KIAA0830 protein | 0.30 | 3.33 |
| EMS1 | ems1 sequence (mammary tumor and squamous cell carcinoma-associated (p80/85 src substrate) | 0.44 | 2.29 |

TABLE 6-continued

Altered Gene Expression in Ulcerative Colitis Disease Patients

| Unigene Symbol | Gene description | Over-expressed in UC (S/C) | Under-expressed in UC (C/S) |
|---|---|---|---|
| PCSK4 | proprotein convertase subtilisin/kexin type 4 | 0.17 | 6.05 |
| CASP3 | caspase 3, apoptosis-related cysteine protease | 0.48 | 2.09 |
| PLOD2 | procollagen-lysine, 2-oxoglutarate 5-dioxygenase (lysine hydroxylase) 2 | 0.28 | 3.57 |
| KCNK1 | potassium channel, subfamily K, member 1 (TWIK-1) | 9.00 | 0.11 |
| SCYA3 | small inducible cytokine A3 (homologous to mouse Mip-1a) | 14.18 | 0.07 |
| IL12A | interleukin 12A (natural killer cell stimulatory factor 1, cytotoxic lymphocyte maturation factor 1, p35) | 0.36 | 2.75 |
| MMP17 | matrix metalloproteinase 17 (membrane-inserted) | 0.47 | 2.15 |
| X | Smooth muscle myosin heavy chain isoform Smemb | 2.20 | 0.45 |
| ITGA1 | integrin, alpha 1 | 2.34 | 0.43 |
| CLU | clusterin (complement lysis inhibitor, SP-40,40, sulfated glycoprotein 2, testosterone-repressed prostate message 2, apolipoprotein J) | 0.19 | 5.26 |
| TNFAIP6 | tumor necrosis factor, alpha-induced protein 6 | 6.68 | 0.15 |
| CACNA1H | calcium channel, voltage-dependent, alpha 1H subunit | 9.50 | 0.11 |
| WNT5A | wingless-type MMTV integration site family, member 5A | 0.47 | 2.12 |
| ARHI | ras homolog gene family, member I | 74.84 | 0.01 |
| CNK1 | connector enhancer of KSR-like (*Drosophila* kinase suppressor of ras) | 1.00 | 1.00 |
| RASA2 | RAS p21 protein activator 2 | 9.85 | 0.10 |
| IFIT1 | interferon-induced protein 56 | 35.91 | 0.03 |
| ATP6C | ATPase, H+ transporting, lysosomal (vacuolar proton pump)16 kD | 0.44 | 2.27 |
| RHO | rhodopsin (retinitis pigmentosa 4, autosomal dominant) | 0.27 | 3.68 |
| VMD2 | vitelliform macular dystrophy (Best disease, bestrophin) | 2.49 | 0.40 |
| PSEN2 | presenilin 2 (Alzheimer disease 4) | 0.28 | 3.61 |
| D13S1056E | Probe hTg737 (polycystic kidney disease, autosomal recessive, in) | 0.32 | 3.09 |

5.6. Telomerase Assay.

Cells ($3\times10^3$) were lysed in Telomerase Repeat Amplification Protocol (TRAP) buffer and telomerase activity was assayed using a Telomerase PCR ELISA kit (for example, Roche Diagnostics GmbH, Mannheim, Del.) following the manufacturers instructions. Briefly, in the first step, telomerase adds telomeric repeats to a biotinylated primer, which then is amplified by PCR. In the second step, the PCR product of telemerase activity is detected by ELISA using strepavidin coated plates, a digoxigenin (DIG)-labeled probe and an anti-DIG antibody conjugated to peroxidase. The reaction then is developed with the peroxidase substrate, TMB. A heat inactivated negative sample control is run for each test sample. The test sample is considered positive for Telomerase activity when the sample $OD_{490}$ is a minimum of 0.200 above that for the heat inactivated sample control ($\Delta OD>0.200$). HT-29 cells and the kit positive lysate were run as positive controls. Freshly isolated IEC from normal colon were run as a negative control.

The HITEC lines had increased telomerase activity as well as in contrast to the HIPEC lines. As shown in Table 4, HITEC-WT (tumor line) lysate contained significantly more telomerase activity as compared to its normal counterpart, HIPEC-WT. Additionally, active telomerase was detected in HITECs but not in HIPECs.

TABLE 4

Telomerase Activity in Paired Normal and Tumor Colonic Cell Lines

| Sample | Description | Telomerase Activity ($\Delta$ OD) |
|---|---|---|
| HIPEC-WT | Normal colon-derived cell line | 0.009 |
| HITEC-WT | Tumor colon-derived cell line | 0.479 |
| Normal Colonic IEC | Freshly isolated intestinal epithelial cells | 0.000 |
| HT-29 | Colon adenocarcinoma cell line | 2.120 |
| Positive | Control lysate | 2.416 |

Example 6

Identification of Potential Colon Cancer Biomarkers

Figure 8:
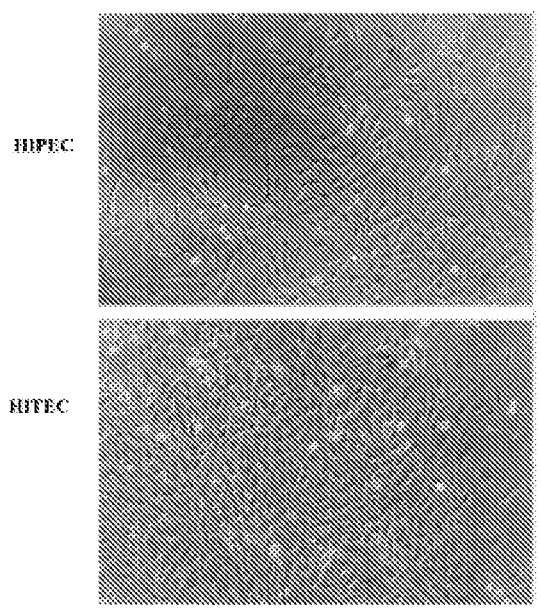
FIG. 8 shows representative photomicrographs of a paired human intestinal primary epithelial cell (HIPEC) (upper panel) and actual tumor derived epithelial cell (HITEC) (lower panel) lines derived from a patient with colonic adenoma.

Potential biomarkers will be identified using paired HIPEC and HITEC cell lines to examine differential expression of mRNAs, proteins, and lipids in CRC IECs compared to unaffected normal IECs from the same individuals. FIG. 8 shows one embodiment wherein isolated stem cells differentiate to an epithelial lineage from both diseased (colon cancer) and normal intestinal tissues.

6.1(a) mRNA Expression.

Gene array data yielding the over expression or under expression of transcripts (by at least 6 fold or greater) will be corroborated with mRNA expression by both RT-PCR and Northern analysis, as described in Example 5 above. If any specific alteration of gene expression by CRC HIPEC lines is detected, the conditions will be determined whereby normal HIPEC lines may be altered to the genotype (profile of gene expression) comparable to (1) CRC HIPECs and (2) the phenotype of CRC HIPEC lines may be reverted to a genotype comparable to normal HIPECs. Normal HIPEC lines will be subjected to the cytokine milieu produced in affected CRC tissue by co-culturing normal HIPECs with biopsy or tissue explants from patients with active CRC. Normal HIPEC will be co-cultured with normal tissues as controls.

6.1(b) Analysis Using Microarrays

An Affymetrix GeneChip Human Genome U133 Plus 2.0 Array (47,000 characterized transcripts) will be utilized for RNA expression analysis. Depending on the transcripts identified, Affymetrix Exon 1.0 ST Arrays or Gene 1.0 ST Arrays, which allow both a more detailed examination of expression levels and an examination of alternative splicing of the genes, will be included on the array. RNA will be isolated by, for example, the Affymetrix protocol. The slides will be scanned using a Microarray Scanner. The fluorescence intensities will be calculated using the GenePix 3.05 software. Microarray results will be derived by comparing total RNA from experimental (affected) HITECs (Cy5-labeled) vs. control (unaffected) HIPECs (Cy3-labeled). These results will be analyzed using GeneSpring software (Silicon Genetics). Artifact correction will be applied using an intensity-dependent normalization (Lowess normalization). The average expression level of each gene in the two groups will be calculated and the cutoff value set to 1.7 or 0.5 for the ratio of the median. Generally, cutoff values are assigned as above 2 and below 0.5, for up regulation of gene expression and/or down regulation of gene expression, respectively.

6.1(c) mRNA Expression Analysis Using RT-PCR

The expression of gene products identified via microarray analysis as potential biomarkers will be verified via RT-PCR in order to demonstrate expression in the cell line examined and to compare relative level of expression against other cell lines.

The cDNA sequence of genes identified via gene microarrays will be sourced from GenBank and PCR primers will be synthesized (Integrated DNA Technologies) for their detection. Depending on the type of gene identified, either total RNA or poly-A mRNA will be isolated from the cells, primed with N-capped random oligonucleotide or oligo-dT primers respectively, reverse transcribed with Superscript II, and amplified with the use of a Techne Progene thermal cycler and PlatPfx (Invitrogen). Reaction products will be run in TBE agarose gels, and RT-PCR products visualized with Ethidum Bromide staining DNA sequencing will be performed upon RT-PCR products to further verify their identity.

6.1(d) Analysis Using Northern Blots

Because splicing changes may cause, or may be a consequence of, transformation in CRC epithelial cells could also potentially be one of splicing changes, therefore, Northern analysis will be performed on identified potential biomarkers to determine whether any gross splicing alterations are observable.

Total RNA from the cells being examined will be isolated using an Applied Biosystems' ToTALLY RNA kit according to the manufacturer's instructions. Briefly, samples are lysed in a guanidinium based lysis solution and are then extracted sequentially with Phenol:Chloroform: IAA and Acid-Phenol: Chloroform. The RNA is then precipitated with isopropanol, and reagents are provided for an optional lithium chloride (LiCl) precipitation as well. The kit includes all the reagents (except isopropanol) required for isolation of total RNA from up to 10 g of tissue or about 109 cultured cells, and also includes ancillary reagents for analysis and storage of the RNA. The RT-PCR primers and products generated during the RT-PCR analysis will used to generate the detection probes. Northern analysis will be accomplished utilizing Applied Biosystems' NorthernMax kit and subsequent blotting to BrightStar-Plus nylon membranes.

6.2(a) Protein Analysis.

Without being limited by theory, it is believed that the cancerous state of the IECs in CRC results in the differential expression, when compared with unaffected IECs, of certain disease-specific proteins. The paired cell system of the present invention allows purification of such proteins from pure cell populations. There are many means for the analytical analysis of proteins being expressed in CRC cells that are complementary, but no one method is optimal for detecting all expressed proteins. Therefore, extracted proteins from paired cell lines will be analyzed and compared utilizing: 2D-DIGE, iTRAQ, cICAT, and coupled liquid chromatography-mass spectrometry (LC-MS/MS) and gas-chromatography-mass spectrometry (GC-MS/MS) utilizing different separation medias, procedures, and extraction methods.

Proteins isolated from HIPEC and HITEC cells will be analyzed via tandem GC/MS, LC/MS, and 2D-DIGE coupled with MALDI-TOF MS.

6.2(b) Protein Extraction and Purification.

Proteins will be extracted and purified from both media and cells as follows. Media will be removed from two 100 mm plates, (or a number of plates that will yield approximately 1 mg of total protein) per cell line and the plates washed twice with cold PBS. Cold PBS (3 ml) will be added to each plate and the cells will be scraped off and collected (first material). An additional 3 ml of cold PBS will then be added per plate. The plates will be scraped again, and the cells collected, combined with the first material in a 15 ml centrifuge tube. Cells will be pelleted by centrifugation at 500 g for 5 minutes, and the supernatant aspirated off. Cell pellets will be washed twice more with cold PBS. Cell pellets will be dissolved in Lysis Buffer (7M Urea, 2M Thiourea, 4% CHAPS, 0.2% BioLytes 3/10, 0.5% Triton X-100, 2.5 mM Na-pyrophosphate, 1.0 mM $Na_3VO_4$, 15 μl SIGMA's Protease Inhibitor Cocktail), incubated for 10 minutes on ice, sonicated three times for 5 seconds, centrifuged at 14,000×g for 30 minutes, and the supernatant collected. Amersham's 2-D Clean-Up kit will be used to remove salts. Protein pellets will be dissolved in Lysis Buffer, sonicated for 5 seconds, and the protein concentration quantified by the Bradford method using a Bio-Rad Protein Assay kit. The pH of sample will be adjusted to 8.5 and the concentration adjusted to 5-10 mg/ml.

This assay also will be repeated utilizing differential extractions with different detergent combinations in order to enrich for membrane bound proteins. Furthermore, the media from the cells also will be collected and analyzed for protein to identify secretory proteins useful as potential biomarkers.

6.2(c) Fluorescence 2-D Difference Gel Electrophoresis (2D-DIGE) Using Cy2, Cy3, and Cy5.

Stock CyDye DIGE fluors from Amersham will be resuspended in DMF to a concentration of 1 nmol/μl. These stocks of Cy2, Cy3, and Cy5 will be diluted further with DMF to 400 pmol/μl and the protein samples will be diluted to 5-10 pmol/μl. 400 pmol of fluor will be used to label 50 μg of protein. The fluor and protein sample will be mixed by vortexing, spin briefly, and incubated on ice for 30 minutes in the dark. 1 μl of 10 mM Lysine will be added to stop the reaction. The sample will be mixed, spun briefly, and incubated on ice for 10 minutes in the dark.

6.2(d) Protein Separation: 2-Dimensional Gel Electrophoresis.

Three of the labeled protein samples (Cy2, Cy3, and Cy5) will be mixed and separated, first utilizing isoelectric focusing (IEF), and second by molecular weight via SDS-PAGE. A BioRad Citerion 2D-Gel In CAPR, utilizing a BioRad PROTEAN IEF Cell and a BioRad Criterion Dodeca cell will enable simultaneous running of up to twelve 2-D gels at a time. Approximately 300-500 µg of protein will be loaded per gel when staining with Coomassie Blue and 100-200 µg for Sypro Ruby staining.

6.2(e) Spot Picking

Gels will be stained with Coomassie Blue or Sypro Ruby, scanned using a Molecular Dynamics' Densitometer SI or Amersham Biosciences' Typhoon 9410 Fluorescent Imager, and analyzed by Image Quant or DeCyder software packages. A pick list of desired spots will be generated, the spots will be picked by an Amersham Pharmacia Biotech's Ettan Spot Picker, and the gel plugs deposited into 96-well microtiter plates.

6.2(f) Protein Digestion.

Protein(s) within the gel plugs in the microtiter plates will be digested with trypsin using a robotic protein digestor, e.g., TECAN's Genesis Pro Team 150.

6.2(g) Mass Spectrometry.

MALDI-TOF/TOF mass spectrometry analysis will be performed upon the digested samples utilizing Applied Biosystems' 4700 Proteomics Analyzer, Micromass' Q-TOF API-US, and PerSeptive Biosystems' Voyager-DE PRO. Proteins that cannot be identified unambiguously using a MALDI-TOF MS and MS-FiT will undergo de novo sequence analysis by tandem mass spectrometry, on-line LC coupled QTOF MS/MS, and MALDI-TOF-TOF tandem MS. The tandem MS experiments will be performed with a Micromass cLC capillary HPLC coupled to a QTOF MS/MS system and a LC Packings capillary HPLC coupled to an MALDI-TOF-TOF tandem mass spectrometer 6.2(h) Amino Acid Sequencing.

Samples for protein sequencing will be applied to a PVDF membrane and sequenced using Edman degradation on an Applied Biosystems' Procise 494 cLC.

6.2(i) iTRAQ.

This proteomics method allows the multiplexed comparison of up to 4 samples in a single experiment. The labeling reagent consists of a quantification group, N-methylpiperazine, a balance group, carbonyl, and a hydroxyl succinimide ester group that reacts with primary amines in the peptide fragments derived from the digestion of the purified proteins. Quantification is accomplished by measuring the relative abundance of the four reporter ions (m/z 114.1, 115.1, 116.1, and 117.1) produced following MS/MS fragmentation of the isobaric iTRAQ labeled peptide mixture. Purified proteins will be dissolved in 100 mM triethylammonium bicarbonate buffer, pH 8.5, cysteine residues will be blocked and alkylated with MMTS as described in Applied Biosystems' iTRAQ™ protocol, and the proteins then digested overnight with trypsin. The resulting peptide fragments then will be labeled with the iTRAQ reagent in 70% ethanol following the Applied Biosystems' iTRAQ™ protocol. Samples then will be fractionated using cation exchange and subjected to LC/MS/MS analysis for protein identification and quantification. MS results will be analyzed using iTracker and Quant.

6.2(j) cICAT

This proteomics method will be utilized to compare paired HIPEC and HITEC cell lines to one another. Like the iTRAQ method, the cICAT method involves post-harvest labeling of the purified protein. The cICAT system consists of three components: a reactive group that reacts with free thiol moieties of cysteine residues, a linker containing a stable isotope, and a biotin tag for affinity purification and detection of peptides labeled with either a heavy or light version of the ICAT reagent. Purified proteins will be reduced using TCEP and boiled for 10 minutes. The two protein samples, one HIPEC and the corresponding paired HITEC, then will be transferred into a vial containing either the cICAT heavy reagent or light reagent (Applied Biosystems), mixed, briefly centrifuged, incubated for 2 hours at 37° C. in the dark, combined, and dried using a SpeedVac. Samples then will be fractionated using either SDS-PAGE or cation exchange LC, and digested with trypsin. ICAT labeled peptides will be purified with avidin cartridges (Applied Biosystems) and the eluate from the avidin cartridge dried in a SpeedVac. Peptide sequences will be determined using reversed-phase liquid chromatography-tandem mass spectrometry, LC-MS/MS. The ProID and ProICAT software packages from Applied Biosystems will be used for the identification and quantitation of proteins based upon the LC-MS/MS analysis of the purified peptides.

Protein expression also will be analyzed by immunofluorescence staining and subsequent flow cytometry analysis, immunohistochemical staining, and Western blot analysis subject to the availability of antibodies against identified target molecules.

6.3(a) Lipid Analysis.

Lipids will be analyzed via tandem GC/MS, LC/MS, and post-separation TLC dye staining and antibody overlays, immunofluorescence staining and subsequent flow cytometry analysis, and immunohistochemical staining subject to the availability of antibodies against identified target molecules.

Example 7

Analysis of Other Reputed Colon Cancer Biomarkers

Putative previously identified colon cancer biomarkers will be analyzed utilizing the same paired HIPEC lines and panels used in validating the biomarkers (see Examples 5 and 6) identified by the described methods.

Example 8

Validation of Identified Biomarkers

Validation of putative biomarkers will be accomplished using several methodologies to provide a direct comparison between paired samples or cell lines derived from disease affected tissue regions and unaffected normal controls. Comparisons obtained with the paired system will allow an increase, a decrease, a stimulation, an activation or an inhibition of expression of the biomarker signal to be identified and measured/quantified between the disease state and unaffected state.

8.1. RT-PCR Analysis:

RT-PCR analysis entails four steps: (1) RNA purification, (2) the RT reaction, (3) the RT-PCR reaction, and (4) visualization/quantitation/scoring of RT-PCR products. An oligo (dT)20 primer is utilized to prime the RT reaction. By forgoing a gene specific primer (GSP), costs and efforts are reduced and the samples and RT-PCR reactions remain equilibrated with a minimum of effort.

8.2. Purification of Total RNA:

Total RNA will be purified either from tissue samples/biopsies or from adherent cells growing in tissue culture flasks. Tissue samples will be placed in RNA Later (Invitrogen) and are stored at −20° C. till processed (total RNA purified). Approximately 1 ml of TRIZOL LS reagent (Invitrogen) will be added per 50-100 mg of tissue sample and the sample homogenized using a glass-Teflon probe. Cells grown in culture will be lysed directly in the culture dish by the addition of 1 ml of TRIZOL per 10 cm$^2$ of dish surface area with repetitive pipetting. After homogenization, the samples are allowed to sit for 5 minutes at 15-30° C. (room temperature) in order to allow dissociation of nucleoprotein complexes. An appropriate amount of chloroform (0.2 ml) is added per ml of TRIZOL utilized to homogenize the cells or tissue samples. Samples are shaken vigorously by hand for 15 seconds and then incubated at 15-30° C. for 3 minutes. Samples then are centrifuged 12,000×g for 15 minutes at 2-8° C. The upper aqueous phase is removed to a fresh tube and 0.5 ml of isopropanol per ml of TRIZOL utilized in the initial homogenization is added to the tube. The sample is vortexed for 1 minute and then incubated for 10 minutes at 15-30° C. prior to centrifugation of 12,000×g for 10 minutes at 2-8° C. The supernatant is removed and the pellet washed with 75% ethanol such that 1 ml of ethanol per ml of TriZOL is utilized. The pellet is allowed to air dry and then is resuspended in DEPC treated distilled filtered H$_2$O. The total RNA purified then is measured utilizing a spectrophotometer and absorbance at A260.

8.3(a) RT Reaction:

The RT and PCR reactions and incubations are performed in a Techne PROGENE thermal cycler with a heated lid (Techne, Burlington, N.J.).

Generally, RT reactions are performed in a 26 µl reaction volume with 2 µg of total RNA, 2 µl of 50 µM oligo(dT)20 to prime the RT reaction, and 4 µl of 10 mM dNTP. The reaction is incubated for 5 minutes at 65° C.; then quickly cooled to 4° C. A 14 µl mixture composed of 8 µl of 5× cDNA synthesis buffer (250 mM Tris acetate; pH 8.4, 375 mM potassium acetate, 40 mM magnesium acetate, and a stabilizer (Invitrogen)), 2 µl of 0.1M DTT, 2 µl of RNaseOUT (40 U/µl (Invitrogen)), and 2 µl of ThermoScript RT (15 U/µl (Invitrogen)) is added to the microcentrifuge tube containing the annealed 26 µl reaction. The combined 40 µl reaction is heated to 55° C. for 60 minutes. The temperature then is raised to 85° C. for 5 minutes, before returning it to 4° C. RNAse H (2 µl) (Invitrogen) is added to the mixture and the tubes heated to 37° C. for 20 minutes; followed by cooling to 4° C. 4 µl of this RT reaction will be used in the subsequent 50 µl PCR reactions described below.

8.3(b) PCR:

Master mixes comprised of all PCR reaction components (except the RT product) are utilized in order to maximize efficiency and to minimize amplification variability from sample-to-sample, as well as from experiment to experiment. A 50 µl PCR reaction is assembled using 4 µl from the prepared RT reaction described above, 5 µl of 10× Plat Taq PCR buffer Minus Mg (Invitrogen), 1.5 µl of 50 mM MgCl$_2$, 1 µl of 10 mM dNTP, 3 µl of a 10 µM stock of sense/forward target gene specific oligonucleotide primer, 3 µl of 10 µM antisense/reverse oligonucleotide primer, 0.4 µl of Platinum Taq DNA polymerase (5 U/µl) (Invitrogen), and 32.1 µl of DEPC H$_2$O. The reaction is incubated for 2 minutes at 94° C. before proceeding on to 35 cycles of 94° C. for 1 minute, 56° C. for 30 seconds, and 68° C. for 30 seconds. The reaction then is cooled to 4° C. and kept at −20° C. until loading of the reaction onto an agarose gel for analysis.

8.3(c) Visualization, Measurement, Quantitation, and Scoring:

RT-PCR products are run on a 1% agarose gel, in 1×TBE buffer, imaged with a BioRad Gel Doc 2000 in brightfield mode, analyzed, and quantitated with Quantity One software (BioRad). The agarose gels are not stained with ethidium bromide; instead 10 µl of RT-PCR product is mixed with 2 µl of EZ-Vision Three, 6× loading dye (Amresco) prior to loading onto the agarose gel. A Low DNA Mass Ladder (Invitrogen) is also utilized to provide both accurate and consistent MW size and mass measurements. Values are normalized based upon the control RT-PCR amplification of both beta tubulin and GAPDH. Intensity values differences in samples which are greater than 25% of the mean intensity value are considered significant.

8.3(d) Controls:

Master mixes of reagents are utilized in order to minimize variability. Samples for RT-PCR are prepared together, total RNA concentration determined by A260, oligo dT utilized to prime all RT reactions, and the samples equilibrated not just for RNA content, but also normalized based upon amplification of two control primers sets. which amplify beta tubulin and GAPDH. Low DNA Mass Ladder (Invitrogen) is used to provide a consistent normalization reference from gel to gel.

8.4. Immunohistological (1H) Analysis:

Biopsies of tissue will be washed three times with PBS, fixed for 1 hour at room temperature in 3% paraformaldehyde, and washed three times with PBS. Samples will be either paraffin embedded or frozen/embedded in Optimal Cutting Temperature compound, (OCT, Tissue-Tek), and sectioned with a microtome or cryostat. Slides will be viewed by indirect immunofluorescence using an inverted microscope (model IX70; Olympus) fitted with an IX-FLA fluorescence observation attachment and a MicroMax 5-mHz CCD camera (Princeton Instruments) controlled by IP Lab (Scanalytics).

For the purpose of immunohistochemical staining of cell lines, subconfluent monolayers of HIPEC lines will be grown on glass cover slips (Fisher Scientific), rinsed three times with PBS (10 mM sodium phosphate, pH 7.4, 127 mM NaCl), fixed in cold methanol, washed three times with PBS, blocked with 5% goat serum (Sigma-Aldrich)/PBS, and incubated with primary antibodies against the appropriate antigen being examined or an appropriate isotype-matched control antibody, followed by detection with appropriate fluorescent conjugated secondary antibodies. Methanol fixation may also be replaced with a 1 hour room temperature fixation in 3% paraformaldehyde. Slides will be counterstained with DAPI during the last 5 minutes of the secondary antibody incubation.

Immunofluorescence levels will be quantitated from digital images (average of 9, each 1300×1030 pixels, 437×346 µm) recorded using a 20× microscope objective with IPLab 3.7 software (Scanalytics). A segmentation range will be chosen to subtract background and accellular immunofluorescence. The sum of pixels and their intensities in highlighted cellular areas of fluorescence will be measured and normalized by dividing by the number of cells determined from a count of DAPI-stained nuclei for each image. Data will be expressed as the mean and standard deviation of normalized summed intensities with the data analyzed by one-way ANOVA with Holm-Sidak comparisons in SigmaPlot v.9.01 and SigmaStat v3.1 (Jandel).

When intracellular epitopes need to be stained, the cells will be permeabilized with 0.1% Triton X-100 in PBS on ice for 5 minutes. Slides are blocked with 5% goat serum and stained with primary and appropriate secondary antibodies conjugated with FITC, Cy3, or Cy5 (Jackson ImmunoResearch Laboratories). Control staining is achieved using the appropriate IgG or IgM. Nuclear staining is accomplished with DAPI. Immunofluorescence and phase microscopy is performed on an inverted microscope (model IX70; Olympus) with IX-FLA fluorescence and CCD camera, and the data collected and analyzed utilizing IPLab v.3.52 (Scanalytics). The spatial location and signal intensity (using IPLab) difference of any epitope based upon immunoflourescence with a change in total intensity of 25% between disease affected and unaffected tissue regions will be considered significant. In order to be considered a validated biomarker for any given sample according to the described invention, (1) there must be a demonstration of about 80% or higher intensity differential value or alteration in spatial location of the epitope between disease affected and the paired unaffected or normal tissue and/or cells; (2) the alteration in expression of this identified biomarker must be exclusive to the disease condition; (3) there must be a demonstration of its alteration repeatable in at least 50% of a panel of unrelated disease controls.

8.5. Western Blot Analysis:

For Western blot analysis, cell lysate samples containing 50 µg of protein per lane will be run on a 7.5% SDS-PAGE gel under reducing conditions and transferred to nitrocellulose by electroblotting. The blot then will be incubated with primary antibodies, followed by detection with HRP-conjugated secondary antibodies.

8.6. Protein Visualizations and Quantifications.

Protein concentrations are determined by absorbance at 280 nm, Bradford assay (BioRad Laboratories), amino acid analysis, and compared against known standards in Coomassie blue-stained gels. Proteins are solubilized in Laemmli sample buffer and evaluated by SDS-PAGE under reducing conditions on 3.5-12% linear gradient, 6%, or 10% acrylamide gels. Electrophoresed gels are stained with Coomassie Brilliant Blue R-250, imaged with a BioRad Gel Doc 2000 in brightfield mode, and analyzed with Quantity One software (BioRad).

8.7. Immunoprecipitation (IP) and Immunoblotting (IB).

Cell lysates of adherent cells are prepared by washing the cells with cold PBS, followed by disruption in lysis buffer ((50 mM Tris, pH 7.4, 100 mM NaCl, 0.5 mM EDTA, 1% Triton X-100, 1% SDS, and protease and phosphatase inhibitor cocktails (Sigma-Aldrich); diluted 1:10 and 1:100, respectively) and centrifuged to remove the cellular debri pellet. Immunoprecipitations are performed at 4° C. with the addition of protease inhibitor cocktails (Sigma-Aldrich) to all the protein samples and buffers. Conditioned medium or lysates are precleared with 20 µl of an equal mixture of protein A-agarose and protein G-Sepharose bead slurry. Samples are incubated with antibody overnight and precipitated with 40 µl protein A-agarose or protein G-Sepharose beads for 2 hours and followed by washing in 50 mM Tris-HCl, pH 7.5, 150 mM NaCl, 1% NP-40, and 0.1% SDS. After an additional wash, the supernatant is removed and the immunoprecipitates are analyzed by SDS-PAGE. After SDS-PAGE is performed, proteins from the gels are electrophoretically transferred onto polyvinylidene difluoride membranes (PVDF; BioRad) using an electroblotter, blocked with 5% nonfat dried milk and 0.2% Tween 20 in 150 mM NaCl, 50 mM Tris-HCl; pH 7.4, and incubated with primary antibodies followed by HRP-conjugated secondary antibodies (Pierce). Blots are developed with ECL reagents (Amersham Biosciences). Band intensities are quantified from the membrane or scanned films using Quantity 1 software (Bio-Rad Laboratories) after data acquisition with a gel documentation system (ChemiDoc XRS; Bio-Rad Laboratories).

8.8. Electron Microscopy (EM)

Ultrastructural studies will be performed utilizing a Jeol JEM-1200EX electron microscope. Confluent monolayers of cells grown on transwell nylon membranes (Costar) will be fixed with glutaraldehyde and then treated with osmium tetroxide. After dehydration in ethanol, the samples will be embedded in Epon. Thin sections will be stained with uranyl acetate and lead citrate. In some cases, embedded monolayers will be reembedded and sectioned perpendicularly.

8.9. RNA Array Analysis

An Affymetrix GeneChip Human Genome U133 Plus 2.0 Array (47,000 characterized transcripts) will be utilized for RNA expression analysis. Either Affymetrix Exon 1.0 ST Arrays or Gene 1.0 ST Arrays will be utilized; both provide a detailed examination of expression levels and an examination of alternative splicing of the genes included on the array. RNA isolation will be according to the Affymetrix protocol. The slides will be scanned using a Microarray Scanner (UMDNJ-RWJMS's Cancer Institute Microarray Facility, Piscataway, N.J.). The fluorescence intensities will be calculated using the GenePix 3.05 software. Microarray results will be derived by comparing total RNA from experimental (affected) HIPECs (Cy5-labeled) vs. control (unaffected) HIPECs (Cy3-labeled). These results will be analyzed using GeneSpring software (Silicon Genetics). Artifact correction will be applied using an intensity-dependent normalization (Lowess normalization). The average expression level of each gene in the two groups will be calculated and the cutoff value set to 1.7 or 0.5 for the ratio of median. Generally, cutoff values are assigned as above 2 and below 5, for up and/or down regulation respectively, of gene expression.

The cDNA sequence of genes identified via the gene microarrays will be obtained from GenBank and RT-PCR primers synthesized (Integrated DNA Technologies) for their detection. As described above, total RNA will be isolated from the cells, primed with oligo (dT)20 primers, reverse transcribed with ThermoScript RT, and amplified with the use of a Techne PROGENE thermal cycler and Plat Taq (Invitrogen). DNA sequencing will be performed upon RT-PCR products to further verify their identity.

8.10. Electron Microscopy:

8.10(a) Thin Sections of Cell Layers.

HIPEC cells are plated in 60 mm Permanox dishes (Nalgene Nunc) at least 2 days before the experiment. The next day the media is changed. The media is removed and the adherent cells washed once in PBS. The cells are fixed in 0.5% gluteraldehyde and 0.2% tannic acid in PBS for 1 hour at room temperature, and then transferred to modified Karnovsky's fixative (4% formaldehyde and 2.5% gluteraldehyde containing 8 mM $CaCl_2$ in 0.1M sodium cacodylate buffer, pH 7.4). Samples are washed with PBS and post-fixed in 1% osmium tetroxide in 0.1M sodium cacodylate buffer, pH 7.4 for 1 hour to produce osmium black. Samples then are dehydrated through a graded series of ethanol and embedded in Epon/SPURR resin (EM Science) polymerized at 65° C. overnight. Sections (approximately 90 nm) are cut with a diamond knife and stained with saturated uranyl acetate (20 minutes) followed by 0.2% lead citrate (2.5 minutes). Images are photographed with a Jeol JEM-1200EX electron microscope (JEOL) as described in Tsiper et al., 2002, incorporated herein by reference.

8.10(b) Microscopy of EB Sections:

Slides are viewed by indirect immunofluorescence using an inverted microscope (Model IX70; Olympus) fitted with an IX-FLA fluorescence observation attachment and a Micro-Max 5-mHz CCD camera (Princeton Instruments) controlled by IP Lab (Scanalytics).

8.10(c) Gel Electrophoresis of Biomarkers

FIG. 1 shows biomarkers from patients with inflammatory bowel disease (IBD). Total RNA was extracted from a panel (normal control (NL); ulcerative colitis (UC); and Crohn's disease (CD)) of HIPEC monolayers and processed for RT-PCR (35 cycles) with specific primers. Electrophoresis of amplified PCR products on 1.8% agarose gel and subsequent staining with ethidium bromide, showed distinct bands of predicted molecular weight for MIP1α, RHO GTPase, MMP1 and Rantes. Detection of glyceraldehyde-3-phosphate dehydrogenase (G3PDH; housekeeping gene) mRNA in all lanes served as a control (lower panels) for normalization. All four genes examined were aberrantly expressed in UC, CD, or in both when compared to NL control which is consistent with the gene array data.

Example 9

Development of Therapeutic Agents for Colon Cancer

Antibodies are developed against identified surface and/or secretory proteins that are abnormally expressed in colon cancer by a standard protocol. Briefly, this protocol includes the following steps: 1) immunization of mice (in vitro or in vivo); 2) spleen removal and preparation of a single cell suspension; 3) myeloma cell preparation; 4) fusion of spleen cells and myeloma cells; 5) post-fusion cells cultured in hybridoma selection medium (HAT); 6) collection and dispersion of peritoneal macrophages; 7) addition of fused cells to microtiter plates with macrophage (48 hours post-fusion (2-4×10$^6$ cells/ml)); 8) culture of cells: 37° C., 5% $CO_2$ [feed with HAT medium]; 9) 7 to 21 days post fusion, observe and numerate hybridoma clones; 10) screen for specific antibody production; 11) expand positive cultures by screening test; 12) redone by limiting dilution technique all positive hybridoma clones to assure monoclonality and to select for the fastest growing cell line with the greatest antibody production; hybridomas will be be recloned periodically (after 3 to 4 months of culture) to prevent overgrowth of the preferred culture by mutants or cells expressing an altered phenotype; 13) inject 2-10×10$^6$ recloned hybridoma cells into BALB/c mice which had received an i.p. injection of 0.3 ml of pristane 7 days previously; and collect ascites 7-21 days latter; and 14) guard against loss of the hybridoma by storing several ampules of each clone in liquid nitrogen.

Example 10

Differential mRNA Expression Pattern of Several Cell Lines Demonstrated by RT-PCR

10.1(a) RT-PCR Analysis

RT-PCR analysis entails four steps: RNA purification, the RT reaction, the RT-PCR reaction, and visualization/quantitation/scoring of RT-PCR products. An oligo(dT)$_{20}$ primer is utilized to prime the RT reaction rather than a gene specific primer (GSP) to reduce the effort and costs which would be incurred by having to individually prime each RT-PCR reaction with a GSP and to keep the starting material as equilibrated as possible between samples and RT-PCR reactions with a minimum of effort.

10.1(b) Purification of Total RNA

Total RNA was purified from adherent cells growing in tissue culture flasks. Cells grown in culture were lysed directly in the culture dish by the addition of 1 ml of TRIzol per 10 cm$^2$ of dish surface area and by repetitive pipetting. After homogenization, samples were allowed to sit for 5 minutes at 15-30° C. (room temperature) in order to allow dissociation of nucleoprotein complex. 0.2 ml of chloroform was added per ml of TRIzol utilized to homogenize the cells or tissue samples. Samples were shaken vigorously by hand for 15 seconds and then incubated at 15-30° C. for 3 minutes. Samples then were centrifuged 12,000×g for 15 minutes at 2-8° C. The upper aqueous phase was removed to a fresh tube and 0.5 ml of isopropanol per ml of TRIzol utilized in the initial homogenization was added to the tube. The sample was vortexed for 1 minute, incubated for 10 minutes at 15-30° C., and then centrifuged at 12,000×g for 10 minutes at 2-8° C. The supernatant was removed and the pellet washed with 75% ethanol; such that 1 ml of ethanol per ml of Trizol was utilized. The pellet was allowed to air dry and then resuspended in DEPC treated distilled filtered $H_2O$. Total RNA purified then was measured utilizing a spectrophotometer and absorbance at $A_{260}$.

10.1(c) RT Reaction

The RT and PCR reactions and incubations were performed in a thermal cycler with a heated lid. AlfaGene typically employs a Techne PROGENE thermal cycler for the RT and PCR reactions. The primers and thermocycler protocols utilized are shown in Table 7 and Table 8, respectively.

TABLE 7

| Primers Gene target | designation | primer sequence (5'→3') | SEQ ID NO |
|---|---|---|---|
| | | upstream/sense primer | |
| Nanog | hNanog-2f | ATGCCTGTGATTTGTGGGCC | SEQ ID NO: 1 |
| LIN28 | hLIN28-1f | CAACCAGCAGTTTGCAGGTGGCTG | SEQ ID NO: 2 |
| Oct4 (variant 1 and 2) | hOct4f-2 | CATCAAAGCTCTGCAGAAAGAACTC | SEQ ID NO: 3 |
| Oct4 (variant 1) | hOct4f-4 | CGGGACACCTGGCTTCGGATTTCG | SEQ ID NO: 4 |
| Oct4 (variant 2) | hOct4f-5 | CATGAGTCAGTGAACAGGGAATG | SEQ ID NO: 5 |

TABLE 7-continued

| Primers Gene target | designation | primer sequence (5'→3') | SEQ ID NO |
|---|---|---|---|
| SOX2 | hSOX2-6f | CAAAAGTCTTTACCAATAATATTTAGAG | SEQ ID NO: 6 |
|  | hSOX2-5f | TAAAAGTTCTAGTGGTACGGTAGGAG | SEQ ID NO: 7 |
| Bmi1 | bmi-f1 | CATAATAGAATGTCTACATTCCTTCTG | SEQ ID NO: 8 |
| LGR5 | hLGR5-8f | GATCTGTCTTACAACCTATTAGAAG | SEQ ID NO: 9 |
| β-tubulin | BT8 | CTGAAAACACATGTAGATAATGGC | SEQ ID NO: 10 |
| TLR1 | hTLR1f-4 | GTTCTTGGACTAAAAGTTTATTAAG | SEQ ID NO: 11 |
| TLR2 | hTLR2f-2 | CTTATCCAGCACACGAATACACAG | SEQ ID NO: 12 |
| TLR4 | hTLR4f | TGGATACGTTTCCTTATAAG | SEQ ID NO: 13 |
| TLR6 | hTLR6f | TTGGACTCATATCAAGATGCTCTG | SEQ ID NO: 14 |
| TLR10 | hTLR10f | ATGCTTTTCCCGAATTATCCTACG | SEQ ID NO: 15 |
| myD88 | myD88f-2 | CTCCAGGACCGCCCGCCATGGCTG | SECQID NO: 16 |
| IL8 | IL8-1 | CTGTGTGTAAACATGACTTCCAAG | SEQ ID NO: 17 |
| IFIT1 | IFIT1-F2 | CAGCAACCATGAGTACAAATGGTG | SEQ ID NO: 18 |
| EDIL3 | EDIL3-F1 | GAAATTGTCAATACAAATGCTCAG | SEQ ID NO: 19 |
| BST2 | BST2-F2 | CCTGCAACCACACTGTGATGGCC | SEQ ID NO: 20 |
| API2 | API2-F1 | CCAAGTGGTTTCCAAGGTGTGAG | SEQ ID NO: 21 |
| PCSK5 | PCSK5-F1 | CAGAGGATTATGCAGGTCCCTGC | SEQ ID NO: 22 |
| RGS2 | RGS2-F2 | GCAAGCTTTCATCAAGCCTTCTC | SEQ ID NO: 23 |
| RASA2 | RASA2-F4 | CTTGTTGTACACATCAAGGCATGC | SEQ ID NO: 24 |
| TNFAIP6 | TNFAIP6-F1 | CCATATGGCTTGAACGAGCAGCCG | SEQ ID NO: 25 |
| TIMP3 | TIMP3-F1 | CAAGCAGATGAAGATGTACCGAG | SEQ ID NO: 26 |
| STX11 | STX11-F3 | GAGGAGTATGTGAATTCTTTGGAG | SEQ ID NO: 27 |
| STX5 | STX5-F1 | CACCCTCATGGCCAAGCGCATTG | SEQ ID NO: 28 |
| oligo dT (20mer) |  |  |  |

| | | downstream/antisense primer | |
|---|---|---|---|
| Nanog | hNanog-6r | CTCATCTTCACACGTCTTCAGGTTG | SEQ ID NO: 29 |
| LIN28 | hLIN28-5r | GAACCCTCACTTGCATTTGGACAGAG | SEQ ID NO: 30 |

TABLE 7-continued

| Gene target | Primers designation | primer sequence (5'→3') | SEQ ID NO |
|---|---|---|---|
| Oct4 (variant 1 and 2) | hOct4r-3 | CTGCTTGATCGCTTGCCCTTCTGGC | SEQ ID NO: 31 |
| Oct4 (variant 1) | hOct4r-5 | CTTGTAAGAACATAAACACACCAG | SEQ ID NO: 32 |
| Oct4 (variant 2) | hOct4-z | GGTTTCTGCTTTGCATATCTCCTG | SEQ ID NO: 33 |
| SOX2 | hSOX2-7r | GCCGAATCTTTTAAAATACAACTACG | SEQ ID NO: 34 |
|  | hSOX2-7r | GCCGAATCTTTTAAAATACAACTACG | SEQ ID NO: 35 |
| Bmi1 | bmi-r4 | GGAAGTGGACCATTCCTTCTCCAG | SEQ ID NO: 36 |
| LGR5 | hLGR5-3r | CTTCAAGGTCACGTTCATCTTGAGC | SEQ ID NO: 37 |
| β-tubulin | BT9R | CTGGAGGCTTAGGGACCAAGGCTG | SEQ ID NO: 38 |
| TLR1 | hTLR1r-3 | GTGATAACTGCTAGGAATGGAGTAC | SEQ ID NO: 39 |
| TLR2 | hTLR2r | TTGAAGTTCTCCAGCTCCTG | SEQ ID NO: 40 |
| TLR4 | hTLR4r | GAAATGGAGGCACCCCTTC | SEQ ID NO: 41 |
| TLR6 | hTLR6r | TCAGAATTTGTAGACTTTCTGTCTC | SEQ ID NO: 42 |
| TLR10 | hTLR10r | CAACCATCATGACCTCTGAATATG | SEQ ID NO: 43 |
| myD88 | myD88r-3 | GTTCCAGTTGCCGGATCATCTCCTG | SEQ ID NO: 44 |
| IL8 | IL8-6 | GAATTTTTTTATGAATTCTCAGCCCTC | SEQ ID NO: 45 |
| IFIT1 | IFIT1-R2 | CACCTTTTCAAAGCAGGCCTTGGC | SEQ ID NO: 46 |
| EDIL3 | EDIL3-R1 | CAGAGGCTCAGAACAACCCGACAG | SEQ ID NO: 47 |
| BST2 | BST2-R1 | CTTCCAAGATGTGCCAGCTTCCTG | SEQ ID NO: 48 |
| API2 | API2-R2 | CTTCCACTGGTAGATCTGAAACATC | SEQ ID NO: 49 |
| PCSK5 | PCSK5-R1 | CAGCTCCTGCCCCAGCACAAGTG | SEQ ID NO: 50 |
| RGS2 | RGS2-R1 | GATAAGAGTTGTTCTCCATCAAG | SEQ ID NO: 51 |
| RASA2 | RASA2-R4 | GGCAGATATTGGTTGAACATCTG | SEQ ID NO: 52 |
| TNFAIP6 | TNFAIP6-R2 | CTCATCTCCACAGTATCTTCCCAC | SEQ ID NO: 53 |
| TIMP3 | TIMP3-R2 | GTTCCCAATAAACCCCATATGACAG | SEQ ID NO: 54 |

TABLE 7-continued

| Primers Gene target | designation | primer sequence (5'→3') | SEQ ID NO |
|---|---|---|---|
| STX11 | STX11-R3 | CATGTGCCAGGCACTGTTCTAGGTG | SEQ ID NO: 55 |
| STX5 | STX5-R2 | GACTCTGGATGTAGGAATCCTGCTC | SEQ ID NO: 56 |
| oligo dT (20mer) | (dT)20 | TTTTTTTTTTTTTTTTTTTT | SEQ ID NO: 57 |

TABLE 8

Thermocycler Protocols

| | | PCR parameters | | | | | | Positive control for RT PCR was |
|---|---|---|---|---|---|---|---|---|
| | PCR product | denaturation step | | annealing step | | extension step | | total RNA |
| Gene target | size (bp) | temp (° C.) | duration (min:sec) | temp (° C.) | duration (min:sec) | temp (° C.) | duration (min:sec) | # of cycles | prepared from: |
| Nanog | 852 | 94.0 | :40 | 56.0 | :30 | 73.0 | 1:00 | 35 | |
| LIN28 | 828 | 94.0 | :40 | 56.0 | :30 | 73.0 | 1:00 | 35 | |
| Oct4 (variant 1 and 2) | 455 | 94.0 | :40 | 56.0 | :30 | 73.0 | :45 | 30 | |
| Oct4 (variant 1) | 828 | 94.0 | :40 | 56.0 | :30 | 73.0 | 1:00 | 35 | |
| Oct4 (variant 2) | 471 | 94.0 | :40 | 56.0 | :30 | 73.0 | :45 | 40 | |
| SOX2 | 581 | 94.0 | :40 | 56.0 | :30 | 73.0 | :45 | 35 | |
| | 621 | 94.0 | :40 | 56.0 | :30 | 73.0 | :45 | 35 | |
| Bmi1 | 576 | 94.0 | :40 | 56.0 | :30 | 73.0 | :45 | 40 | |
| LGR5 | 498 | 94.0 | :40 | 56.0 | :30 | 73.0 | :45 | 40 | |
| b-tubulin | 385 | 94.0 | :40 | 56.0 | :30 | 73.0 | :45 | 30 | |
| TLR1 | 976 | 94.0 | :40 | 56.0 | :30 | 73.0 | 1:00 | 30 | |
| TLR2 | 676 | 94.0 | :40 | 56.0 | :30 | 73.0 | 1:00 | 30 | |
| TLR4 | 514 | 94.0 | :40 | 56.0 | :30 | 73.0 | 1:00 | 30 | |
| TLR6 | 643 | 94.0 | :40 | 56.0 | :30 | 73.0 | 1:00 | 30 | |
| TLR10 | 615 | 94.0 | :40 | 56.0 | :30 | 73.0 | 1:00 | 30 | |
| myD88 | 566 | 94.0 | :40 | 56.0 | :30 | 73.0 | 1:00 | 30 | |
| IL8 | 319 | 94.0 | :40 | 56.0 | :30 | 73.0 | :30 | 30 | |
| IFIT1 | 508 | 94.0 | :40 | 56.0 | :30 | 73.0 | :45 | 38 | cervix |
| EDIL3 | 514 | 94.0 | :40 | 56.0 | :30 | 73.0 | :45 | 38 | brain |
| BST2 | 305 | 94.0 | :40 | 56.0 | :30 | 73.0 | :30 | 38 | kidney |
| API2 | 698 | 94.0 | :40 | 56.0 | :30 | 73.0 | 1:00 | 38 | kidney |
| PCSK5 | 506 | 94.0 | :40 | 56.0 | :30 | 73.0 | :45 | 38 | thyroid |
| RGS2 | 361 | 94.0 | :40 | 56.0 | :30 | 73.0 | :30 | 38 | prostate |
| RASA2 | 515 | 94.0 | :40 | 56.0 | :30 | 73.0 | :45 | 38 | muscle |
| TNFAIP6 | 558 | 94.0 | :40 | 56.0 | :30 | 73.0 | :45 | 38 | lung |
| TIMP3 | 611 | 94.0 | :40 | 56.0 | :30 | 73.0 | 1:00 | 42 | cervix |
| STX11 | 745 | 94.0 | :40 | 56.0 | :30 | 73.0 | 1:00 | 42 | placenta |
| STX5 | 523 | 94.0 | :40 | 56.0 | :30 | 73.0 | :45 | 42 | prostate |
| oligo dT (20mer) | | | | | | | | | |

Typical RT reactions were performed in a 26 ul reaction volume with 2 ug of total RNA, 2 ul of 50 uM oligo(dT)$_{20}$ to prime the RT reaction, and 4 ul of 10 mM dNTP. The reaction was incubated for 5 minutes at 65° C. and then quickly cooled to 4° C. A 14 ul mixture composed of 8 ul of 5× cDNA synthesis buffer (250 mM Tris acetate; pH 8.4, 375 mM potassium acetate, 40 mM magnesium acetate, and a stabilizer; Invitrogen), 2 ul of 0.1M DTT, 2 ul of RNaseOUT (40 U/ul; Invitrogen), and 2 ul of ThermoScript RT (15 U/ul; Invitrogen) was added to the microcentrifuge tube containing the annealed 26 ul reaction. The combined 40 ul reaction was heated to 55° C. for 60 minutes; the temperature is raised to 85° C. for 5 minutes, before returning it to 4° C. 2 ul of RNAse H (Invitrogen) was added to the mixture and the tubes heated to 37° C. for 20 minutes followed by cooling to 4° C. 4 ul of this RT reaction was used in the subsequent 50 ul PCR reactions.

10.1(d) PCR Reaction

Master mixes comprised of everything except the RT product were utilized in order to maximize efficiency and minimize both effort and sample-to-sample, as well as experiment to experiment, amplification variability. A 50 ul PCR reaction was assembled using 4 ul from the prepared RT reaction described earlier, 5 ul of 10× Plat Taq PCR buffer Minus Mg (Invitrogen), 1.5 ul of 50 mM $MgCl_2$, 1 ul of 10 mM dNTP, 3 ul of a 10 uM stock of sense/forward target gene specific oligonucleotide primer, 3 ul of 10 uM antisense/reverse oligonucleotide primer, 0.4 ul of Platinum Taq DNA polymerase (5 U/ul; Invitrogen), and 32.1 ul of DEPC $H_2O$. The reaction was incubated for 2 minutes at 94° C. before proceeding onto 35 cycles of 94° C. for 1 minute, 56° C. for 30 seconds, and 68° C. for 30 seconds. The reaction was then cooled to 4° C. and kept at −20° C. untiil is was loaded on to an agarose gel for analysis.

10.1(e) Visualization, Measurement, Quantitation, and Scoring

RT-PCR products were run on a 1% agarose gel in 1×TBE buffer, imaged with a BioRad Gel Doc 2000 in brightfield mode, analyzed, and quantitated with Quantity One software (BioRad). Agarose gels were not stained with ethidium bromide, instead 10 ul of RT-PCR product was mixed with 2 ul of EZ-Vision Three, 6× loading dye (Amresco) prior to loading onto the agarose gel. A Low DNA Mass Ladder (Invitrogen) was also utilized to provide both accurate and consistent MW size and mass measurements. Values are normalized based upon the control RT-PCR amplification of both beta tubulin and GAPDH. Intensity values differences in samples which are greater than 25% of the mean intensity values are considered significant.

10.1(F) Controls

Master mixes of reagents were utilized in order to minimize variability. Samples for RT-PCR were prepared together, total RNA concentration determined by $A_{260}$, oligo dT utilized to prime all RT reactions, and the samples equilibrated for RNA content, and normalized based upon amplification of two control primers sets, which amplify beta tubulin and GAPDH. The use of the Low DNA Mass Ladder (Invitrogen) provides a consistent normalization reference from gel to gel.

Figure 11:
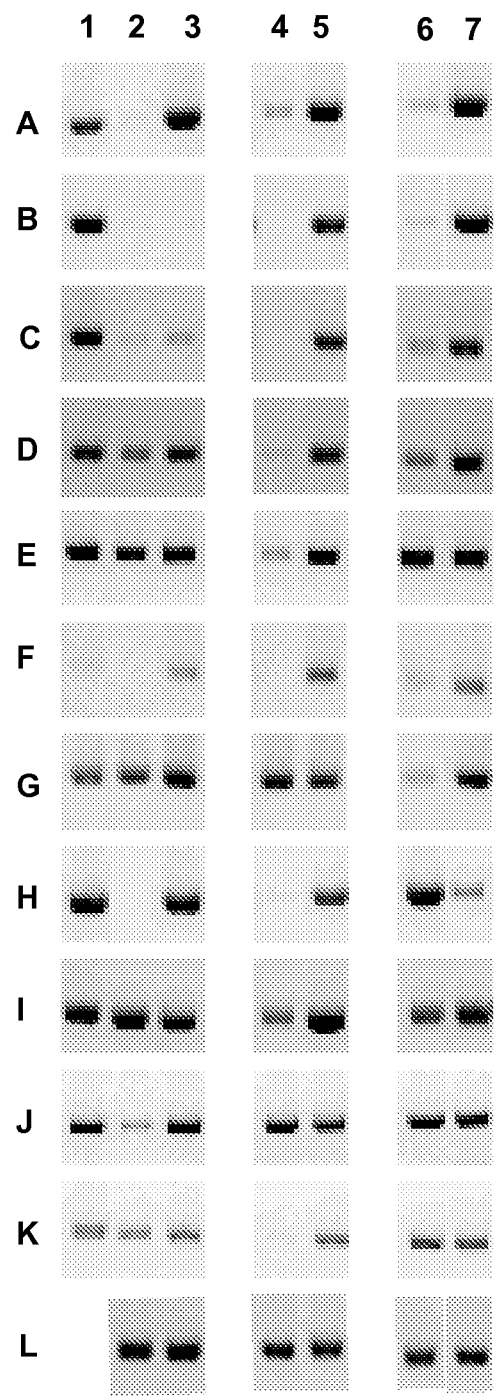
FIG. 11 shows RT-PCR amplicons derived from normal cells and gastrointestinal diseased cells. Lane 1: positive control; Lane 2: normal CRC cell line; Lane 3, diseased CRC cell line; Lane 4: non-active ulcerative colitis cell line; Lane 5: active ulcerative colitis cell line; Lane 6: non-active Crohn's disease cell line; Lane 7: active Crohn's disease cell line; Row A: IFIT-1 (508 bp); Row B: EDIL3 (514 bp); Row C: PCKS5 (506 bp); Row D: BST2 (305 bp); Row E: RGS2 (361 bp); Row F: RASA2 (515 bp); Row G: TNFAIP6 (558 bp); Row H: API2 (698 bp); Row I: TIMP3 (611 bp); Row J: STX11 (745 bp); Row K: STX5 (523 bp); Row L: BT (508 bp).

FIG. 11 shows RT-PCR amplicons derived from normal cells and from gastrointestinal diseased cells. FIG. 11 (lane 2) shows that normal cells display a IFIT-1(−), EDIL3(−), PCSK5(lo), BST2(+), RGS2(+), RASA2(−), TNFAIP6(+), AIPI2 (−), TIMP3(+), STX11(+), STX5 (+), BT(+) phenotype; CRC cells (lane 3) display a IFIT-1(+), EDIL3(−), PCSK5(lo), BST2(+), RGS2(+), RASA2(+), TNFAIP6(+), AIPI2 (+), TIMP3(+), STX11(+), STX5(+), BT(+) phenotype.

FIG. 11 (lane 4) shows that non-active ulcerative colitis cells display a IFIT-1(+), EDIL3(−), PCSK5(−), BST2(+), RGS2(+), RASA2(−), TNFAIP6(+), AIPI2 (−), TIMP3(+), STX11(+), STX5(−), BT(+) phenotype; cells with active ulcerative colitis (lane 5) displayed a IFIT-1(+), EDIL3(−), PCSK5(+), BST2(+), RGS2(+), RASA2(+), TNFAIP6(+), AIPI2 (+), TIMP3(+), STX11(+), STX5(+), BT(+) phenotype.

FIG. 11 (lane 6) shows that non-active Crohn's disease cells display a IFIT-1(lo), EDIL3(lo), PCSKT(lo), BST2(+), RGS2(+), RASA2(lo), TNFAIP6(lo), AIPI2 (+), TIMP3(+), STX11(+), STX5(+), BT(+) phenotype; active Crohn's disease cells (lane 7) display a IFIT-1(+), EDIL3(+), PCSKT(+), BST2(+), RGS2(+), RASA2(+), TNFAIP6(+), AIPI2 (−), TIMP3(+), STX11(+), STX5(−), BT(+) phenotype.

These results show that according to the described invention, normal and diseased cells can be distinguished from each other by RT-PCR to analyze the differential mRNA expression of the biomarker set.

Example 11

Figure 12:
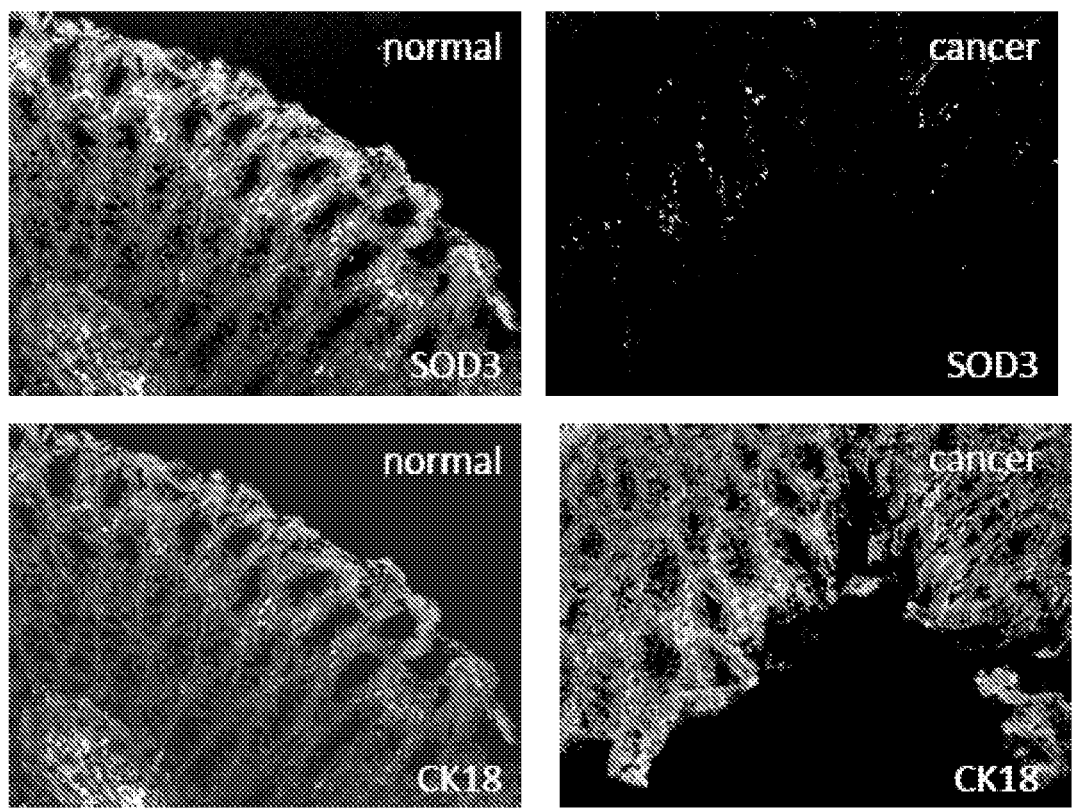
FIG. 12 shows an immunohistochemical comparison of the differential expression of SOD3 between cancer and normal colonic tissue from patients with CRC. Right panel: cancerous tissue; left panel: normal counterpart.
Figure 13:
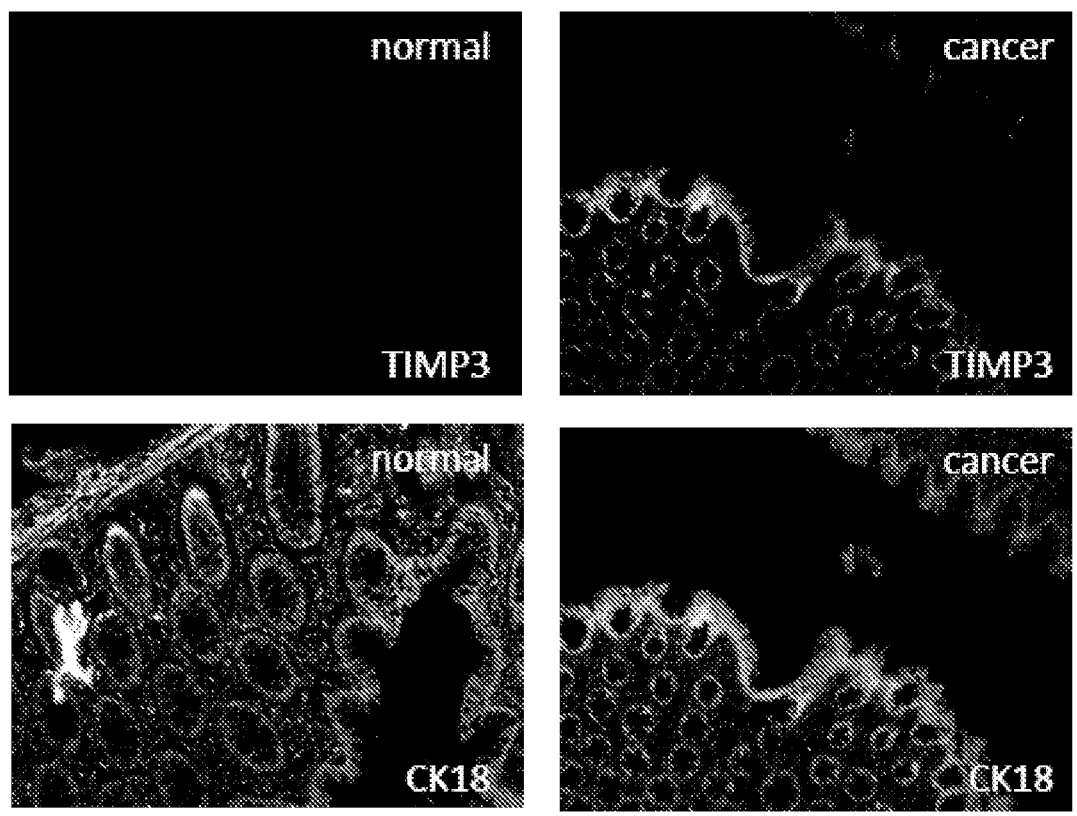
FIG. 13 shows immunohistochemical comparison of the differential expression of TIMP3 between cancer and normal colonic tissue from patients with CRC. Right panel: cancerous tissue; left panel: normal counterpart.
Figure 14:
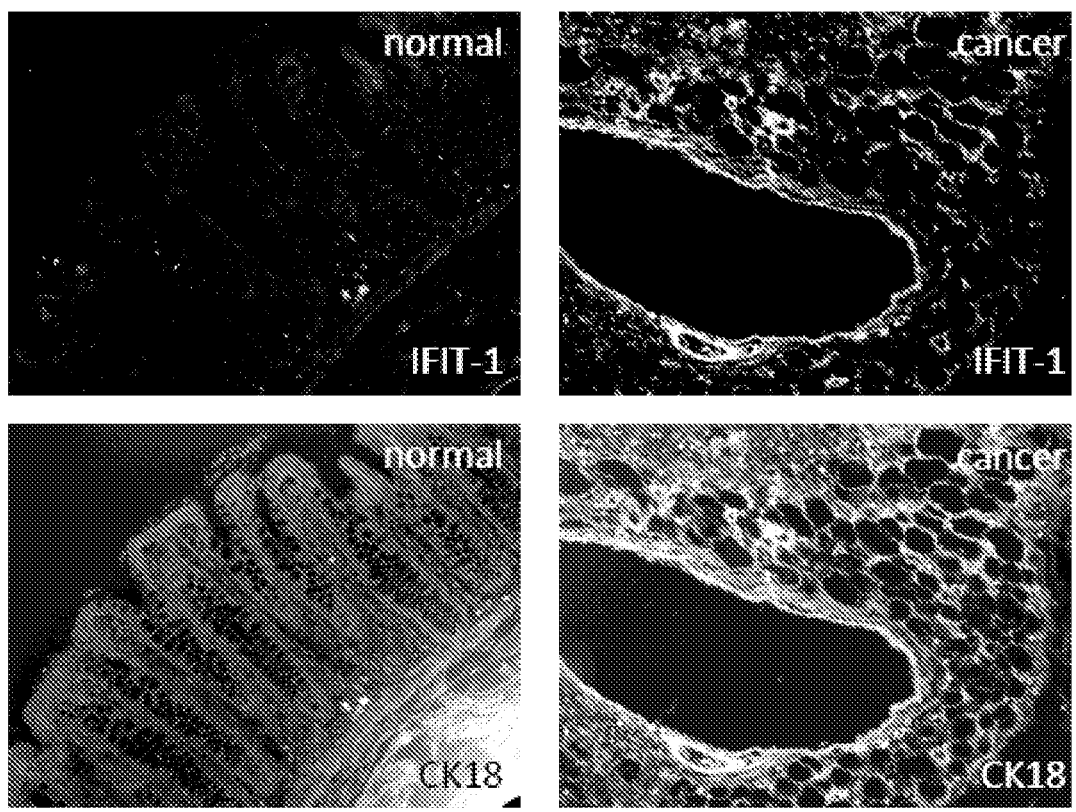
FIG. 14 shows immunohistochemical comparison of the differential expression of IFIT-1 between cancer and normal colonic tissue from patients with CRC. Right panel: cancerous tissue; left panel: normal counterpart.
Figure 15:
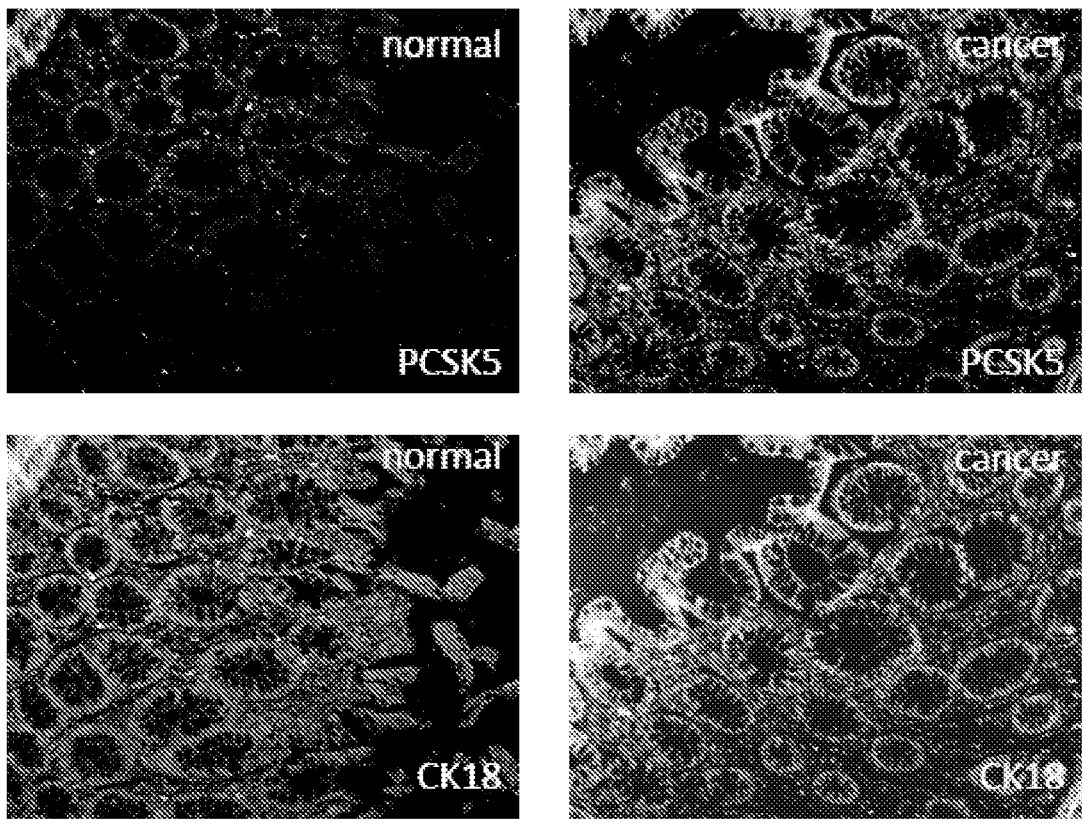
FIG. 15 shows immunohistochemical comparison of the differential expression of PCSK5 between cancer and normal colonic tissue from patients with CRC. Right panel: cancerous tissue; left panel: normal counterpart.

Immunohistochemical Comparison of the Differential Expression of SOD3 Between Cancer and Normal Colonic Tissue from Patients with CRC Paired cancerous and normal tissue samples from patients with gastrointestinal cancer who underwent surgical treatment at the JSS Medical College Hospital, Mysore, India were obtained within 30 minutes from the surgery and were washed three times with PBS, fixed for 1 hour at room temperature in 3% paraformaldehyde, and washed three times with PBS. Samples were paraffin embedded and sectioned with a microtome. Postoperative clinical diagnosis was confirmed by an expert pathologist. Subsequently, histological sections (4 micron thickness) were cut from the paraffin blocks and embedded on glass slides for immunohistochimical staining with rabbit polyclonal antibodies (abCAM, Cambridge, Mass.) against human SOD3 (FIG. 12), TIMP3 (FIG. 13), IFIT-1 (FIG. 14), and PCSK5 (FIG. 15). The histological sections were de-paraffinized and washed 2×5 minutes in TBS plus 0.25% Triton X-100 with gentle agitation. Tissue sections then were blocked with 10% normal serum with 1% BSA in TBS for 2 hours at room temperature. Sections from each of the paired tissue sections were dual stained by incubation with primary antibodies (1:1000 dilution in TBS with 1% BSA) against the above mentioned antigens (TIMP3, SOD3, IFIT1, and PCSK5) or by incubation with an isotype matched control antibody for two hours at room temperature. Slides then were rinsed 3×5 minutes in TBS 0.025% triton with gentle agitation. Subsequently, a secondary red fluorochome-conjugated (Alexa Fluor—Invitrogen) goat anti-rabbit IgG (1:100 dilution) was added and incubated for 1 hour. Slides also were stained with a FITC conjugated mouse anti-human cytokeratin 18 antibody (Sigma) or an FITC conjugated goat anti mouse control IgG. Finally, the slides were rinsed 3×5 min in TBS and mounted with one drop of mounting medium (Fluoroguard, BioRad) and a glass cover slip. Stained tissue samples then were analyzed using a Nikon Eclipse 80i microscope fitted with a fluorescence observation attachment and a Cool Snap CCD camera (Photometric) controlled by Nikon Imaging System (NIS—Elements AR) software.

Exemplary antibodies useful for this protocol include, but are not limited to, mouse anti-human CK18 monoclonal IgG1 FITC conjugated antibody (for cytokeratin-18 (CK18)) (Sigma, St. Loius, Mo.); rabbit polyclonal anti-human SOD3 IgG (for superoxide dismutase 3 (SOD3)) (AbCam, Cambridge, Mass.); rabbit polyclonal anti-human PCSK5 IgG (for proprotein convertase subtilisin/kexin type 5 (PCSK5)) (Abcam, Cambridge, Mass.); rabbit polyclonal anti-human IFIT1 IgG (for interferon-induced protein with tetratricopeptide repeats 1 (IFIT1)) (Abcam, Cambridge, Mass.); and rabbit polyclonal anti-human TIMP3 IgG, goat anti-rabbit IgG Alexa 546 conjugated IgG (for TIMP metallopeptidase inhibitor 3 (TIMP3)) (Abcam, Cambridge, Mass.).

Results are shown in FIGS. 12-15. These results show that (a) SOD3 (FIG. 12) expression is reduced dramatically in cancerous tissue (right panel) compared to its normal counterpart (left panel); (b) TIMP3 (FIG. 13) expression is increased in cancerous tissue (right panel) compared to its normal counterpart (left panel); IFIT-1 (FIG. 14) expression is increased in cancerous tissue (right panel) compared to its normal counterpart (left panel); and PCSK5 (FIG. 15) expression is increased in cancerous tissue (right panel) compared to its normal counterpart (left panel).

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

I claim:

1. A method for diagnosing colon cancer in a human subject, the method comprising the steps:
   (a) isolating normal differentiable segment-specific human stem cell-like progenitor cells from normal mucosal colon tissue of the human subject;
   (b) isolating diseased differentiable segment-specific human stem cell-like progenitor cells from diseased mucosal colon tissue of the human subject;
   (c) cultivating the normal differentiable segment-specific human stem cell-like progenitor cells from step (a) on a biosimilar matrix environment formed from the normal mucosal colon tissue to produce a normal human intestinal primary epithelial cell line;
   (d) cultivating the diseased differentiable segment-specific human stem cell-like progenitor cells from step (b) on a biosimilar matrix environment formed from the diseased mucosal colon tissue of step (b) to produce a diseased human intestinal primary epithelial cell line;
   (e) measuring the level of expression of one or more biomarker selected from the group consisting of superoxide dismutase 3 (SOD3) and proprotein convertase subtilisin/kexin type 5 (PCSK5), wherein the level of expression of the one or more biomarker is measured in the normal human intestinal primary epithelial cell line of step (c) and in the diseased human intestinal primary epithelial cell line of step (d); and
   (f) diagnosing the subject with colon cancer if a difference between the level of expression of the one or more biomarker measured in the normal human intestinal primary epithelial cell line and the level of expression of the one or more biomarker measured in the diseased human intestinal primary epithelial cell line is selected from the group consisting of an underexpression of SOD3 in the diseased human intestinal primary epithelial cell line, an overexpression of PCSK5 in the diseased human intestinal primary epithelial cell line, and a combination of the foregoing.

2. The method according to claim 1, wherein the one or more biomarker in step (e) is SOD3 so that the subject is diagnosed with colon cancer in step (f) if SOD3 is underexpressed in the diseased human intestinal primary epithelial cell line.

3. The method according to claim 1, wherein said SOD3 is underexpressed at least about 2-fold.

4. The method according to claim 1, wherein the normal differentiable segment-specific human stem cell-like progenitor cells have a phenotype of at least cytokeratin (+) and β-1-integrin(+).

5. The method according to claim 1, wherein the normal differentiable segment-specific human stem cell-like progenitor cells have a phenotype of cytokeratin (+), β-1-integrin (+), defensin-5(+), trefoil factor-3(+), mucin-2(+), chomogranin-A(+), intestinal alkaline phosphatase(+), and lysozyme (+).

6. The method according to claim 1, wherein the one or more biomarker in step (e) is PCSK5 so that the subject is diagnosed with colon cancer in step (f) if PCSK5 is overexpressed in the diseased human intestinal primary epithelial cell line.

7. The method according to claim 1, wherein the one or more biomarker in step (e) is SOD3 and PCSK5 so that the subject is diagnosed with colon cancer in step (f) if SOD3 is underexpressed and PCSK5 is overexpressed in the diseased human intestinal primary epithelial cell line.

8. A method for diagnosing colon cancer in a human subject, the method comprising the steps:
(a) isolating normal differentiable segment-specific human stem cell-like progenitor cells from normal mucosal colon tissue of the human subject;
(b) isolating diseased differentiable segment-specific human stem cell-like progenitor cells from diseased mucosal colon tissue of the human subject;
(c) cultivating the normal differentiable segment-specific human stem cell-like progenitor cells from step (a) on a biosimilar matrix environment formed from the normal mucosal colon tissue to produce a normal human intestinal primary epithelial cell line;
(d) cultivating the diseased differentiable segment-specific human stem cell-like progenitor cells from step (b) on a biosimilar matrix environment formed from the diseased mucosal colon tissue of step (b) to produce a diseased human intestinal primary epithelial cell line;
(e) measuring level of expression of one or more biomarker selected from the group consisting of superoxide dismutase 3 (SOD3), proprotein convertase subtilisin/kexin type 5 (PCSK5), and tissue inhibitor of metalloproteinase 3 (TIMP3), wherein the level of expression of the one or more biomarker is measured in the normal human intestinal primary epithelial cell line of step (c) and in the diseased human intestinal primary epithelial cell line of step (d); and
(f) diagnosing the subject with colon cancer if a difference between the level of expression of the one or more biomarker measured in the normal human intestinal primary epithelial cell line and the level of expression of the one or more biomarker measured in the diseased human intestinal primary epithelial cell line is selected from the group consisting of an underexpression of SOD3 in the diseased human intestinal primary epithelial cell line, an overexpression of PCSK5 in the diseased human intestinal primary epithelial cell line, an overexpression of TIMP3 in the diseased human intestinal primary epithelial cell line, and any combination of the foregoing.

9. The method according to claim 8, wherein the one or more biomarker in step (e) is TIMP3 so that the subject is diagnosed with colon cancer in step (f) if TIMP3 is overexpressed in the diseased human intestinal primary epithelial cell line.

10. The method according to claim 8, wherein the one or more biomarker in step (e) is SOD3 and TIMP3 so that the subject is diagnosed with colon cancer in step (f) if SOD3 is underexpressed and TIMP3 is overexpressed in the diseased human intestinal primary epithelial cell line.

11. The method according to claim 8, wherein the one or more biomarker in step (e) is PCSK5 and TIMP3 so that the subject is diagnosed with colon cancer in step (f) if PCSK5 and TIMP3 are overexpressed in the diseased human intestinal primary epithelial cell line.

12. The method according to claim 8, wherein the one or more biomarker in step (e) is SOD3, PCSK5, and TIMP3 so that the subject is diagnosed with colon cancer in step (f) if SOD3 is underexpressed and PCSK5 and TIMP3 are overexpressed in the diseased human intestinal primary epithelial cell line.

13. The method according to claim 8, wherein the normal differentiable segment-specific human stem cell-like progenitor cells have a phenotype of at least cytokeratin (+) and β-1-integrin(+).

14. The method according to claim 8, wherein the normal differentiable segment-specific human stem cell-like progenitor cells have a phenotype of cytokeratin (+), β-1-integrin (+), defensin-5(+), trefoil factor-3(+), mucin-2(+), chomogranin-A(+), intestinal alkaline phosphatase(+), and lysozyme (+).

* * * * *